United States Patent
Allen et al.

(10) Patent No.: US 10,660,645 B2
(45) Date of Patent: May 26, 2020

(54) EMBOLIZATION SYSTEMS

(71) Applicant: Embo Medical Limited, Enniscorthy (IE)

(72) Inventors: Wayne Allen, County Galway (IE); Colin Forde, County Galway (IE); Liam Mullins, Athlone (IE); Paul Gilson, County Galway (IE)

(73) Assignee: EMBO MEDICAL LIMITED, Galway (IE)

(*) Notice: Subject to any disclaimer, the term of this patent is extended or adjusted under 35 U.S.C. 154(b) by 0 days.

(21) Appl. No.: 14/205,016

(22) Filed: Mar. 11, 2014

(65) Prior Publication Data

US 2014/0276388 A1 Sep. 18, 2014

Related U.S. Application Data

(60) Provisional application No. 61/787,223, filed on Mar. 15, 2013.

(51) Int. Cl.
*A61B 17/12* (2006.01)
*A61B 17/00* (2006.01)

(52) U.S. Cl.
CPC .... *A61B 17/12109* (2013.01); *A61B 17/1215* (2013.01); *A61B 17/12145* (2013.01); *A61B 17/12163* (2013.01); *A61B 2017/00575* (2013.01); *A61B 2017/00592* (2013.01); *A61B 2017/00606* (2013.01); *A61B 2017/00893* (2013.01); *A61B 2017/12054* (2013.01)

(58) Field of Classification Search
CPC ............... A61F 2/013; A61B 17/12163; A61B 17/12145; A61B 17/1215

USPC ................................................ 606/200
See application file for complete search history.

(56) References Cited

U.S. PATENT DOCUMENTS

| | | | |
|---|---|---|---|
| 5,256,146 A | * | 10/1993 | Ensminger ............ A61M 25/04 604/104 |
| 5,573,547 A | | 11/1996 | LeVeen et al. |
| 5,630,844 A | | 5/1997 | Aydin et al. |
| 5,683,411 A | | 11/1997 | Kavteladze et al. |
| 5,693,067 A | | 12/1997 | Purdy |
| 5,702,421 A | | 12/1997 | Schneidt |
| 5,855,578 A | | 1/1999 | Guglielmi |
| 5,911,717 A | * | 6/1999 | Jacobsen .......... A61B 17/12022 606/1 |
| 6,159,206 A | | 12/2000 | Ogawa |
| 7,901,704 B2 | | 3/2011 | Richard |

(Continued)

FOREIGN PATENT DOCUMENTS

| | | |
|---|---|---|
| DE | 19607451 A1 | 9/1997 |
| EP | 743047 A2 | 11/1996 |

(Continued)

OTHER PUBLICATIONS

International Search Report and Written Opinion for PCT/EP2015/071097 dated Apr. 15, 2016.

(Continued)

*Primary Examiner* — Richard G Louis
(74) *Attorney, Agent, or Firm* — Dinsmore & Shohl LLP

(57) ABSTRACT

Provided is a device for delivery into a body lumen having a longitudinally extending stem and a plurality of bristles extending generally radially outwardly from the stem. The device includes at least two different groups or types of bristles.

20 Claims, 51 Drawing Sheets

(56) References Cited

U.S. PATENT DOCUMENTS

| | | | |
|---|---|---|---|
| 8,545,532 | B2 | 10/2013 | Brandeis et al. |
| 8,876,852 | B2 | 11/2014 | Shirley et al. |
| 2002/0161390 | A1 | 10/2002 | Mouw |
| 2003/0015203 | A1* | 1/2003 | Makower ......... A61B 17/12022 128/831 |
| 2004/0034366 | A1 | 2/2004 | Van Der Burg |
| 2005/0004598 | A1 | 1/2005 | White et al. |
| 2005/0043755 | A1 | 2/2005 | Wilson et al. |
| 2005/0085847 | A1* | 4/2005 | Galdonik ............... A61F 2/01 606/200 |
| 2005/0209679 | A1 | 9/2005 | Melsheimer |
| 2006/0116713 | A1* | 6/2006 | Sepetka et al. .............. 606/200 |
| 2006/0167489 | A1 | 7/2006 | Satake et al. |
| 2006/0184194 | A1* | 8/2006 | Pal et al. ...................... 606/200 |
| 2006/0229668 | A1* | 10/2006 | Prestezog ........ A61B 17/12022 606/213 |
| 2006/0287667 | A1* | 12/2006 | Abela ............ A61B 17/320758 606/200 |
| 2007/0135826 | A1 | 6/2007 | Zaver et al. |
| 2007/0142859 | A1* | 6/2007 | Buiser .............. A61B 17/12022 606/200 |
| 2007/0142893 | A1 | 6/2007 | Buiser et al. |
| 2007/0227544 | A1 | 10/2007 | Swann et al. |
| 2007/0270905 | A1* | 11/2007 | Osborne ............ A61B 17/0057 606/213 |
| 2007/0293928 | A1 | 12/2007 | Tomlin |
| 2008/0097374 | A1 | 4/2008 | Korleski et al. |
| 2009/0062838 | A1 | 3/2009 | Brumleve |
| 2010/0094335 | A1 | 4/2010 | Gerberding et al. |
| 2010/0179583 | A1 | 7/2010 | Carpenter et al. |
| 2010/0211087 | A1* | 8/2010 | Osborne ....................... 606/159 |
| 2010/0312321 | A1 | 12/2010 | Kiyosue et al. |
| 2011/0008529 | A1 | 1/2011 | Hossainy et al. |
| 2011/0230810 | A1 | 9/2011 | Raman et al. |
| 2011/0251629 | A1* | 10/2011 | Galdonik ............. A61B 17/221 606/159 |
| 2013/0204234 | A1 | 8/2013 | Cully et al. |
| 2014/0058498 | A1 | 2/2014 | Hannes et al. |
| 2014/0277346 | A1 | 9/2014 | Kanjickal et al. |
| 2016/0166257 | A1 | 6/2016 | Allen et al. |

FOREIGN PATENT DOCUMENTS

| | | |
|---|---|---|
| EP | 0778006 A1 | 6/1997 |
| EP | 882428 A2 | 12/1998 |
| EP | 948935 A1 | 10/1999 |
| EP | 1035808 B1 | 9/2000 |
| EP | 1051116 B1 | 11/2000 |
| EP | 1584298 A1 | 10/2005 |
| EP | 1761178 B1 | 3/2007 |
| EP | 2316355 A1 | 5/2011 |
| EP | 2340785 A1 | 7/2011 |
| EP | 2987464 A1 | 2/2016 |
| EP | 3085310 A1 | 10/2016 |
| JP | 2001079011 A | 3/2001 |
| JP | 2007000572 A | 1/2007 |
| WO | 9306884 A1 | 4/1993 |
| WO | 2001015608 | 3/2001 |
| WO | 0166167 A2 | 9/2001 |
| WO | 2002041753 | 5/2002 |
| WO | 0249536 A2 | 6/2002 |
| WO | 2004069059 A2 | 8/2004 |
| WO | 2005113035 A2 | 12/2005 |
| WO | 2008112435 A2 | 9/2008 |
| WO | 2010098804 A1 | 9/2010 |
| WO | 2010116074 A1 | 10/2010 |
| WO | 2013025493 A1 | 2/2013 |
| WO | 2014140325 A1 | 9/2014 |
| WO | 2014145012 A2 | 9/2014 |

OTHER PUBLICATIONS

Abstract of DE 19607451A published Sep. 4, 1997.
International Preliminary Report on Patentability for PCT/EP2014/055186 dated Sep. 15, 2015.
Examination Report dated Aug. 12, 2019 for NZ Patent Application No. 751704.
Azur, The Technology of Expansion. Terumo Interventional Systems. Downloaded on Feb. 21, 2013 from http://www.terumois.com/products/embolics/AZUR.aspx.
Ekeh et al., Complications arising from splenic artery embolisation: a review of an 11-year experience. The American Journal of Surgery, 205, 250-254, 2013.
Ryer et al. 2013, Comparison of outcomes with coils versus vascular plug embolisation of the internal iliac artery for endovascular aortoiliac aneurysm repair. Journal of Vascular Surgery, vol. 56, Issue 5, Nov. 2012, pp. 1239-1245.
Rastogi et al., Unintended coil migration into the right ventricle during the right ovarian vein coil embolisation. Vascular and Endovascular Surgery, Oct. 2011;45(7).
Marsh et al., Coil Protruding into the Common Femoral Vein Following Pelvic Venous Embolisation. Cardiovascular Interventional Radiology (2008) 31 :435-438.
Beddy et al., Testicular varicoceles. Clinical Radiology (2005) 60, 1248-1255.
Beecroft et al., Percutaneous varicocele embolisation. Canadian Urological Association Journal. Sep. 2007, vol. 1, Issue 3.
Kessel et al., Transcatheter Embolisation and Therapy. Springer ISBN 978-1-84800-896-0. Published 2010.
Balian et al. Pelviperineal venous insufficiency and varicose veins of the lower limbs. Phlebolymphology. 2008;15(1):17-26.
Messé et al., Atrial septal abnormalities (PFO, ASD, and ASA) and risk of cerebral emboli in adults. Downloaded on Feb. 22, 2013 from www.uptodate.com.
St. John Sutton et al., Devices for percutaneous closure of a secundum atrial septal defect. Downloaded on Feb. 22, 2013 from www.uptodate.com.
Letourneau-Guillon et al., Embolisation of Pulmonary Arteriovenous Malformations with Amplatzer Vascular Plugs: Safety and Midterm Effectiveness. Journal of Vascular and Interventional Radiology, vol. 21, Issue 5, pp. 549-656, May 2010.
Wang et al., The Amplatzer Vascular Plug: A Review of the Device and its Clinical Applications, CardioVascular and Interventional Radiology, Aug. 2012, vol. 35, Issue 4, pp. 725-740.
Yoo et al., Preoperative portal vein embolisation using an amplatzer vascular plug. European Radiology (2009) 19: 1054-1061.
Pelage et al. What is Azur Hydrocoil and How Does it Work? Presented at Society of Interventional Radiology, 2011.
Van Der Vleuten et al., Embolisation to treat pelvic congestion syndrome and vulval varicose veins. International Journal of Gynecology and Obstetrics 118 (2012) 227-230.
Bleday et al., Treatment of haemorrhoids, Sep. 24, 2012. Downloaded on Feb. 22, 2013 from www.uptodate.com.
Nyström et al., Randomized clinical trial of symptom control after stapled anopexy or diathermy excision for haemorrhoid prolapse. Br J Surg. 2010;97(2):167.
A M Gardner, Inferior vena caval interruption in the prevention of fatal pulmonary embolism, American Heart Journal (impact factor 4.65). Jul. 1978; 95(6):679-82.
Hollier, MD, Shaggy aorta syndrome and disseminated atheromatous embolisation. In: Bergan JJ, Yao JST, editors Aortic surgery Philadelphia: WB Saunders; 1989. p. 189-194.
Chung EM, Hague JP, Evans DH., Revealing the mechanisms underlying embolic stroke using computational modelling, Phys Med Biol. Dec. 7, 2007;52(23):7153-66. Epub Nov. 19, 2007.
Pyung et al., Successful percutaneous endovascular retrieval of a coil in the left ventricle which migrated during embolisation for pulmonary arteriovenous malformation. International Journal of Cardiology 163 (2013) e33-e35.

* cited by examiner

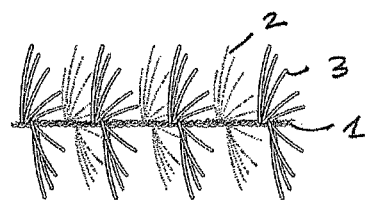
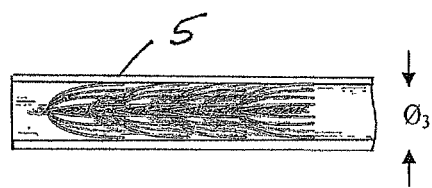
Fig. 1  Fig. 2
Fig. 3
Fig. 4
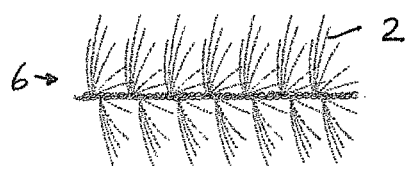
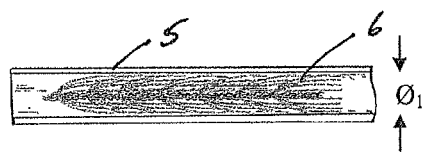
Fig. 5  Fig. 6
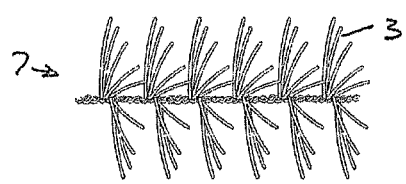
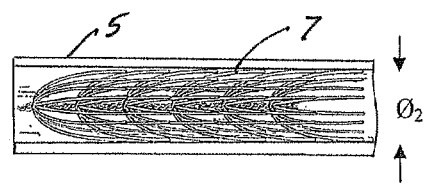
Fig. 7  Fig. 8

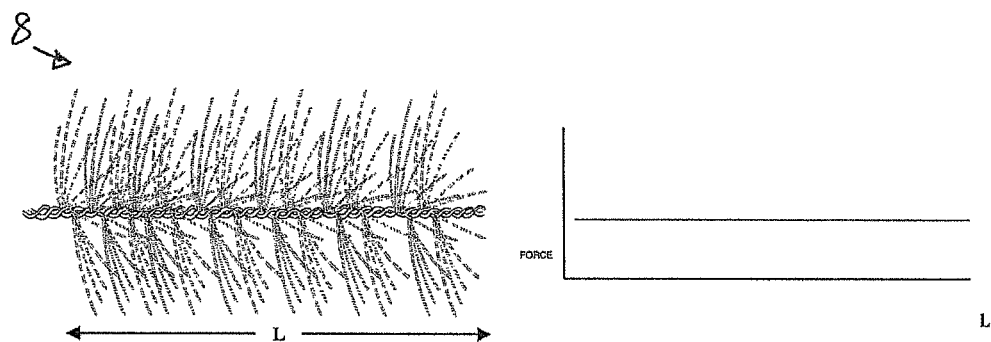
Fig. 9          Fig. 10
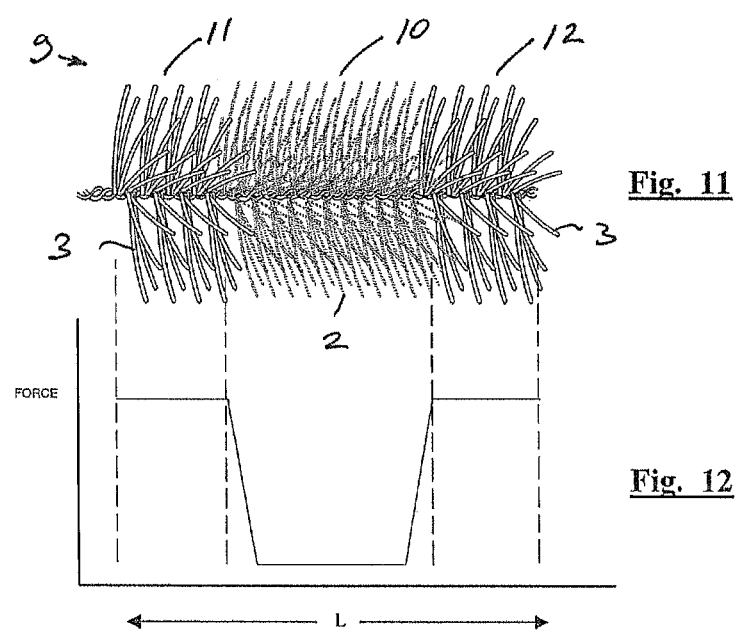
Fig. 11
Fig. 12

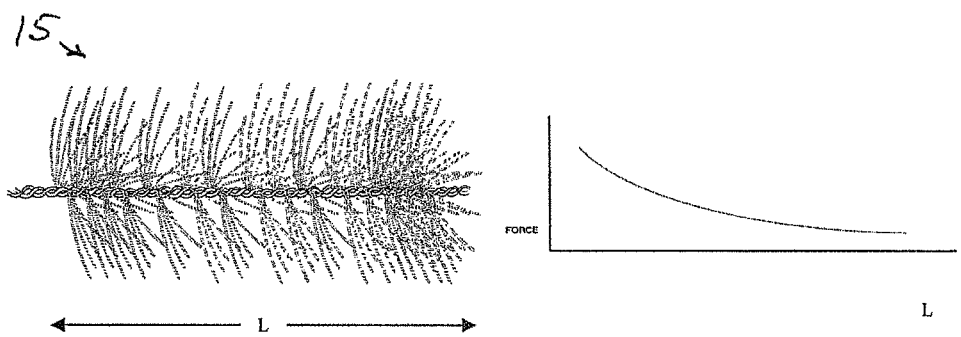
Fig. 13                    Fig. 14
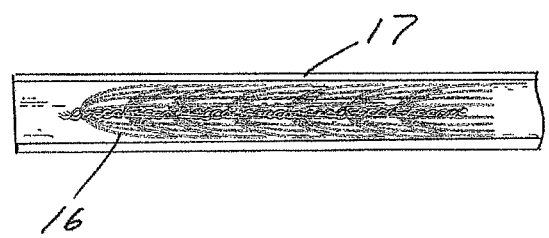
Fig. 16
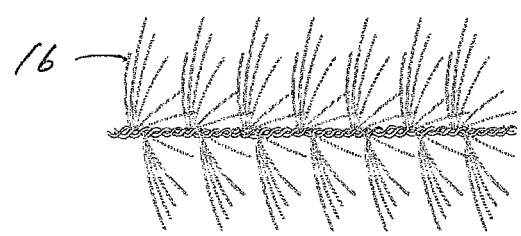
Fig. 15

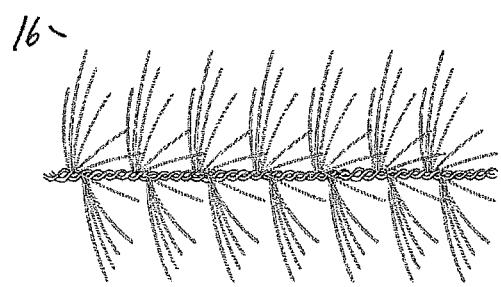
5 minutes     Fig. 17a
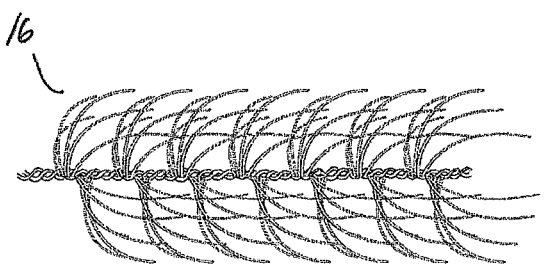
20 minutes     Fig. 17b
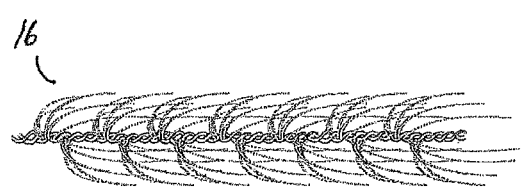
5 days     Fig. 17c (vi)

(vii)

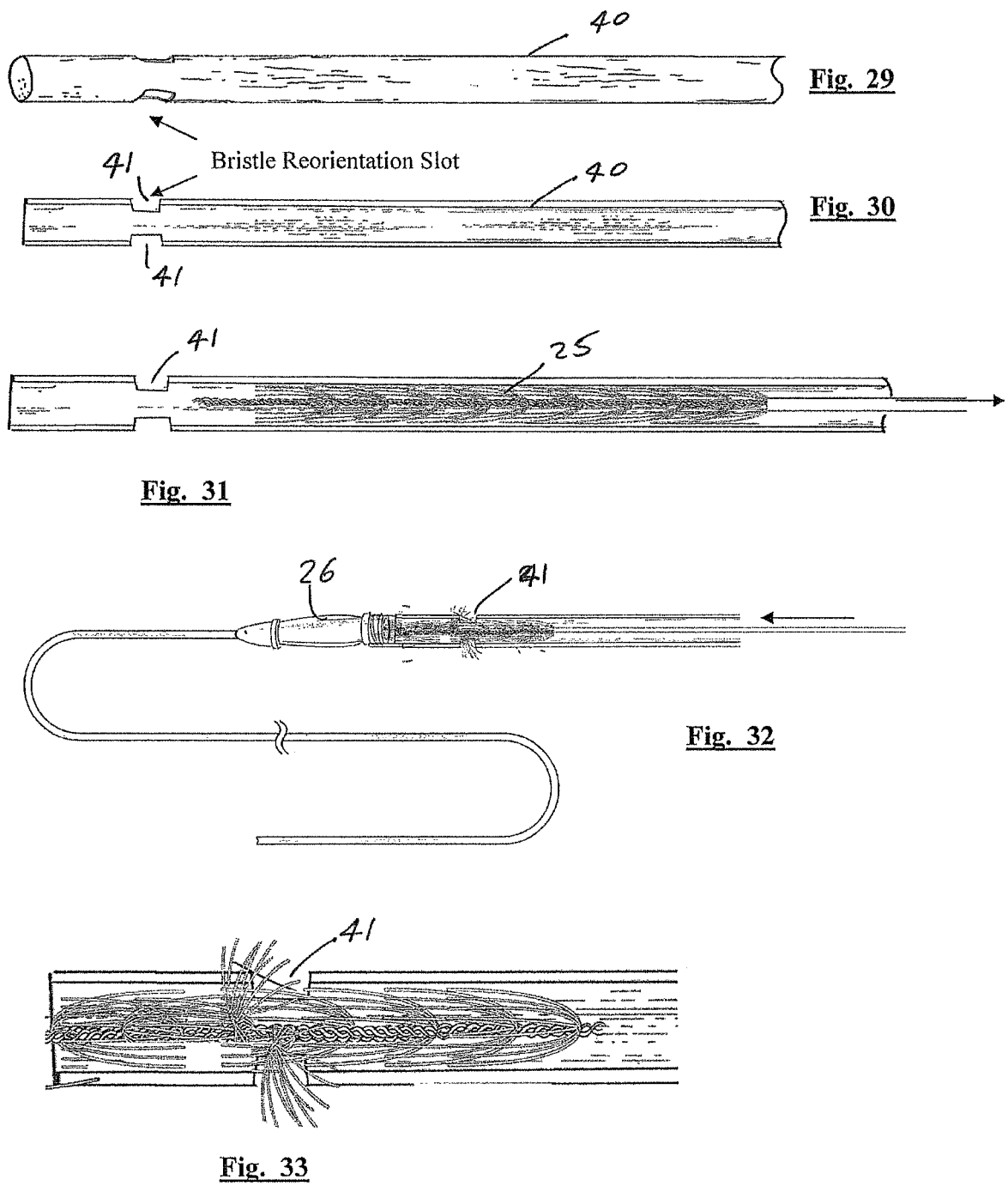

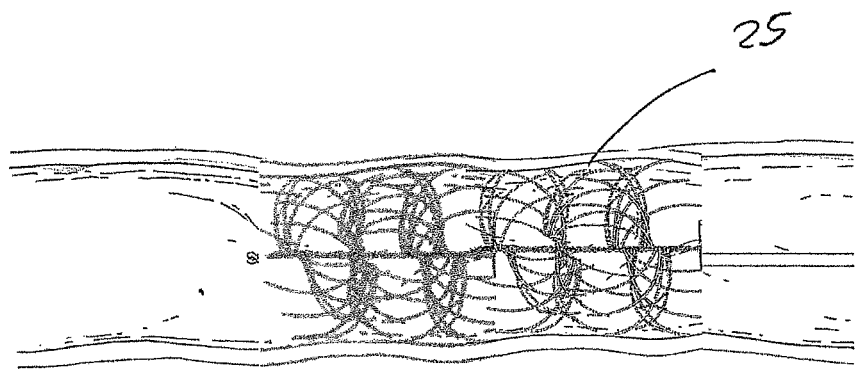
Fig. 34
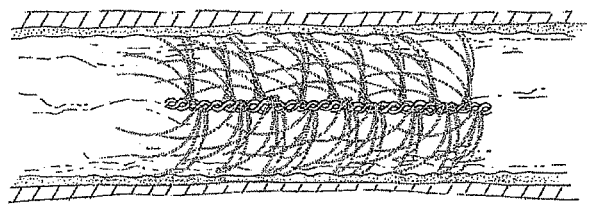
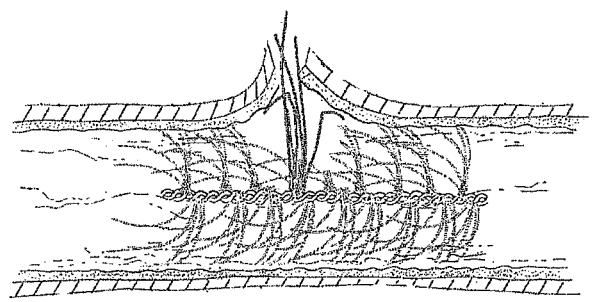
Fig. 35

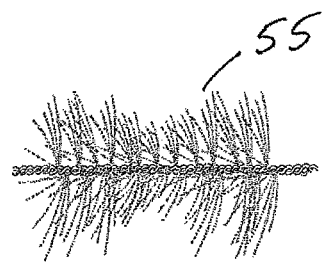 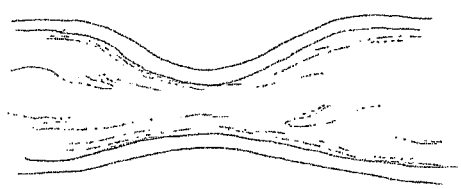
Fig. 37
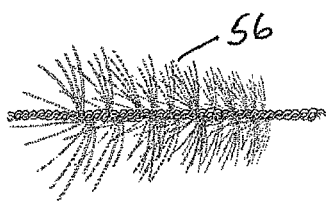 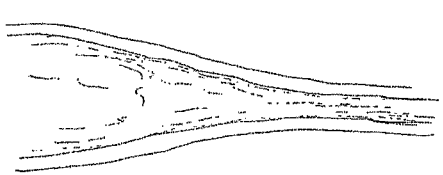
Fig. 38
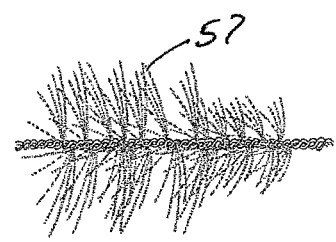 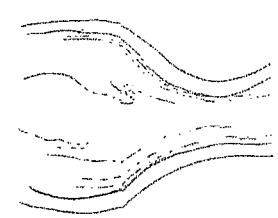
Fig. 39
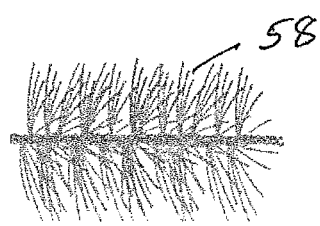
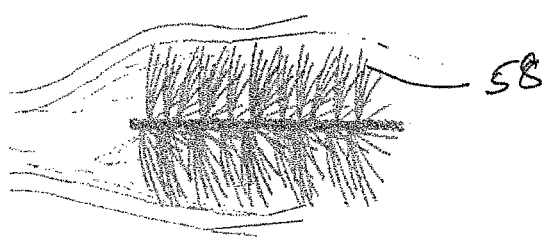
Fig. 40

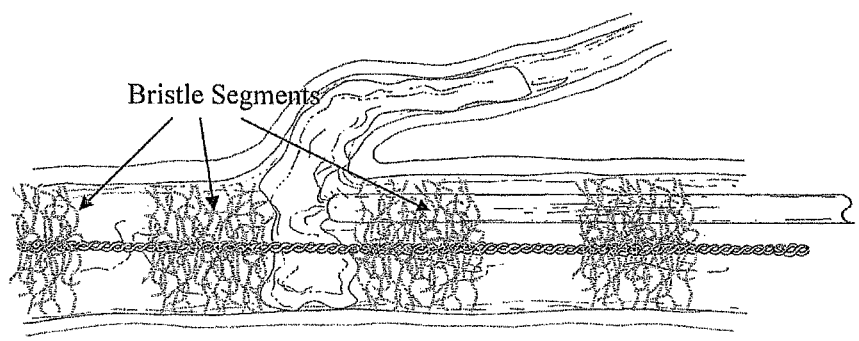
Fig. 70
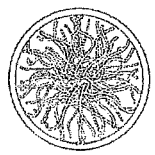
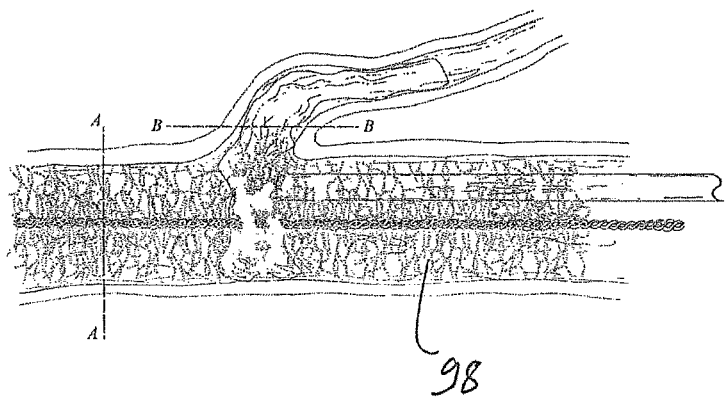
Fig. 71

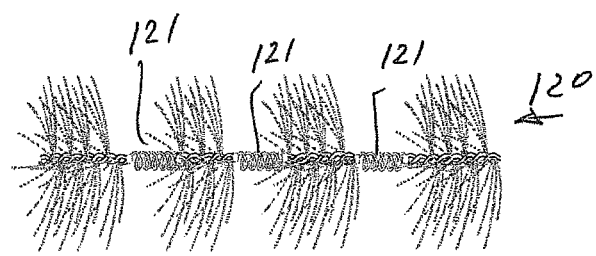
Fig. 86
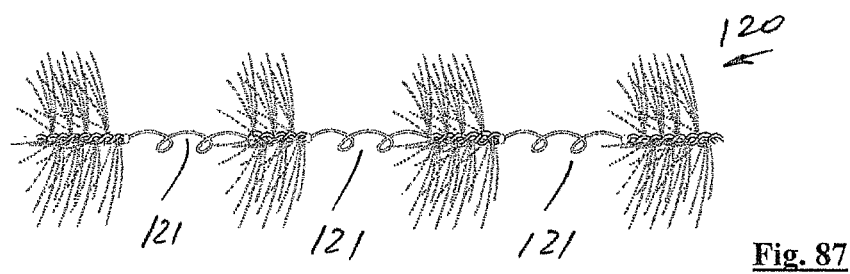
Fig. 87
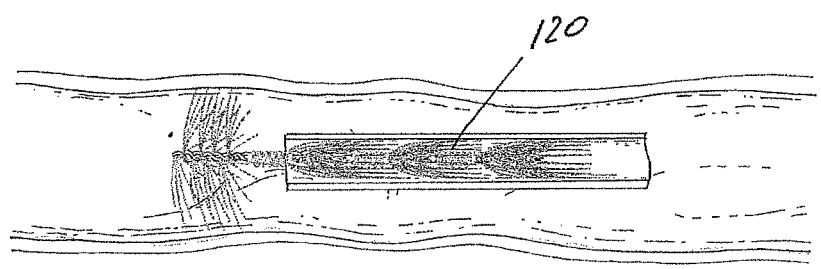
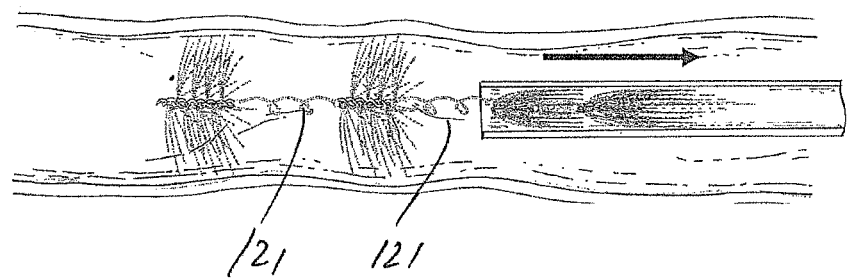
Fig. 88

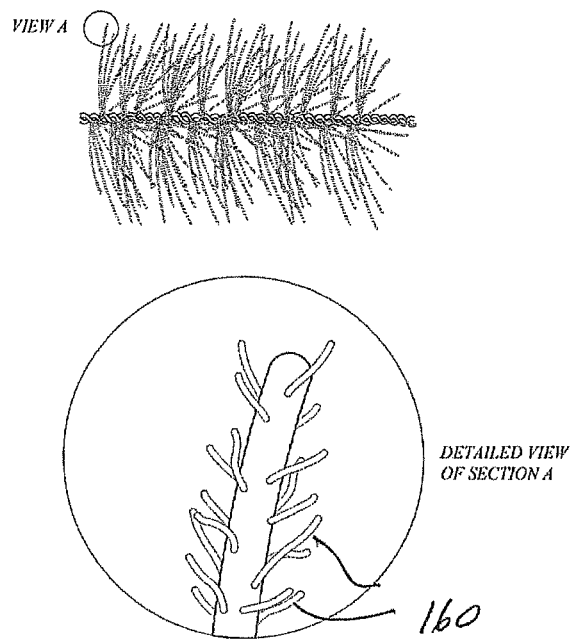
Fig. 95
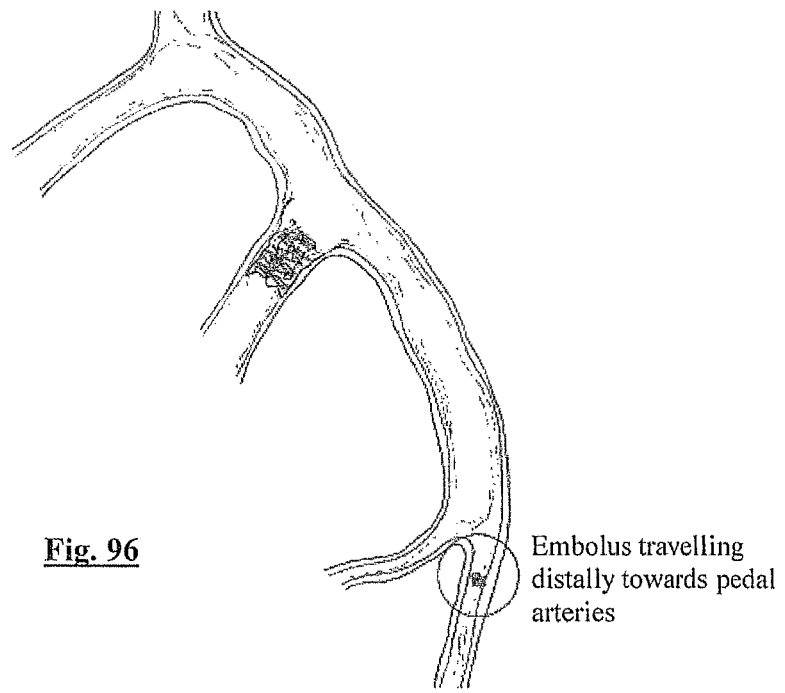
Fig. 96  Embolus travelling distally towards pedal arteries

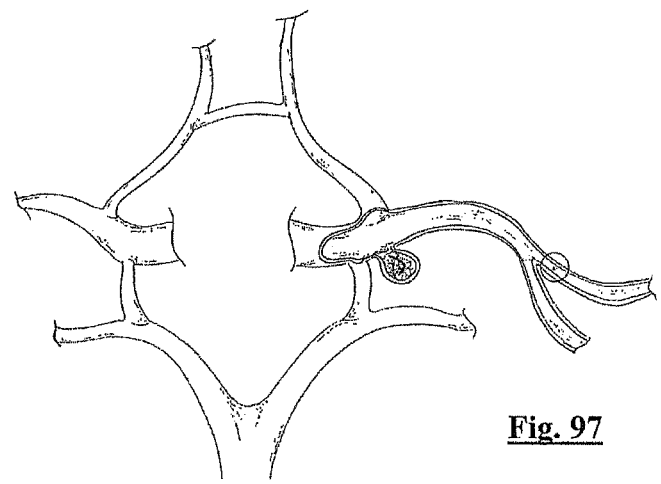
Fig. 97
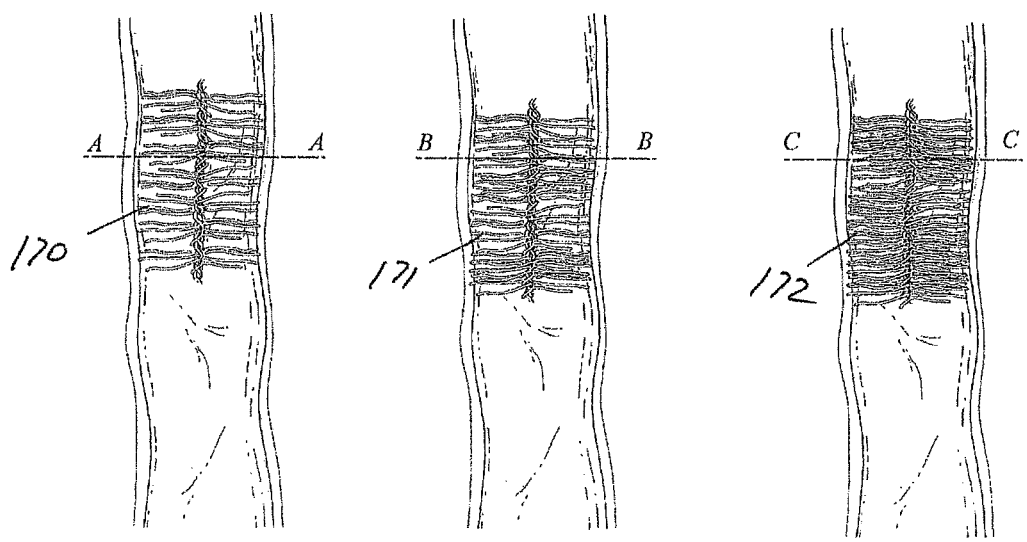
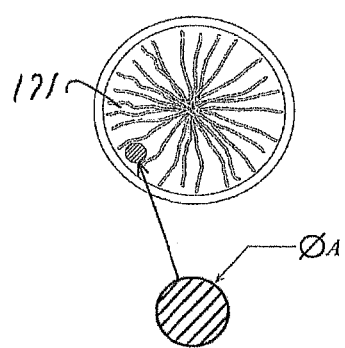
Fig. 98
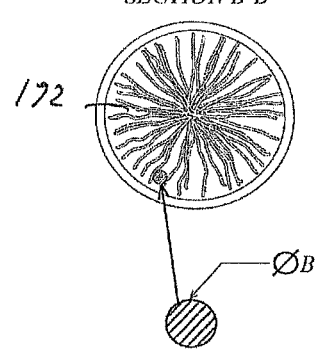
Fig. 99
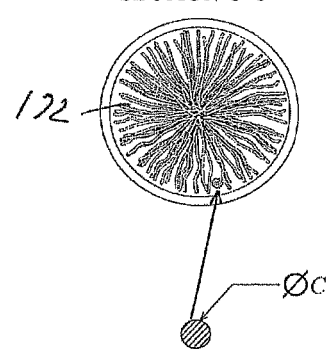
Fig. 100

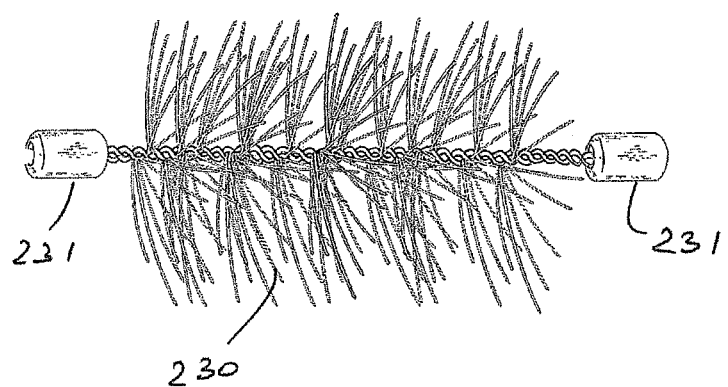
Fig. 108
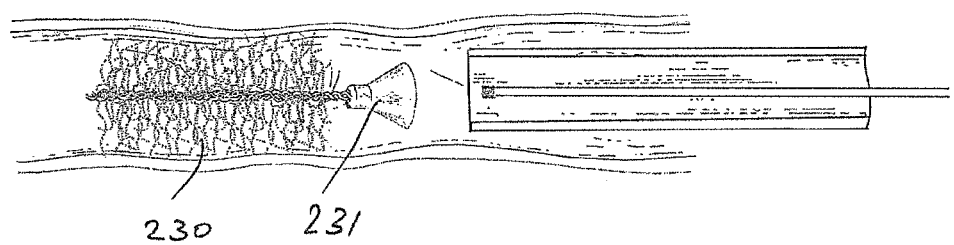
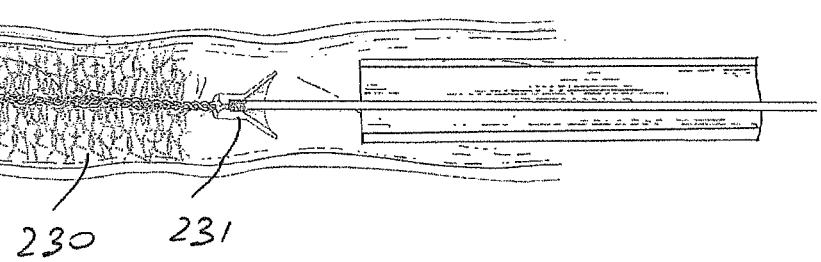
Fig. 109

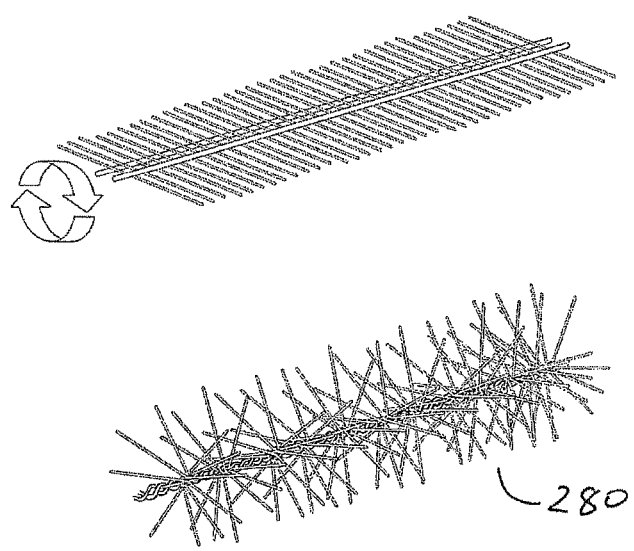
Fig. 113
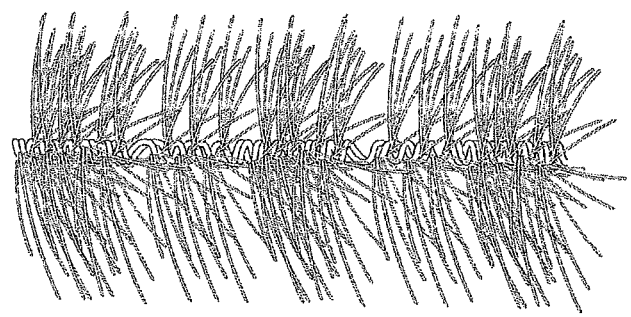
Fig. 114

EMBOLIZATION SYSTEMS

CROSS-REFERENCE TO RELATED APPLICATIONS

This application claims the benefit of priority from U.S. Provisional Application No. 61/787,223, filed on Mar. 15, 2013, the entirety of which is incorporated by reference herein.

FIELD OF THE DISCLOSURE

Embodiments of the present disclosure relate to devices and systems for embolization.

BACKGROUND

Migration of conventional embolization coils occurs 4-14% of transcatheter embolizations [2,3]. Non-target embolization is an outcome of coils migration, the impact of which depends on the final location of the coils. In the venous system, the consequences can be catastrophic with literature indicating that coils can migrate into the renal vein, right atrium of the heart, lung (pulmonary artery). Percutaneous retrieval of the coils is technically very challenging and frequently cannot be attempted as the coils are often entrapped within the organs and tissue.

Coil migration occurs for various reasons:

Technical error: release of a coil or coil pack too distal or proximal to an adjoining larger vessel or plexus [6,7]

High blood flow areas can cause the coil to migrate.

Coil: vessel mismatch. The coils are undersized, hence will not injure the vessel wall, will not induce thrombosis, and are likely to migrate. Or the coils are oversized and will act like a guide-wire and pass further distally into the vessel [8,9].

Vessel dilation: coil migration can occur due to a disparity in the size of coils and dilated vessels, which can change in their diameters depending on vessel hemodynamics [5].

Coils impart a very low radial (anchor) force on the lumen, once a clot forms within the coil, blood flow can force it to migrate.

The profile of the embolization device and delivery system is a critical success factor in successfully accessing target embolization locations e.g. the iliac arteries are frequently tortuous in the presence of abdominal aortic aneurysms [8]. To combat this issue today, microcatheters are often employed in difficult or tortuous anatomy where use of standard catheters may induce spasm and lead to a failed embolization procedure [8]. Additionally different stages in a procedure may require catheters with different mechanical properties e.g. accessing a visceral vessel, particularly in the presence of diseased or tortuous arteries, may require a catheter with a high degree of stiffness and torque control. In general, the lower the profile of the device and delivery system, the greater the accessibility of the device into tortuous and higher order vessels. A lower profile device reduces the diameter of catheter required for delivery and lowers the risks of access site infections, hematomas and lumen spasm.

Dependent on the clinical application of the device, variable anchor forces may be required to prevent migration of the prosthesis e.g. arterial and venous applications have variable blood flow rates and forces. This in turn, will lead to a compromise in terms of profile since larger fibres, which better anchor the bristle device in the lumen, will require a larger catheter for delivery.

The technique generally used to embolise vessels today is to insert a metallic scaffold (coil, plug) into the target vessel, to cause a thrombus that adheres to the scaffold, relying on the thrombus to induce blood cessation and eventually occlude the vessel. In general, available embolization technology does not interfere with or interact with blood flow densely enough across the vessel cross section to induce rapid, permanent vessel occlusion.

Using technology available today, the physician will often have to prolong a specific duration of time for the technology to induce occlusion. In one approach the physician inserts coils and then waits 20 minutes for the coils to expand and cause vessel occlusion [1].

The restoration of the lumen of a blood vessel following thrombotic occlusion by restoration of the channel or by the formation of new channels, is termed recanalisation. Recanalisation can occur due to, coil migration, fragmentation of the embolisation material, and formation of a new vessel lumen that circumvents the occlusion [9]. Recanalization rates vary by procedure and embolic agent, ranging from 10% to portal vein embolization to 15% for pulmonary arteriovenous malformations to 30% for splenic artery embolization [12,14,15]

SUMMARY

Various embodiments of the disclosure may include one or more of the following aspects.

In accordance with one embodiment, there is provided a bristle device for delivery into a body lumen comprising a longitudinally extending stem and a plurality of bristles extending generally radially outwardly from the stem wherein there are at least two different groups or types of bristles.

In one embodiment bristles of one group have a thickness which is different than the thickness of bristles of another group.

In one case one group of bristles is of a different material than the material of another group of bristles.

One group of bristles may be more flexible than another group of bristles.

In one embodiment one group of bristles are interspersed with another group of bristles.

In one case one group of bristles are adapted for anchoring the bristle device in a body lumen. An anchoring group of bristles may be provided at the proximal and/or distal end of the device.

In one embodiment one group of bristles are adapted for occlusion of a lumen. The occlusion group of bristles may be located intermediate the proximal and distal ends of the bristle device.

In one case at least some of the occluding group of bristles are interspersed with the anchoring group of bristles so that the number of occluding bristles increases from the distal end towards the proximal end of the device.

In one embodiment some of the anchoring groups of bristles are interspersed with the occluding group of bristles so that the number of anchoring bristles decreases from the distal end towards the proximal end of the device.

In one case one group of bristles extend radially outwardly to one diameter and another group of bristles extend radially outwardly to another diameter which is different than the diameter of the first group of bristles.

According to a further aspect, one group of bristles are aligned differently than another group of bristles.

At least some of the bristles may be adapted for delivery of a therapeutic agent. The agent delivery bristles may be at least partially coated with a therapeutic agent. Alternatively or additionally at least some of the bristles contain a therapeutic agent. In one case the bristles comprise striations and/or holes for containing a therapeutic agent.

In another aspect the disclosure provides a bristle device loading system comprising:—
- a bristle device for delivery into a body lumen;
- a loading tube; and
- a loading element for loading the bristle device into the loading tube.

In one embodiment the loading element is detachably mountable to the bristle device.

In one case the loading element comprises a loading wire.

The system may comprise a delivery catheter for receiving the bristle device from the loading tube. The loading element may be adapted for loading the bristle device from the loading tube into the delivery catheter. The loading element may also be adapted for deploying the bristle device from the delivery catheter.

In one embodiment the system comprises a taper or a funnel to aid loading of the bristle device into the loading tube and/or the delivery catheter.

In one case the taper or funnel comprises an extension of the loading tube.

In one embodiment the loading tube comprises means for re-orientating at least some of the bristles of the bristle device as the bristle device is passing through the loading tube.

The re-orientation means may comprise at least one hole in the wall of the loading tube through which the bristles may temporarily extend radially outwardly for transition from a first configuration in which the bristles are aligned at a first angle to the longitudinal axis of the loading tube and a second configuration in which the bristles are aligned at a second angle to the longitudinal axis of the loading tube. In one case, in the second configuration the bristles extend generally in an opposite direction to the orientation of the bristles in the first configuration.

The re-orientation means may comprise at least one slot in the wall of the loading tube.

In a further aspect the invention provides a method for loading a bristle device into a delivery catheter comprising the steps of:—
- providing a bristle device, a loading tube and a loading element;
- using the loading element, delivering the bristle device into the loading tube; and
- using the loading element, delivering the bristle device into a delivery catheter.

The method may comprise deploying the bristle device from the delivery catheter using the loading element.

In one case the loading element is releasably mountable to the bristle device and the method comprises mounting the loading element to the bristle device for loading the bristle device into the loading tube and/or for loading the bristle device into the delivery catheter and/or for deploying the bristle device from the delivery catheter, and/or for retrieving a deployed bristle device.

In one case after delivery of the bristle device into the loading tube and/or into the delivery catheter and/or after deployment of the bristle device, the loading element is detached from the loading element.

In one embodiment the loading element is re-attached to the bristle device for retrieval of the bristle device.

The disclosure also provides a bristle device which confirms to a vessel lumen. The bristle device in this embodiment has a larger diameter than the target vessel but the bristles do not deliver sufficient force to perforate the vessel.

The disclosure further provides a bristle device which, when implanted imposes a greater resistance to flow in the axial direction compared to the radial (lateral) direction.

In another aspect the invention provides the use of a bristle device to cause vascular occlusion for the treatment of haemorrhoids.

BRIEF DESCRIPTION OF THE DRAWINGS

The accompanying drawings illustrate certain exemplary embodiments of the present disclosure and, together with the description, serve to explain the principles of the present disclosure. As such, those skilled in the art will appreciate that the conception upon which this disclosure is based may readily be used as a basis for designing other structures, methods, and systems for carrying out the several purposes of the present disclosure. It is important, therefore, to recognize that the claims should be regarded as including such equivalent constructions insofar as they do not depart from the spirit and scope of the present disclosure.

FIG. 1 is an illustration of a bristle device according to the invention with two types of bristles having different diameters;

FIG. 2 illustrates the device of FIG. 1 loaded into a tube;

FIGS. 3 and 4 illustrate bristles of different diameters;

FIGS. 5 to 8 illustrate bristle devices with bristles of different diameters;

FIG. 9 illustrates a bristle device with two types of bristles (dashed, continuous, interspersed and evenly distributed);

FIG. 10 illustrates the uniform anchoring force applied by the device of FIG. 9;

FIG. 11 illustrates a bristle device in which two different types of bristles are used;

FIG. 12 illustrates the variation in the anchoring force applied by the device of FIG. 11;

FIG. 13 illustrates another bristle device with a gradual variation in bristle density;

FIG. 14 is a diagram illustrating the variation in the force applied by the device of FIG. 13;

FIGS. 15 and 16 are illustrations of another bristle device of the invention in collapsed and unconstrained configurations;

FIGS. 17a to 17c illustrate the effect of time in the collapsed condition on unconstrained geometry of a bristle device, when deployed;

FIGS. 29 and 30 show a loading tube with a re-orientation feature according to the invention;

FIGS. 31 to 33 illustrate the loading tube of FIGS. 29, 30, in use;

FIG. 34 shows a bristle device with bristles pointing in opposed directions;

FIG. 35 illustrates vessel perforation by portion of a bristle device;

FIGS. 37 to 39 illustrate alternative bristle devices with geometries to conform with particular vessel shapes;

FIG. 40 illustrates deformation of a vessel by a bristle device;

FIGS. 70 to 72 illustrate the uses of bristle devices;

FIGS. 86 and 87 illustrate a bristle device with length modifying components;

FIG. 88 illustrates deployment of the device of FIGS. 86, 87;

FIG. 95 illustrates a bristle device with microfibers for improved thromogenicity;

FIG. 96 shows an embolus detaching from a bristle device;

FIG. 97 illustrates a bristle device deployed to treat a cerebral aneurysm;

FIGS. 98 to 100 illustrate bristle devices with gaps to limit clot fragments;

FIGS. 107 to 109 show various retrieval systems for retrieving a bristle device;

FIG. 113 illustrates the manufacture of a twisted wire bristle device;

FIG. 114 shows a twisted wire device with varying core wire pitch;

FIGS. 125 and 126 illustrate the use of a bristle device of the invention to treat haemorrhoids

DETAILED DESCRIPTION

Figure 18:
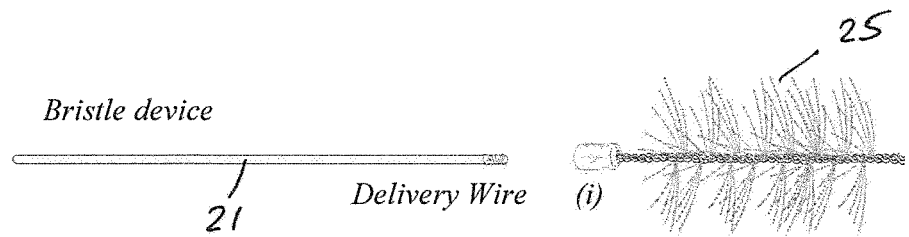
FIGS. 18 to 24 illustrate a bristle device loading system according to the invention in various configurations of use.

Referring to the drawings and initially to FIGS. 1 to 8 thereof there is illustrated a bristle device for delivery into a body lumen. The bristle device comprises a longitudinally extending stem 1 and a plurality of bristles extending generally radially outwardly from the stem. In the invention there are at least two different groups or types of bristles.

In one case a prosthesis with two or more bristle fibre diameters is provided to ensure a low profile for the device when loaded in the catheter 5, and with sufficient anchor force to prevent migration. Smaller diameter fibre bristles 2 are intended primarily to promote and enhance thrombogenicity, while larger diameter fibre bristles 3 are intended primarily to anchor the device in the lumen to prevent migration.

Lumen occlusion occurs due to thrombogenicity of the device, which is a function of its surface area and its ability to cause stasis. For a given volume of fibre material, many small fibres 2 can be more efficiently fitted into a catheter than few larger fibres 3.

Similarly, small fibres 2 are more thrombogenic per unit volume than larger fibres 3; as for a given volume of fibre material, there will be a greater amount of surface area for multiple small diameter fibres, than a few large diameter fibres.

FIGS. 5 and 6 illustrate a bristle device 6 with low diameter fibres 2. This enables the device to be collapsed to a low diameter, $\varnothing_1$. FIGS. 7 and 8 illustrate a prosthesis 7 with larger diameter fibres 3, which will enhance the migration prevention properties of the prosthesis. The collapsed diameter, $\varnothing_2$, of this prosthesis is larger than $\varnothing_1$.

The bristle device of FIGS. 1 and 2 has a combination of both low and high diameter fibres 2, 3. This enables a compromise in profile to a diameter, $\varnothing_3$, where $\varnothing_1 < \varnothing_3 < \varnothing_2$. This approach provides good migration prevention properties (from large diameter fibres 3) combined with good thrombogenicity and low profile (from the smaller diameter fibres 2).

The different bristle types can be of the same or different materials. More than one bristle material could also be used instead of, or in combination with more than one bristle diameter.

FIG. 9 illustrates another bristle device 8 according to the invention which in this case has two different types of bristle interspersed and generally equally distributed along the length of the device. The different types of bristles may be distinguished by their dimensions or material, each contributing separately in terms of anchor force and occlusion. Because of the equal distribution, the anchor force is uniformly distributed along the bristle device length as illustrated in FIG. 10.

Various alternative arrangements of different types or groups of bristles may be provided.

For example, FIGS. 11 and 12 illustrate a bristle device 9, of length L, in which two different types of bristle are used: one for the middle section 10 and one for the ends 11, 12. In this case, the bristles at the ends of the device have a higher diameter. These bristles are intended to anchor the prosthesis within the lumen. The middle section contains a higher density of bristles with a lower diameter, and is intended to cause more interference with blood flow along with more surface contact with the blood and consequently, occlusion of the lumen.

FIG. 13 illustrates a bristle device 15, which has two different types of bristle. In this case the bristles with better properties for anchoring the device in the lumen are more densely located on the left hand side of the bristle device and taper off towards the right hand side of the device where the density of the bristles of the second type of bristles is higher. This would be advantageous in a high flow scenario requiring extremely large number of small diameter bristles to cause occlusion. By having the anchoring bristles at the end only, the other end could contain the extremely high number of lower diameter bristles required to cause occlusion, without compromising profile. Because of the distribution, the anchor force is distributed along the bristle device length as illustrated in FIG. 14.

A bristle device 16 when manufactured has an unconstrained geometry as illustrated in FIG. 15, which is the desired shape. In order to be delivered through a catheter the bristle device must spend some time in a collapsed condition in a catheter 17 as illustrated in FIG. 16.

Storage of a device in a collapsed condition can lead to shape-setting of a bristle device, particularly if the bristles are constructed from a polymer. Specifically, once the bristle device is deployed from the catheter it may not return fully to its original shape. Shape-setting refers to any change in shape, which is caused due to storage a catheter for a prolonged period. In general, the longer the period of storage the greater the degree of shape setting is likely to be. This is shown schematically in FIGS. 17a to 17c.

To counteract this problem, in the invention a loading system is provided. The loading system comprises a loading tube 20. The purpose of the loading tube 20 is to allow the clinician to collapse a bristle device 25 for delivery through a delivery catheter 26 immediately before for (temporary or permanent) implantation in a lumen. In this way the bristle device 25 will not spend a substantial amount of time in the collapsed condition, minimising the potential for shape setting. The loading system also comprises a loading element such as a wire 21 for loading the bristle device 25 into the loading tube 20.

Figure 19:
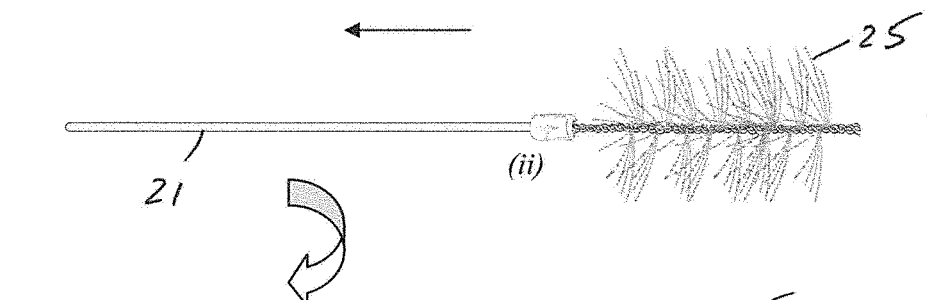
Figure 20:
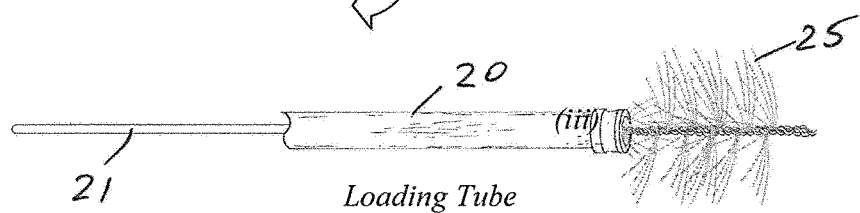
Figure 21:
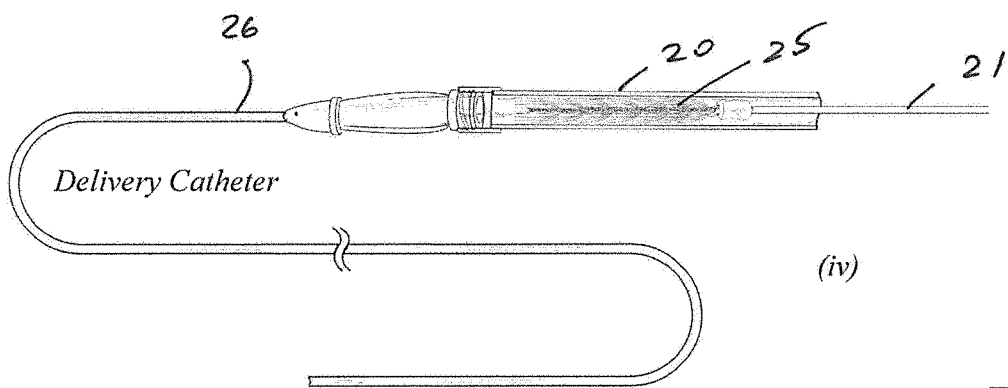
Figure 22:
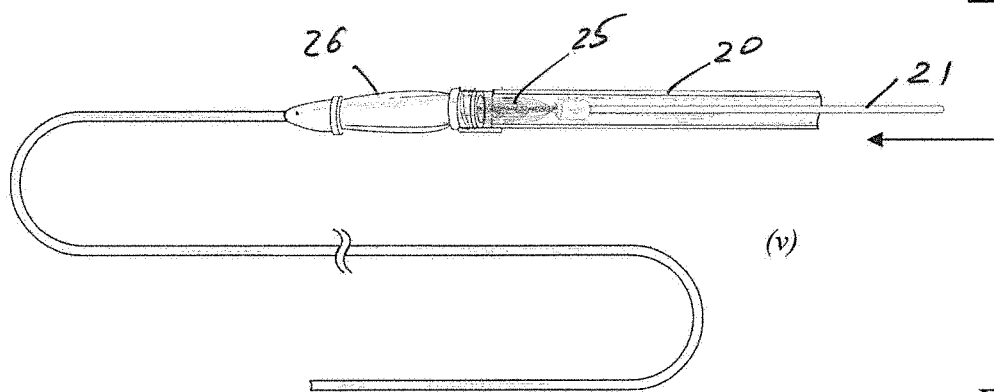
Figure 23:
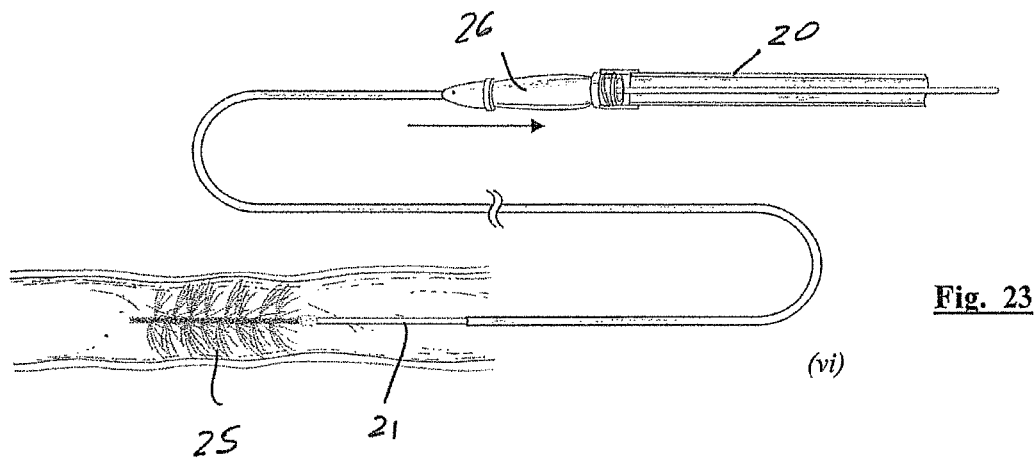
Figure 24:
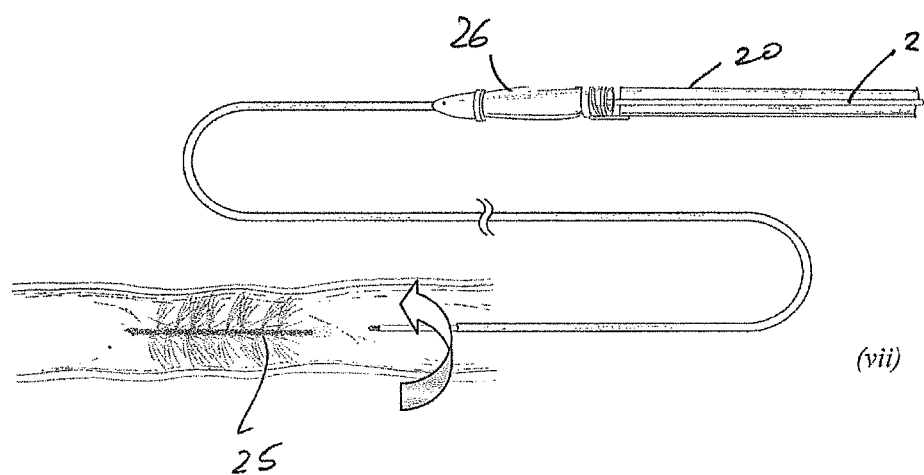

The bristle device can be delivered through any suitable delivery catheter 26. The steps for use of the loading system are as follows:

i. Bring bristle device 25 and delivery wire 21 in contact (FIG. 18)
ii. Screw the delivery wire 21 into the prosthesis 25 (FIG. 19)
iii. Using the delivery wire 21, pull the bristle device 25 into the loading tube 20 (FIG. 20)
iv. Connect the loading tube 20 to a delivery catheter 26 (FIG. 21)
v. Push the bristle device 25 into the delivery catheter 26 using the delivery wire 21 (FIG. 22)
vi. Once the tip of the bristle device 25 is at the tip of the catheter 26 (located at the distal point of the vessel intended for implantation), holding the delivery wire 21 still, retract the delivery catheter 26 to deploy the bristle device 25 (FIG. 23)
vii. Once satisfied with the position of the device 25, unscrew the delivery wire 21 from the bristle device 25 to detach (FIG. 24)

Figure 25:
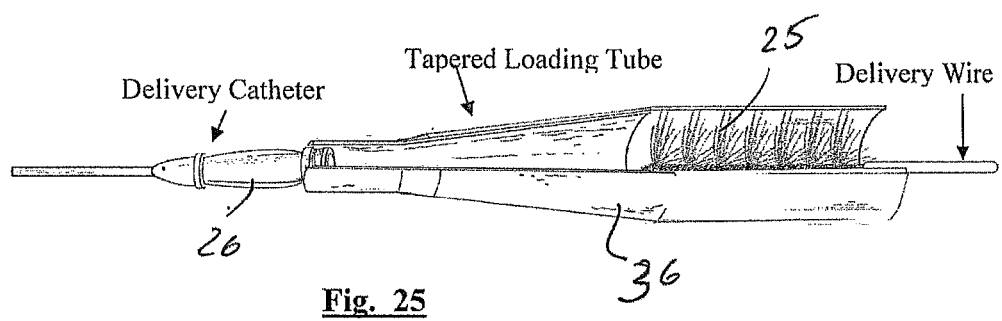
FIGS. 25 and 26 illustrate a tapered loading tube.
Figure 26:
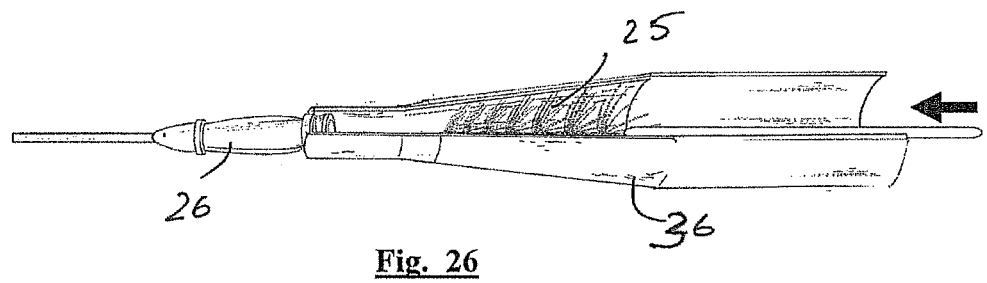

Referring to FIGS. 25 and 26, in another embodiment, a loading tube 36 of tapered geometry will allow the user to crimp down the bristle device 25 to the collapsed state as it is pushed via the delivery wire into the catheter for delivery to a vessel.

Figure 27:
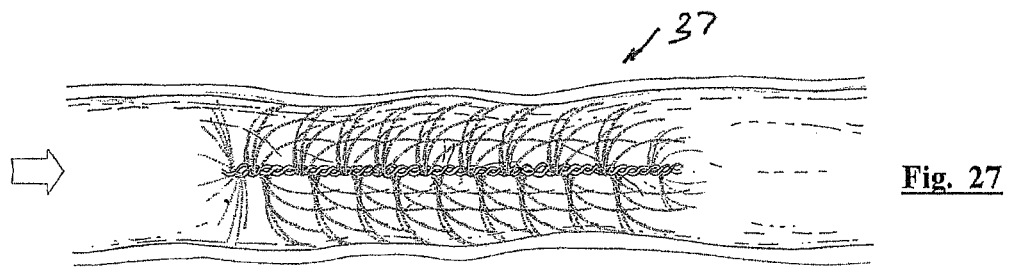
FIGS. 27 and 28 illustrate differing bristle orientations with respect to flow.
Figure 28:
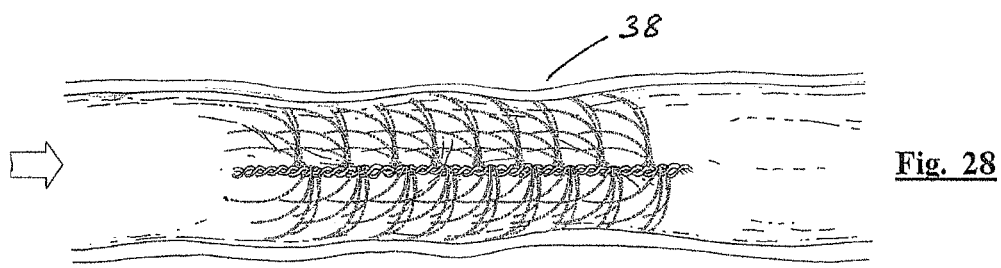

Referring now to FIG. 27 there is illustrated a bristle device 37 with a diameter larger than the lumen, deployed such that the bristles point along the direction of flow within the lumen. FIG. 28 shows a schematic in which a prosthesis 38 is deployed with the bristles pointing the opposite direction of the flow.

The force of the flow against the prosthesis could cause it to migrate. If the direction of flow (force) is opposite to the direction in which the bristles point along the lumen, the force required to move the device will be smaller than the case in which the direction of the flow (force) is the same as the direction along which the bristles point in the lumen. This is due to the interaction of the tips of the bristles with the vessel wall and the resulting friction—the tips of the bristles help anchor the prosthesis in the lumen if any movement of the device begins to occur.

As the direction of action of the flow may not always be predictable, it may be preferable to ensure that, when deployed, the bristle device has some bristles oriented in one direction, and other bristles oriented in the opposite direction. A physician may wish to use different approaches to deploy the device, which may or may not lead to a desirable bristle direction with respect to the flow direction.

When a bristle device is pulled into a loading tube 20 to be pushed into a delivery catheter 26, its bristles are aligned within the loading tube such that they point distally when in the catheter. This means that all bristles will point one direction when the prosthesis is deployed. As explained above, this means that the device will have lower force to migration in one direction than the other.

In one embodiment of the invention a loading tube is provided which is configured to reorient at least some of the bristles while the bristle device is being pushed into the delivery catheter.

Referring to FIGS. 29 to 34 in one case a loading tube 40 contains reorientation slots 41 which allow the bristles to spring out while the bristle device 25 is being pushed into the delivery catheter 26. Subsequently, as these bristles encounter the end of the slot 41 while the device is being pushed into the delivery catheter 26, they are forced to collapse and realign, pointing in the opposite direction to the direction they had originally pointed.

The loading tube may be adapted to include a means to open or close the hole depending on the wishes of the physician to change or not change the orientation of the bristles.

Ideally an embolization device should interact with the entire surface area of the target lumen. This has multiple benefits:

Assists denudation of the endothelium of the lumen wall, which is known to aid in lumen embolisation.

Occludes the lumen along its entire length and cross sectional area thereby preventing recanalization via a collateral or side-branch into the target lumen.

Leads to a permanent occlusion thus reducing the risk of surgical failure and the requirement for a repeat procedure.

Greater interaction with the vessel wall helps lock the implant in position thereby reducing the risk of implant migration.

Removing or damaging the endothelium has a critical role to play in the clotting cascade within a lumen. When the endothelium is removed, the normally isolated, underlying collagen is exposed to circulating platelets, which bind directly to collagen, which is released from the endothelium and from platelets; leading to the formation of a thrombus. If the device does not provide adequate lumen conformance and coverage then recanalization can occur. This coverage should be maximised not only in terms of vessel cross section but also vessel wall area also. In spermatic vein occlusion, a liquid (e.g. sclerosant, which has greater lumen conformance and coverage capabilities than coils) results in higher technical success and lower recanalization rates than coils alone [8]. However, damage to the endothelium should be done without causing vessel perforation. This could lead to catastrophic events such as internal bleeding. This is shown schematically in FIG. 35.

In another aspect of the invention a bristle device is provided which has a larger unconstrained diameter than the target vessel and which incorporates bristles which are flexible enough to conform to the vessel anatomy and which will not cause vessel perforation i.e. delivery force to the vessel wall is not sufficient to perforate.

Figure 36:
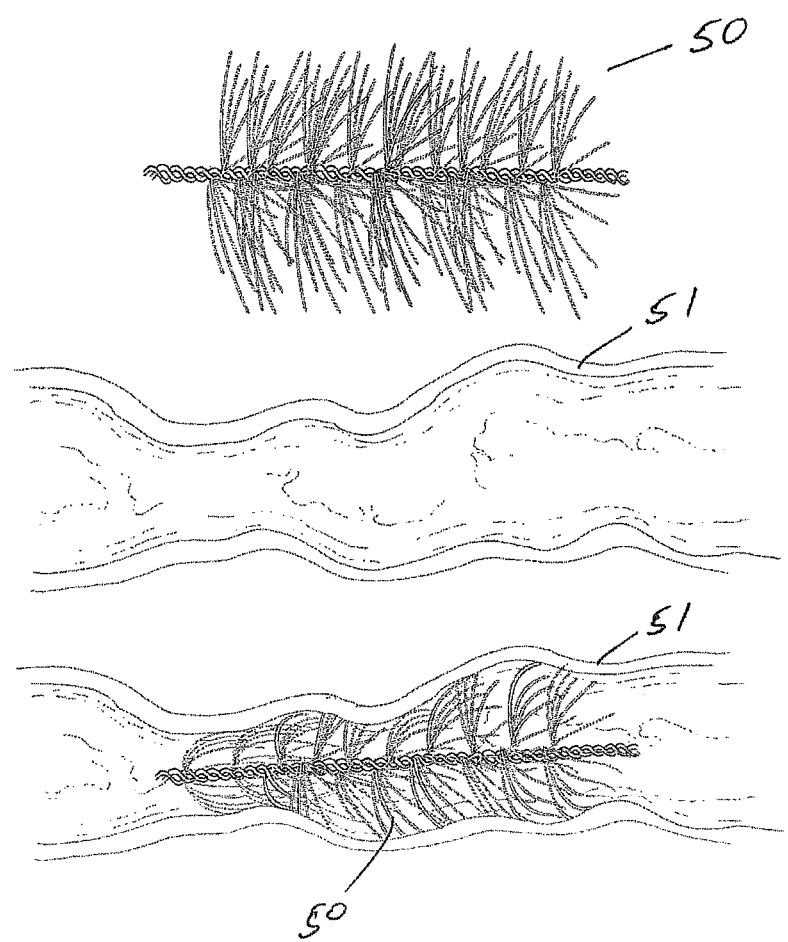
FIG. 36 illustrates a bristle device with flexible fibres for vessel conformance.

FIG. 36 shows a prosthesis 50 for deployment in a lumen 51 with a varying lumen diameter. When deployed in a lumen with a varying diameter, the device can conform to the variations in the lumen diameter without causing lumen perforation. This is due to the flexibility of the fibres of the prosthesis which, while providing an anchor within the lumen, are not too stiff to perforate the lumen.

The potential for the fibres to perforate the vessel is dependent primarily on the fibre material, fibre diameter and the surface area of contact between the fibre and the vessel wall. A fibre with a low stiffness may have the potential to perforate the vessel if its stiffness is high enough due to a large diameter (and potentially a sharp bristle tip).

The fibres may be of a radiopaque material to enable the physician to visualise the device using x-ray.

| Material | Diameter Less Than: |
| --- | --- |
| Nitinol | <0.015 |
| Platinum | <0.015 |
| Stainless Steel | <0.015 |
| Polyester | <0.015 |
| PTFE | <0.01 |
| Nylon (Polyamide) | <0.015 |
| Polypropylene | <0.015 |
| PEEK | <0.015 |

-continued

| Material | Diameter Less Than: |
| --- | --- |
| Polyimide | <0.015 |
| Pebax | <0.015 |
| Polyurethane | <0.015 |
| Silicone | <0.015 |
| FEP | <0.015 |
| Polyolefin | <0.015 |

FIGS. 37 to 39 illustrate various embodiments in which lumens with non-uniform diameters may be treated using a prosthesis which has conforming geometries. FIG. 37 shows a "dog-bone" shaped prosthesis 55. FIG. 38 shows a tapered prosthesis 56 suitable for a tapered lumen. FIG. 39 shows a prosthesis 57 suitable for a lumen with a step-change in diameter.

Referring to FIG. 40 in another embodiment a bristle device 58 in which at least some of the bristles are stiffer and impose the geometry of the bristle device on the vessel wall. This occurs because the diameter of the bristle device is larger than that of the target vessel.

A Method to Treat Haemorrhoids

Background

Hemorrhoids, often described as "varicose veins of the anus and rectum," are a common condition in which the veins lining the anus or lower rectum become swollen and inflamed.

Hemorrhoids are varicosities of the hemorrhoidal plexus (rectal venous plexus). This plexus communicates with the uterovaginal plexus and drains, via the rectal veins, into the internal pudendal vein and internal iliac vein. Although the exact cause of hemorrhoids remains unknown, standing too long in an upright position exerts pressure on the rectal veins, which often causes them to bulge.

There are two types of hemorrhoids: external and internal, which refer to their location. External hemorrhoids develop under the skin around the anus; if a blood clot develops in one of them (in a condition known as thrombosed external hemorrhoids), a painful swelling may occur. External hemorrhoids are characteristically hard and sensitive, and bleed upon rupture. Internal hemorrhoids are sac-like protrusions that develop inside the rectal canal. Painless bleeding and protrusion during bowel movements are the most common symptoms of internal hemorrhoids; however, they may cause severe pain if they become completely prolapsed, or protrude from the anal opening.

Hemorrhoidectomy, the surgical removal of hemorrhoids, is recommended for third- and fourth-degree internal hemorrhoids (with or without external hemorrhoids). The two major types of hemorrhoidectomy operations are the closed (Ferguson) hemorrhoidectomy and the open (Milligan-Morgan) hemorrhoidectomy. Both techniques are performed using a variety of surgical devices, including surgical scalpel, monopolar cauterization, bipolar energy, and ultrasonic devices.

Complications associated with Hemorrhoidectomy include [17]:

Urinary retention following hemorrhoidectomy is observed in as many as 30 percent of patients Urinary tract infection develops in approximately 5 percent of patients after anorectal surgery Delayed hemorrhage, probably due to sloughing of the primary clot, develops in 1 to 2 percent of patients; it usually occurs 7 to 16 days postoperatively. No specific treatment is effective for preventing this complication, which usually requires a return to the operating room for suture ligation.

Fecal impaction after a hemorrhoidectomy is associated with postoperative pain and opiate use. Most surgeons recommend stimulant laxatives, stool softeners, and bulk fiber to prevent this problem. Should impaction develop, manual disimpaction with anesthesia may be required.

An alternative to hemorrhoidectomy is stapled hemorrhoidopexy, in which an intraluminal circular stapling device resects and resets the internal hemorrhoid tissues. When the stapler is fired, it creates a circular fixation of all tissues within the purse string to the rectal wall. In effect, it will draw up and suspend the prolapsed internal hemorrhoid tissue.

This procedure is best utilized when offered to patients with significant prolapse, such as those with grade II, grade III, or IV internal hemorrhoids. This procedure does not effectively treat most external hemorrhoids, and often requires separate excision of the external component when performed on patients with combined disease.

Neither procedure is effective at inducing long-term relief. In a randomized trial of stapled hemorrhoidopexy versus hemorrhoidectomy, the procedures were equally effective in preventing recurrence after one year [18]. Patients undergoing hemorrhoidectomy were more likely to have symptomatic relief from the hemorrhoids (69 versus 44 percent with hemorrhoidopexy), but had significantly greater postoperative pain [18].

It has been demonstrated that embolization of the internal iliac veins removes reflux from hemorrhoidal plexus. Some dimishment and/or disappearance of hemorrhoids has been associated with embolisation of refluxing pelvic and internal iliac veins (16). Technical success of embolization of the internal iliac or hypogastric veins has been reported to be 85% [9,10].

In the clinical literature, caution has been advised when embolizing the internal iliac vein tributaries where there is clinically significant communication with veins of the lower limb; as this communication between the obturator and the common femoral veins increases the risk of coil migration and displacement into a deep vein [5]. Displacement into a deep vein can have serious consequences if the coil led to a deep vein thrombosis [5]. Accordingly, a safe and effective device is still required for embolisation of the internal iliac veins for the treatment of hemorrhiods.

In one aspect of the invention a method for the treatment of haemorrhoids is proposed in which a bristle device is implanted in the internal iliac, or hemorrhoidal veins to cause permanent occlusion. This occlusion will prevent venous reflux to the hemorrhoidal plexus, which causes hemorrhoids.

Figure 125:
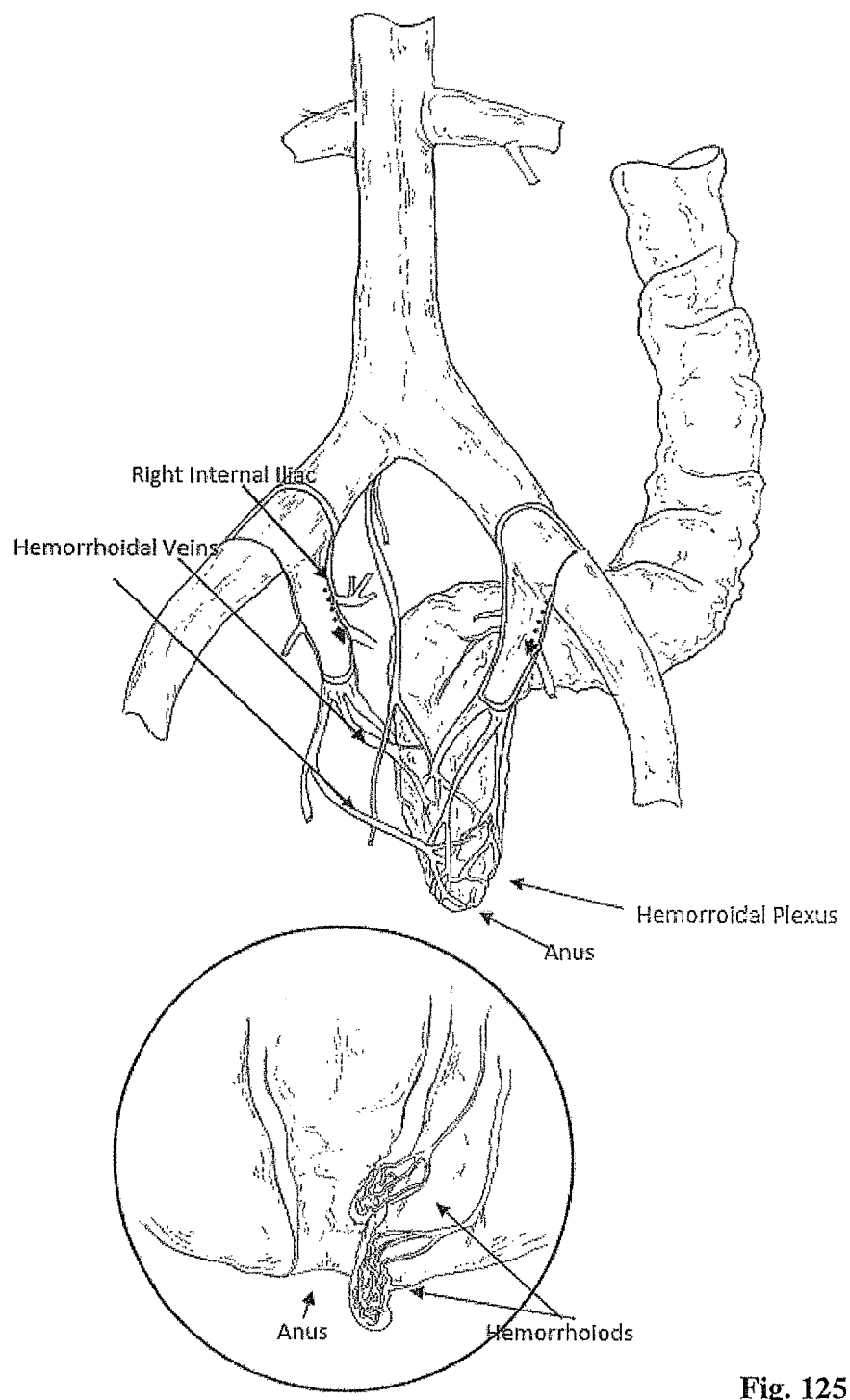

FIG. 125 is a schematic showing the venous anatomy relating to the presence of a haemorrhoid (detailed view of cross section of anus). The broken arrows show direction of venous reflux through internal iliac veins leading to varicosities off the haemorrhoidal plexus, causing haemorrhoids.

Figure 126:
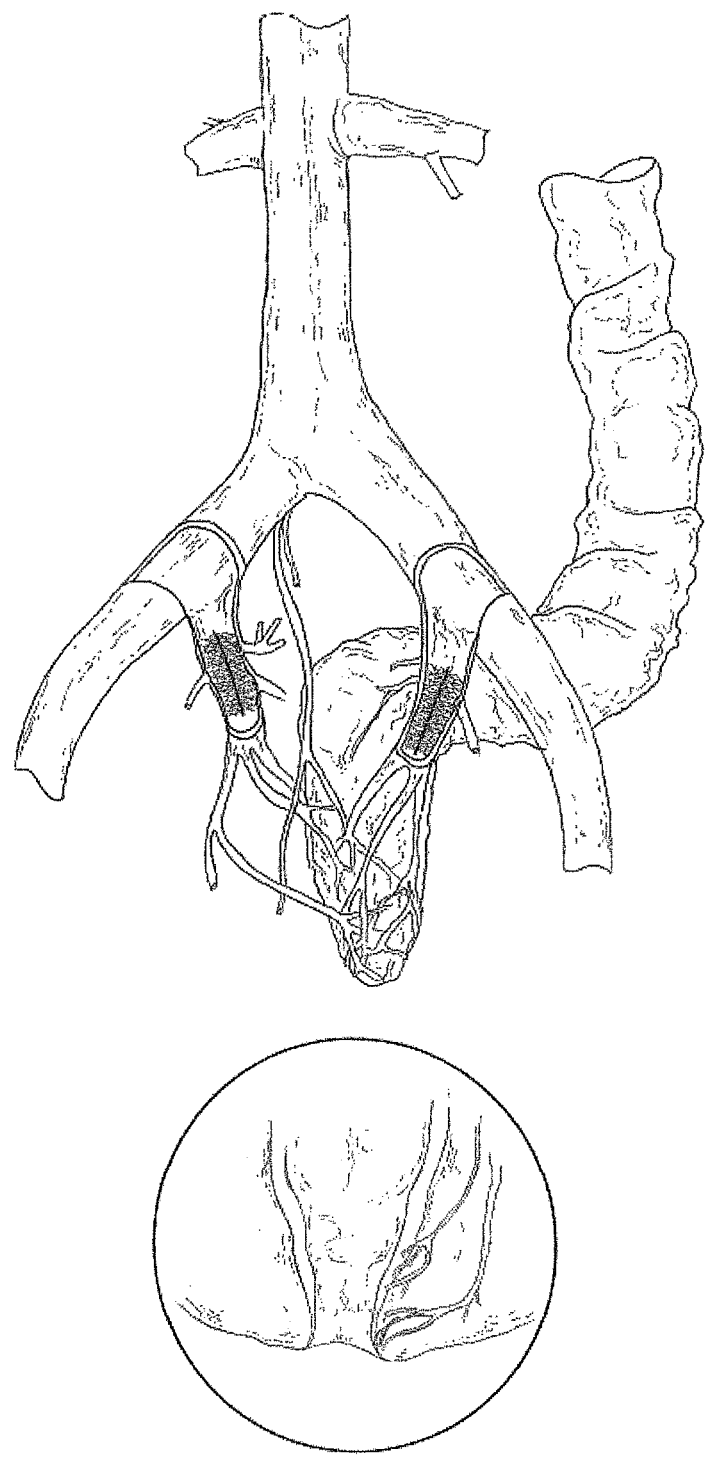

FIG. 126 illustrates the insertion of bristle devices in internal iliac veins has arrested refluxing flow to the haemorrhoidal veins and caused the haemorrhoid to disappear.

Figure 41:
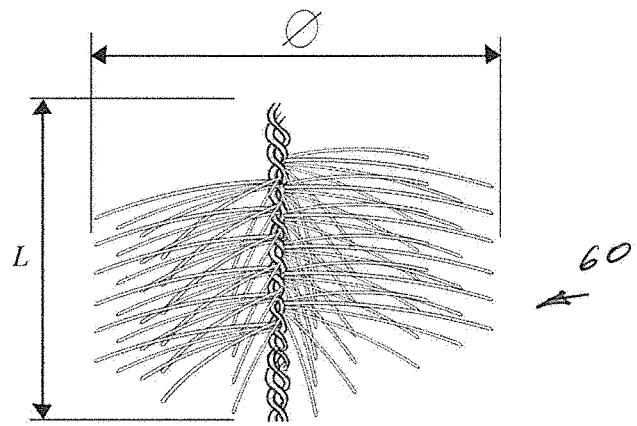
FIG. 41 illustrates a bristle device with length and diameter attributed.

FIG. 41 shows a bristle device 60 with a length, L, and a diameter, ø. The stability of the device during and after deployment from a catheter is dependent upon the ratio of these quantities with respect to the vessel diameter. Ideally, the bristle device should have a diameter greater than or equal to the target lumen, and a length to diameter ration, L/ø, of 1.0 or greater.

Figure 42:
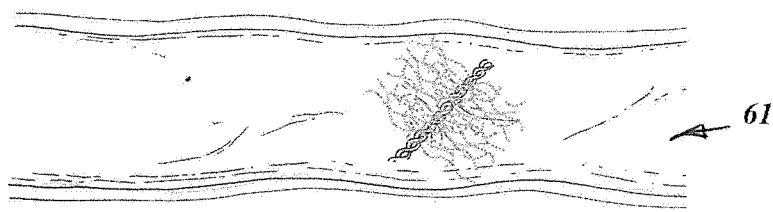
FIG. 42 shows the negative effect of a low length to diameter ratio.

FIG. 42 shows a bristle device 61 with a ratio L/ø<1 deployed in a lumen. The prosthesis has become unstable during, or after, deployment and consequently now lies at an angle to the long axis of the lumen. Due to a L/ø ratio<1 the device could migrate, recanalise or damage the lumen wall. The low length to diameter ratio also means that the prosthesis could "pop" out of the catheter making it difficult to deploy accurately to the target site.

Figure 43:
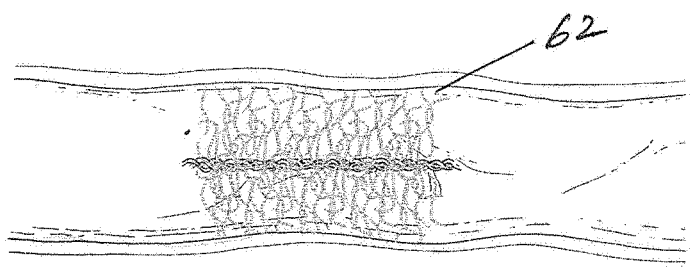
FIG. 43 illustrates a bristle device with a high length to diameter ratio.

FIG. 43 shows a bristle device 62 according to the invention with L/ø>1.0. In this case the prosthesis is correctly aligned, is stable and is unlikely to migrate or cause damage to the lumen wall.

Figure 44:
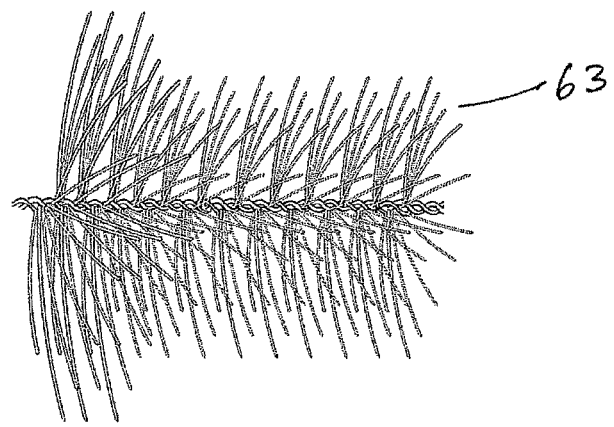
FIG. 44 illustrates a bristle device with distal anchoring fibres.
Figure 45:
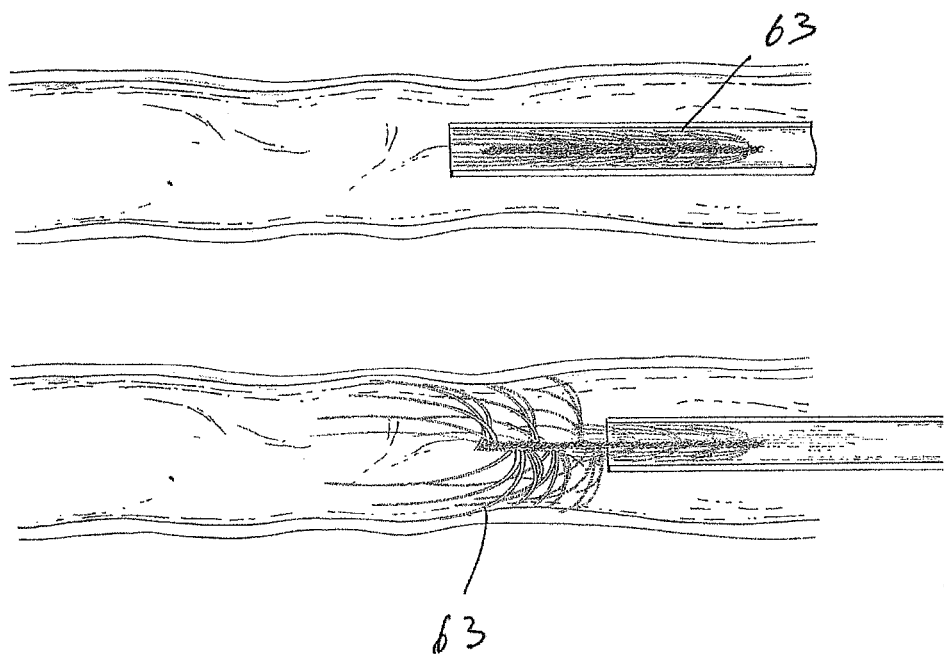
FIG. 45 shows the use of longer bristles at the ends acting as stabilisers.

Referring now to FIGS. 44 and 45 in this case a bristle device 63 has longer bristles at the distal end (the end which will be deployed first from the catheter). These longer bristles are intended to act as "stabilisers" upon initial partial deployment of the prosthesis. The longer bristles extend distally along the vessel wall providing and anchor, ensuring the prosthesis cannot "pop" forward from delivery catheter upon completion of deployment.

Figure 46:
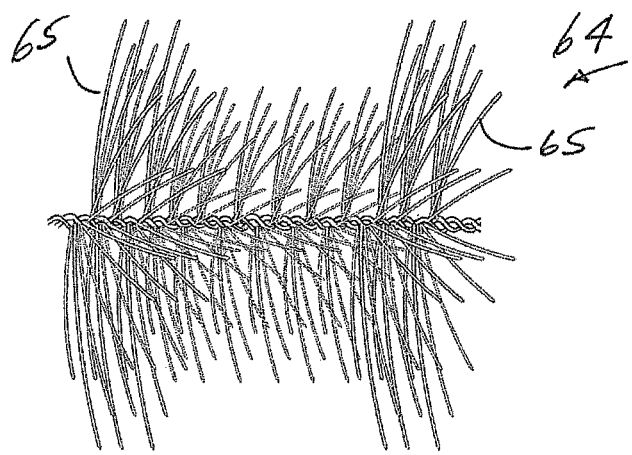
FIG. 46 illustrates a bristle device with stabilisers on both ends.

The prosthesis may have stabilising bristles 65 at one or both ends of a prosthesis 64 as illustrated ion FIG. 46.

Figure 47:
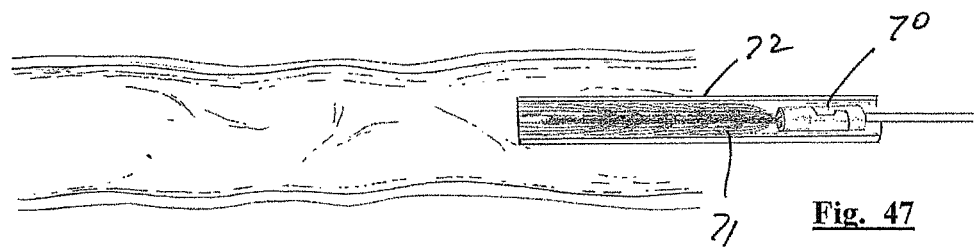
FIGS. 47 to 49 illustrate a delivery system having a slot detachment mechanism.
Figure 48:
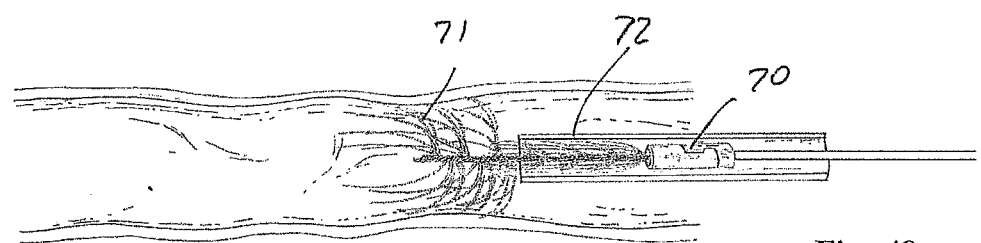
Figure 49:
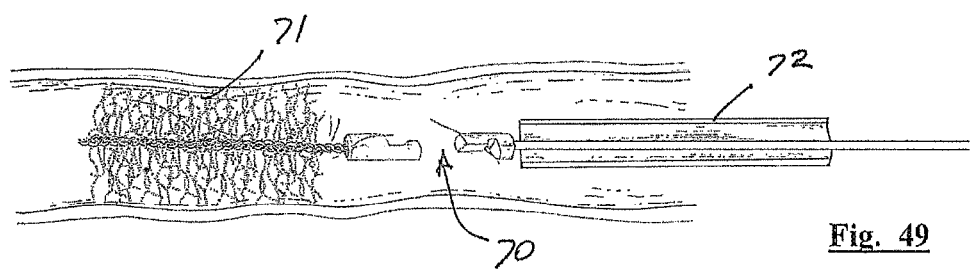

FIG. 47 shows a bristle device 71 in the collapsed configuration within a delivery catheter 72. A slot mechanism 70 is incorporated to enable detachment once the device is fully deployed. The slot detachment mechanism 70 may be radiopaque to enable the physician to establish the position of the mechanism with respect to the catheter tip. FIG. 48 shows the bristle partially deployed. In this configuration the slot detachment mechanism is still engaged since the bristle device cannot move off the axis of the delivery catheter and wire. Accordingly the physician may still retract the bristle device at this point. FIG. 49 shows the bristle device in the deployed configuration. Since the bristle device has exited the catheter it is not constrained to remain on the same axis of the delivery wire and becomes disengaged from the delivery wire.

Figure 50:
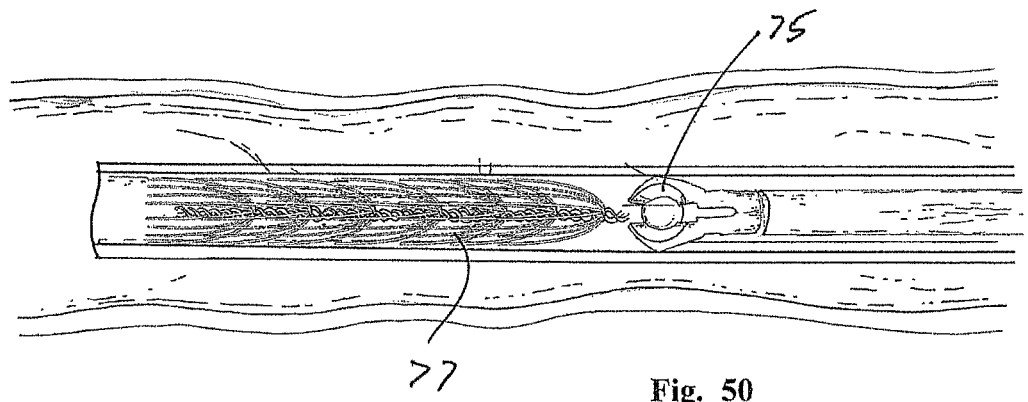
FIGS. 50 to 52 illustrate a bristle device with another detachment feature.
Figure 51:
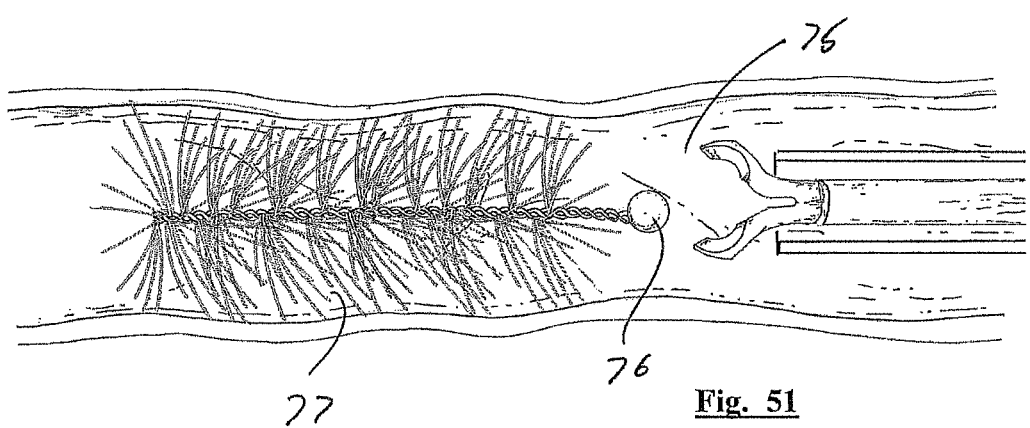
Figure 52:
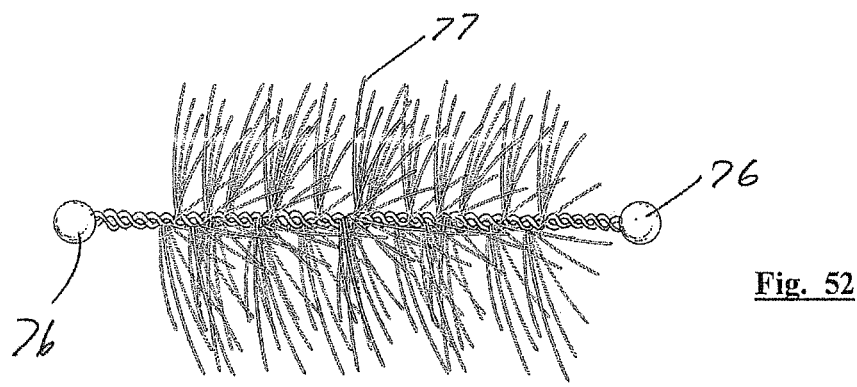

In another embodiment, and referring to FIGS. 50 to 52 a delivery wire with a normally open grasping mechanism 75 illustrated. The grasping mechanism is designed to fit snugly around a ball end or lip 76 on a bristle device 77. This mechanism 75 will always be open if not constrained by the catheter wall. Once the bristle device has been pushed out of catheter, the grasping mechanism 75 pops open detaching the bristle device. Until this point the device can be retracted. Equally this type of mechanism could be used to retrieve the detached bristle device by forcing the normally mechanism closed as it is retracted into the catheter.

FIG. 52 illustrates a bristle device with ball features 76 on both ends.

Figure 53:
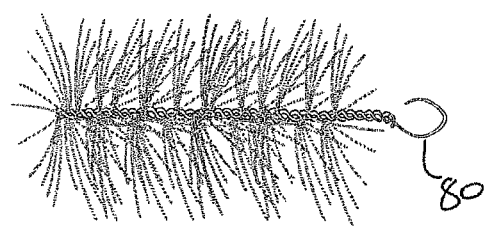
FIGS. 53, 54 and FIGS. 55, 56 illustrate bristle devices with further detachment features.
Figure 54:
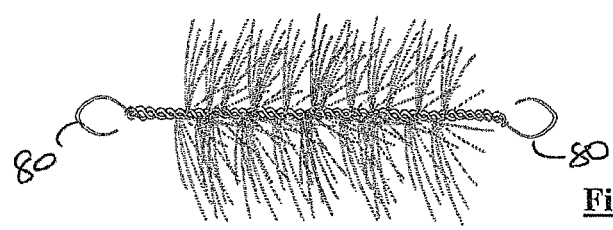

FIGS. 53 and 54 show a bristle device with a hook type mechanism 80 for detachment and retrieval. The bristle device may have a hook at one, or both ends. To ensure that lumen perforation cannot occur, the hook end does not project towards the lumen wall, but towards the bristle portion of the device instead.

Figure 55:
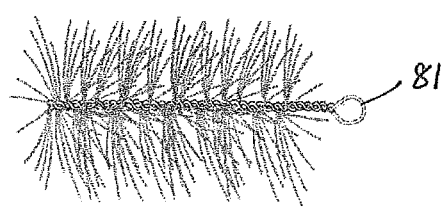
Figure 56:
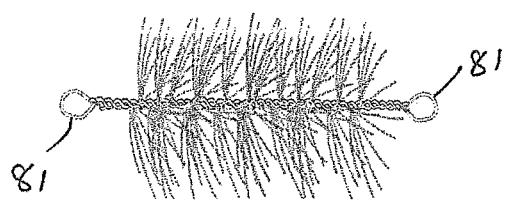

FIGS. 55 and 56 show a bristle device with a loop type mechanism 81 for detachment and retrieval. The bristle device can have a retrieval mechanism at one, or both ends. In this embodiment, the retrieval loop is created by forming the end of the twisted wire of the bristle burn.

Figure 57:
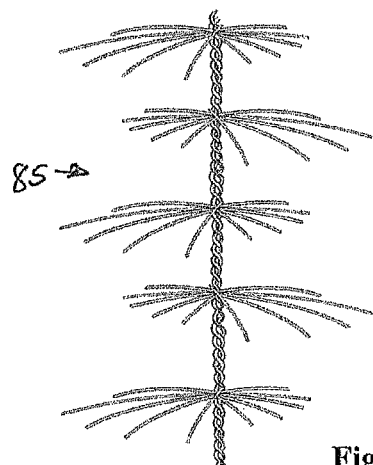
FIGS. 57 and 58 illustrates a bristle device with non uniform bristle lengths.
Figure 58:
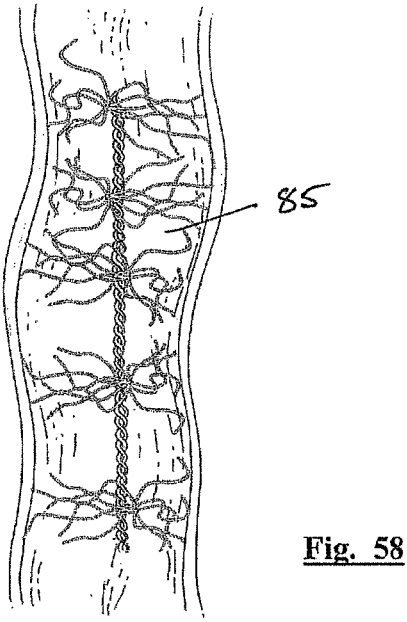

FIG. 57 shows a bristle device 85 with non-uniform bristle lengths about the circumference and along the device length. Variations in the bristle length will reduce the potential for bristle device migration. FIG. 58 shows the device of FIG. 57 deployed in a lumen.

Shorter bristles are less likely to buckle and can therefore transmit a greater load to the lumen wall, increasing the radial or "anchor" force of the device in the lumen, particularly within non-uniform lumen diameters.

Imposition of undulations, roughness and non-uniformity in the lumen wall will increase the resistance to migration of the device due to increased friction.

Figure 59:
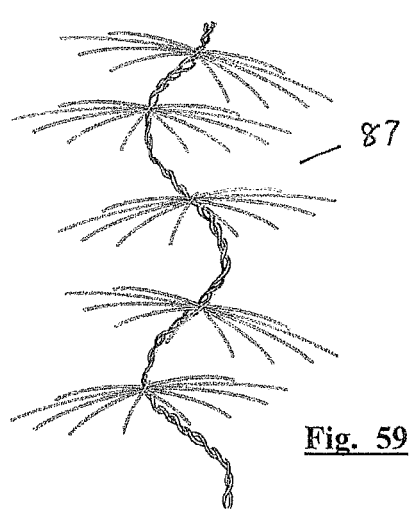
FIGS. 59 and 60 illustrate another bristle device with a curved core and a diameter less than that of the target lumen.
Figure 60:
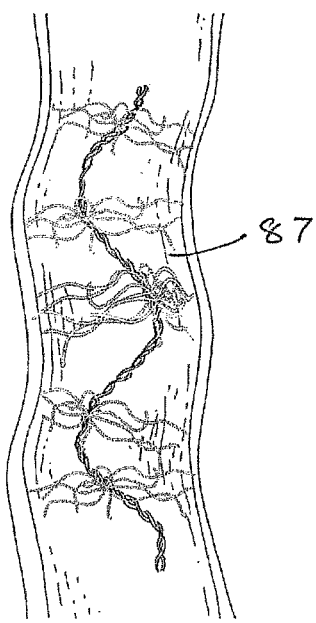

FIG. 59 shows a bristle device 87 with a curved core or stem. In a preferred embodiment the core is helical, and the diameter of the helix is less than the diameter of the lumen. This configuration forces the bristles against the lumen wall, such that the radial force of the bristle device is not dependent on the outward force of the length and diameter of the bristles alone, but also on the distance subtended by the core to the lumen wall. This will increase the anchor force locally and cause undulations/roughness in the lumen wall increasing the resistance to migration. FIG. 60 shows the bristle device 87 deployed within the lumen.

Figure 61:
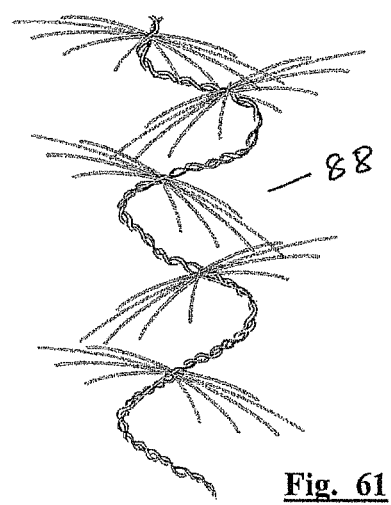
FIGS. 61 and 62 show a further bristle device with a curved core and a diameter greater than that of the target lumen.
Figure 62:
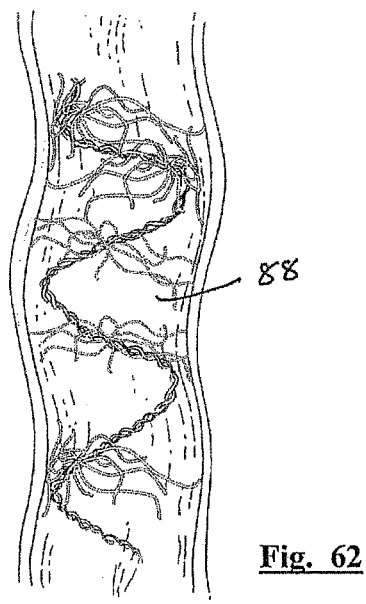

FIGS. 61 and 62 illustrate a bristle device 88 in which a core wire is curved and the external diameter of the core is greater than that of the lumen. This configuration forces both the bristles and the core wire against the lumen wall. In this case the radial force of the bristle device is a combination of both bristle and core, but is dominated by outward force of the core.

Figure 63:
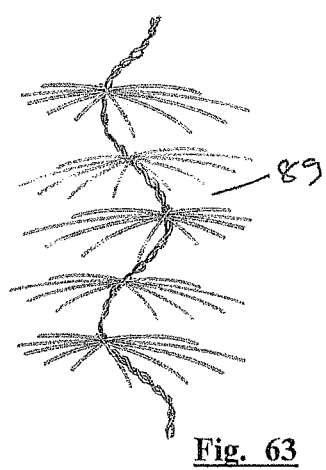
FIGS. 63 and 64 show a bristle device with a curved core and variable bristle lengths.
Figure 64:
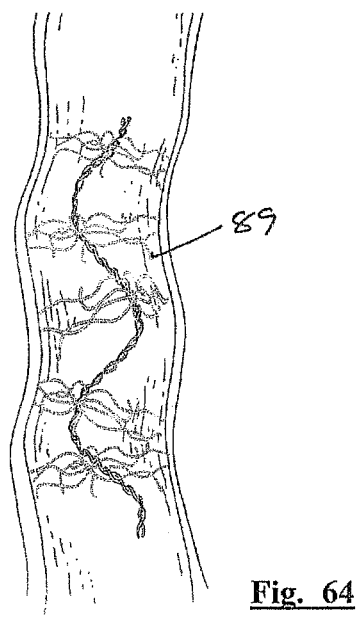

FIGS. 63 and 64 illustrate a bristle device 89 with a curved core and non-uniform bristle length. In this configuration, the bristle device is configured such that the bristle device has a curved core, and variable bristle lengths about the circumference and along the length.

Figure 65:
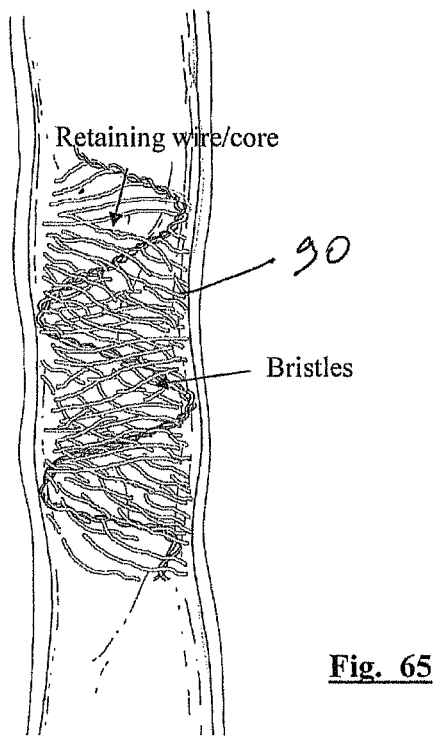
FIGS. 65 and 66 show a bristle device with bristles pointing inwardly from a retaining wire.
Figure 66:
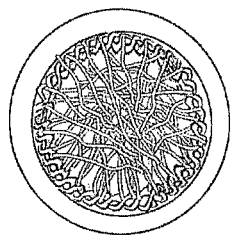

FIGS. 65 and 66 illustrate another embodiment of a bristle device 90 in which all bristles point inward from a retaining wire. In this case the device is anchored entirely by the core/retaining wire.

To enable the physician to deliver the bristle device through tortuous anatomy it must be flexible. This also enables the bristle device to conform to tortuous anatomy once implanted. The flexibility of the prosthesis is defined, primarily, by properties of the core to which the bristles are attached. The flexibility of the core is a function not only of the amount of material in the core, but also its distribution, and material (lower modulus means greater flexibility).

There are certain clinical indications where the optimal clinical outcome would be to simultaneously embolize a vessel and an adjoining, diverging division.

Such a clinical situation is the prophylactic embolization to prevent type II endoleak pre-endovascular aneurysm repair (EVAR). Type II endoleaks can be identified during angiography by the presence of contrast travelling from a peripherally catheterized vessel into the excluded aneurysm sac. The objective when embolizing pre-EVAR is permanent occlusion of the internal iliac artery proximal to its bifurcation to ensure that there is complete occlusion before proceeding to EVAR, as any leak will cause reoccurrence of the issue. Using an angled, adjacent vessel to anchor a portion of the device while deploying the majority of the same device in the larger vessel would provide an anchor for the device, preventing future migration.

Additionally, the internal iliac vein bifurcates into anterior and posterior divisions, which supply pelvic organs as well as the gluteal muscles. It is frequently necessary to embolize one of the anterior or posterior divisions as well as the internal iliac vein. The same approach as described previously would be advantageous; embolizing the adjacent tributary while retracting the remainder of the device to occlude the higher order vessel.

A bristle device, which has the flexibility to be deployed across bifurcating vessels, may be preferable in these instances.

Figure 67:
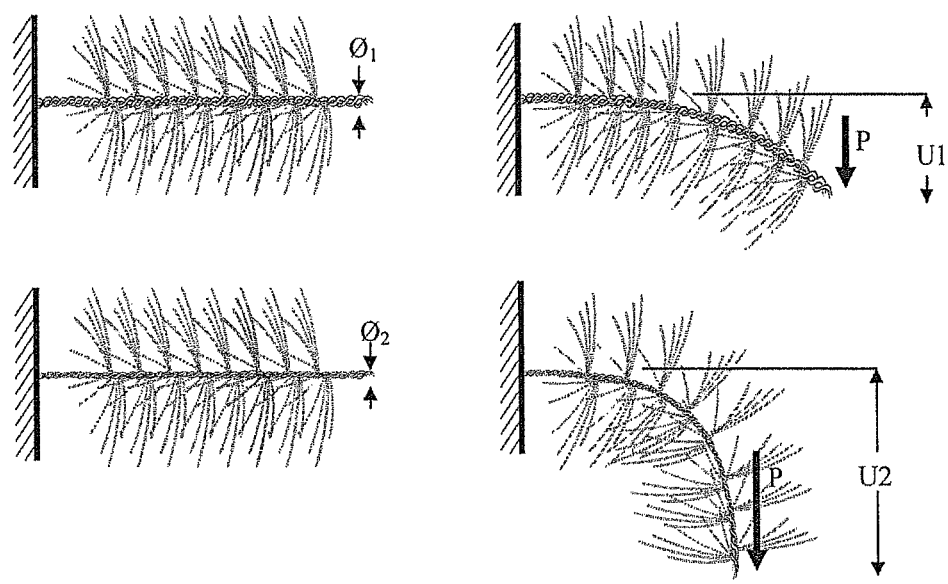
FIG. 67 illustrates the effect of core diameter on flexibility.

FIG. 67 illustrates two device prostheses of the same length with different core wire diameters, $\emptyset_1$ and $\emptyset_2$, where $\emptyset_1 > \emptyset_2$. Note: it is assumed that the core is approximately of circular cross section. One end of the prostheses is fixed and a load, P, is applied to the opposite end causing deflection of the prosthesis. The deflection of the larger diameter device, U1, is much smaller than that of the lower diameter device (U2).

Considering a bristle device with a stainless steel core constructed from twisted wire, its diameter should preferably be constructed from twisted wires of diameter 0.02 inches or less. Otherwise it may not be possible to track the device to the target vessel for deployment.

Figure 68:
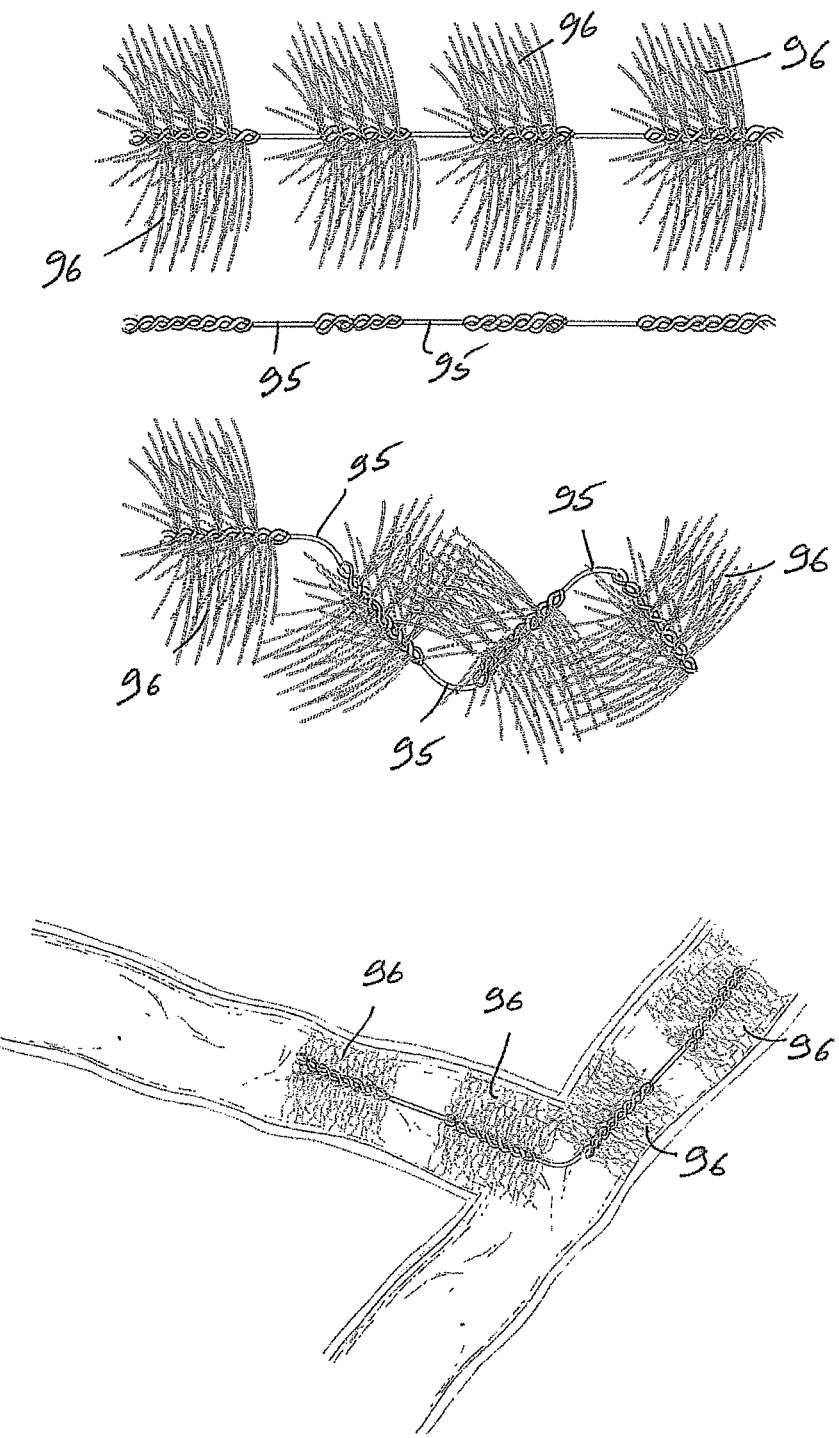
FIG. 68 shows a bristle device with flexible sections and application to bifurcated vessels.

In other embodiments, the flexibility of the device could be improved by having flexible sections 95 between device sections 96 as shown in FIG. 68. Bending within the device is taken up, primarily, by the flexible sections, which can articulate to enable it to pass through a catheter placed in tortuous anatomy, or to be deployed in a curved vessel, or across a bifurcation. In this case the bristle device has flexible sections for articulation Directional control of fluids (e.g. contrast media for angiographic visualization, sclerosant for vessel embolization) cannot be achieved with today's embolization technology. Currently the physician has limited control over fluid dispersion. The current technique involves flushing the fluid through the lumen of a catheter proximal to the target location.

This is of significant relevance in male and female varicocele embolization. A varicocele is a varicose dilation of the pampiniform plexus that drains the testicle and epididymis. The pampiniform plexus drains into the internal spermatic vein. Additional small veins drain into saphenous, external iliac, and internal iliac systems.

For specific embolization procedures e.g. varicocele, additional coils must be deployed in the cephalad portion of a vessel to ensure that that the coils occlude the main branch and all accessible collaterals [7]. To minimize the risk of recurrence, it is often necessary to isolate the most distal (caudal) segment of the target vessel from any potential collateral supply. An alternative to coils is to use an occlusion balloon.

Furthermore in some patients, collateral parallel channels must be selectively catheterized and occluded, either with coils, scleroscant, glue or other embolic agents. When using sclerosants, the intention is to destroy the endothelium to expose subendothelial tissues that in turn will lead to irreversible vascular fibrosis. For certain embolization procedures, e.g. varicocele, if the scleroscant migrates too distally adverse effects can occur e.g. approximately 10% of males develop testicular phlebitis [8].

The sclerosant effect largely depends on a) the time it is in contact with the endothelium and b) the volume and rate of injection [8]. Controlling these variables significantly influence the outcome and also the propensity to damage adjacent non-target vessels.

This proximal migration of the fluid is often referred to as reflux. In some cases, this fluid may contain a drug, sclerosant, fibrin, thrombin, glue, alcohol, beads, or drug coated beads. The physician may require accurate delivery of these agents to prevent non-target therapy.

In the invention a bristle device may be used to prevent proximal migration of a fluid during delivery using a catheter.

When implanted, a bristle device causes a resistance to flow through the device. Similarly, the construction of the device itself means that flow is initiated within the device itself, the flow will have a lower resistance laterally than axially, and will be inclined to fill up any available space outside of the device rather than travel axially through the device itself. Consider the following steps in order to inject a fluid into a vessel, wherein the direction of the flow is controlled using a bristle device.

1. A bristle device is deployed distal to the location in which it is intended to deliver the fluid
2. The bristle device is crossed using a catheter such the tip of the catheter resides on the distal side of the bristle device.
3. The fluid is injected through the catheter tip. It is prevented from migrating through the bristle device and will fill any vessels distal to the device.

Figure 69:
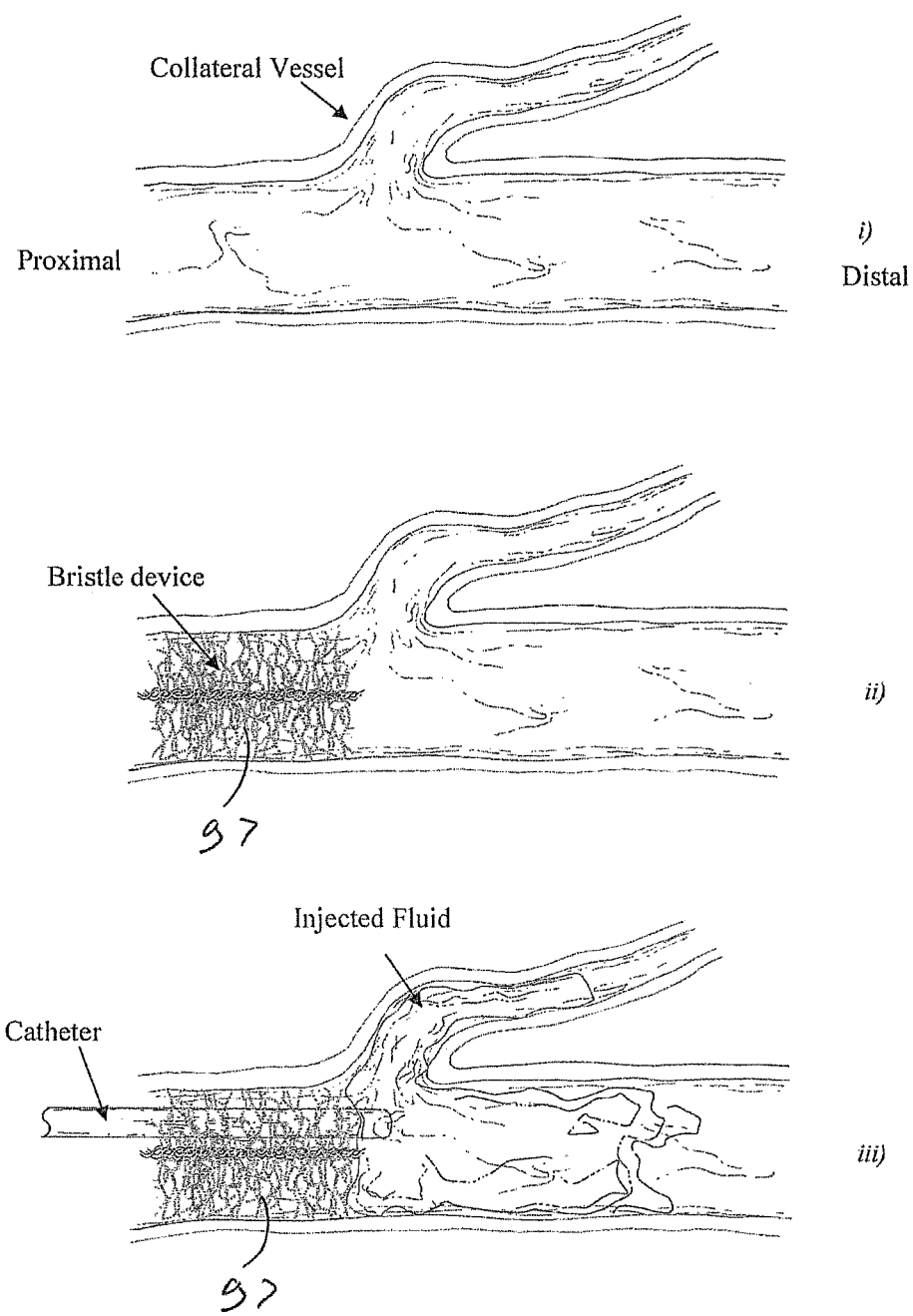
FIG. 69 illustrates the control of fluid using a bristle device.

FIG. 69 illustrates a bristle device 97 in use to prevent proximal migration of a fluid during delivery using a catheter.

In another embodiment, without the presence of individual bristle segments, the path of least resistance for flow is still laterally. This is because the density of bristles laterally is lower than that proximally and distally. Accordingly, the flow will naturally be laterally from the catheter tip. This enables treatment of a collateral vessel and is shown schematically in FIG. 71. FIG. 71 illustrates the use of a bristle device 98 to ensure lateral dispersion of a fluid. Note: Section A-A shows a much higher density of fibres meaning flow will have a higher resistance in this direction (axially) compared to laterally (Section B-B).

The presence of these gaps between the brush segments is also a means to reduce the profile of the bristle device when constrained for placement in a catheter. This is because effect of bristles lying on top of one another, increasing profile is limited.

Figure 72:
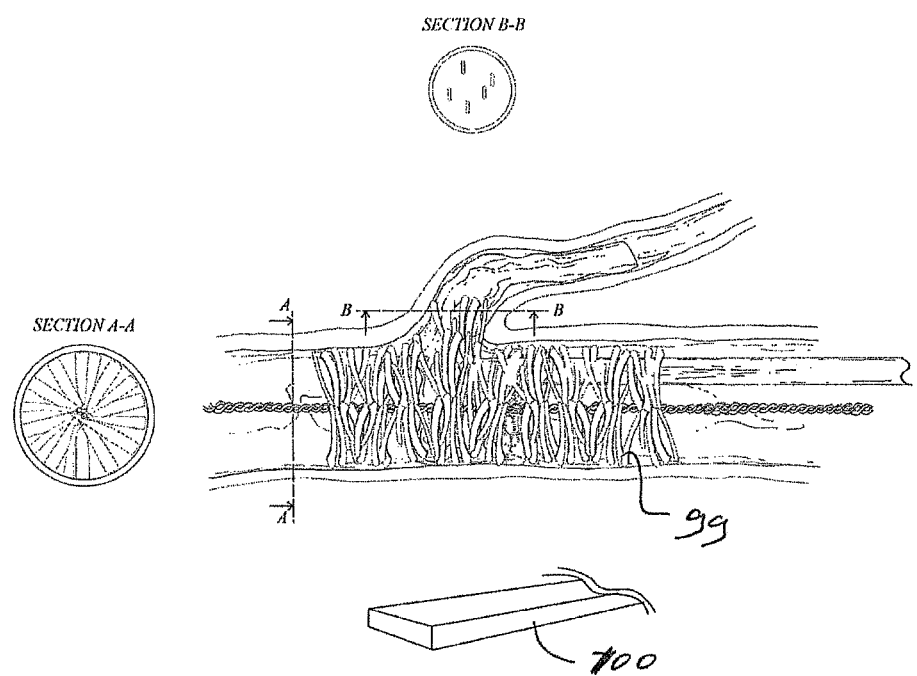

Referring to FIG. 72 in another embodiment, to further improve the ability of a bristle device 99 to prevent longitudinally flow (ensure lateral dispersion of a fluid), bristles with a rectangular cross section 100 are illustrated. The bristles are aligned such that the long axis of the bristle is perpendicular to the centreline of the main vessel. These bristles mean that the path of least resistance is laterally rather than distally or proximally. This can be observed by viewing Section A-A and B-B in FIG. 72. Clearly, it will be easier for a fluid to pass through B-B than A-A due to the geometry of the bristles.

A blood vessel wall is composed of three layers. The innermost layer is called the endothelium and is merely a layer of endothelial cells. The middle and outer layers are known as the medial and adventitial layers respectively.

It has been shown that denudation, or damage to the endothelial lining of a blood vessel can induce vasospasm, and inflammatory reactions leading to vessel occlusion. Removing or damaging the endothelium has a critical role to play in the clotting cascade within a vessel. When the endothelium is removed, the normally isolated, underlying collagen is exposed to circulating platelets, which bind directly to collagen, which is released from the endothelium and from platelets; leading to the formation of a thrombus.

Figure 73:
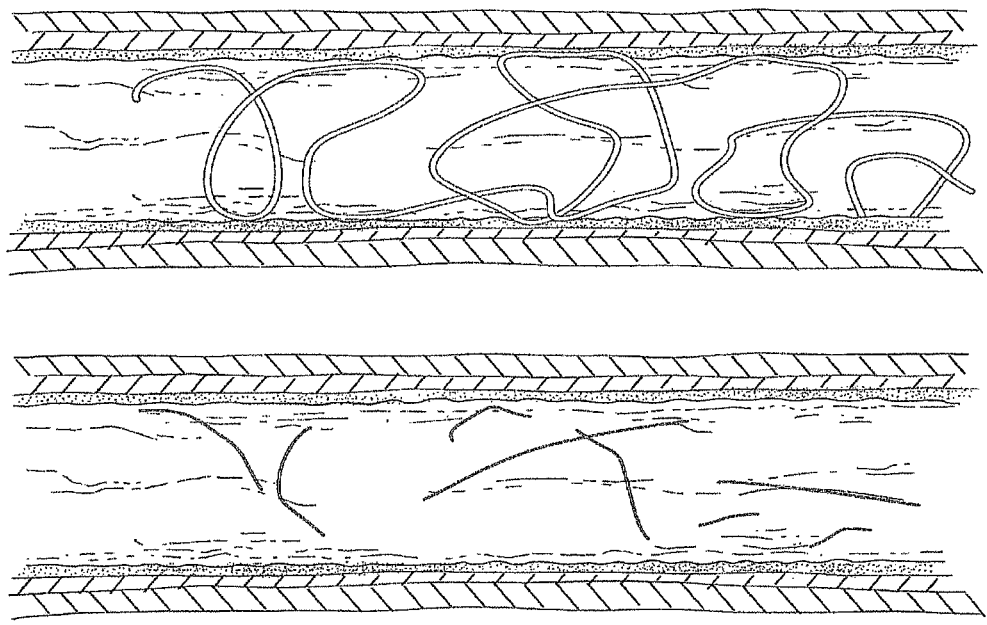
FIG. 73 are typical patterns of contact caused by coils.

Preferably, in order to induce the greatest damage to the endothelium, a bristle device should have a large number of fibres in contact with the lumen wall per unit surface area. Embolization coils do not cause significant denudation to the vessel wall as the degree of wall contact is minimal. This can be seen in FIG. 73.

Figure 74:
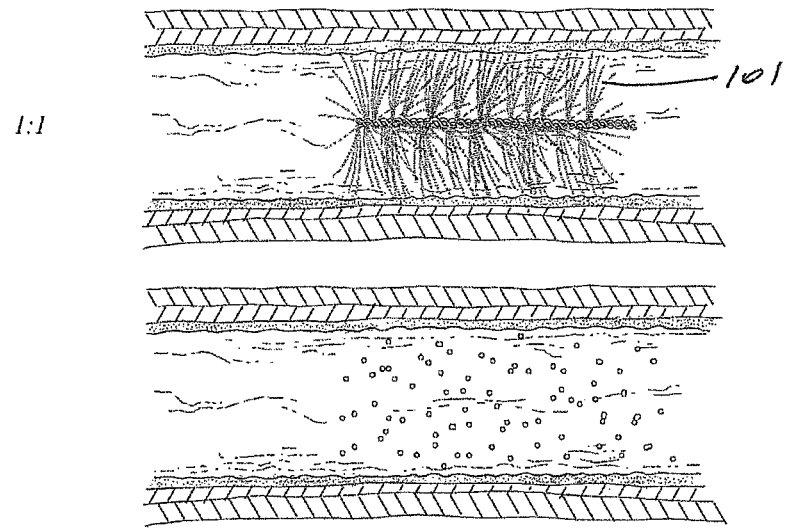
FIGS. 74 and 75 illustrate the effect of oversizing on surface area divided by a bristle device.
Figure 75:
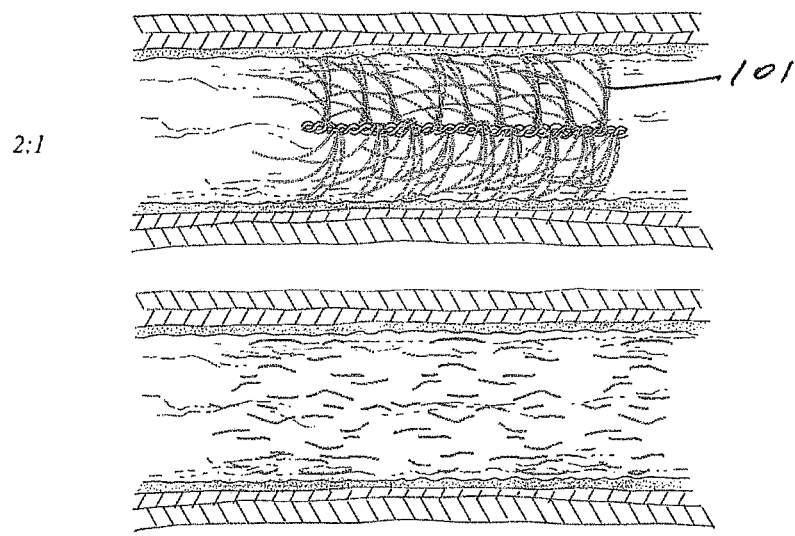

In order for a bristle device 101 to cause significant denudation of a vessel wall it should have a greater diameter than the vessel in which it is implanted. This ensures a larger contact area between fibres and the vessel wall as shown in FIGS. 74 and 75.

Figure 76:
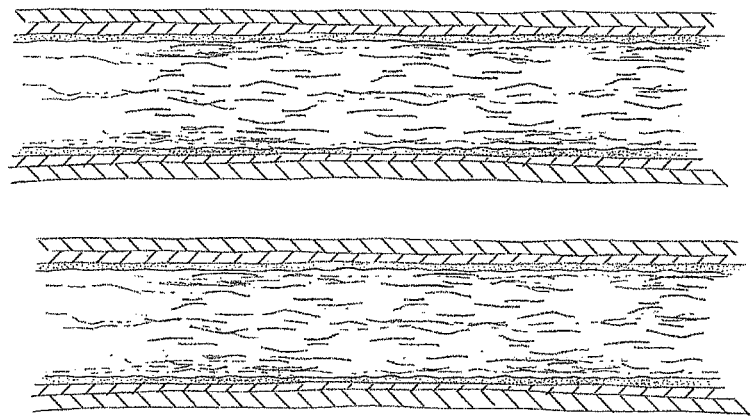
FIG. 76 illustrates the impact of bristle density on vessel damage.

Similarly, a greater number of fibres in contact with the vessel wall will have a greater impact in causing denudation and inducing embolisation. This is shown schematically in FIG. 76. This can be expressed in terms of the bristle length or area in contact with the vessel wall, per unit surface area of the vessel wall.

In some embodiments of the invention we provide
  a bristle device for embolisation with a device diameter to vessel diameter ratio of 1.1 or greater and/or
  a bristle device a minimum length of bristle of 1 mm in contact with a vessel surface area of 2 $mm^2$ and/or
  a minimum of 0.1% of the vessel surface area in contact with the bristle device fibres.

Figure 77:
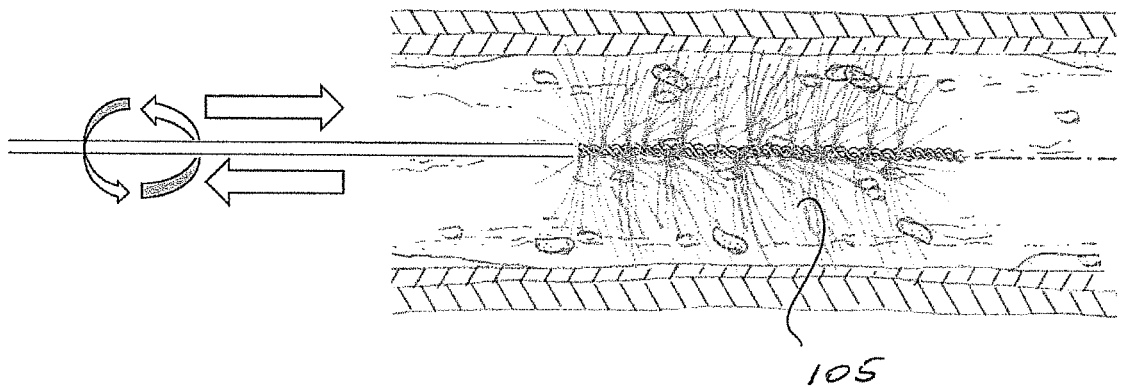
FIG. 77 illustrates a denudation technique using a bristle device.

In another embodiment, the bristle device could be used for denudation of the vessel wall by advancing, retracting and rotating the bristle device at the site of treatment. Once denudation is complete, the prosthesis can be left behind to promote permanent occlusion. FIG. 77 is a schematic showing denudation of the endothelium using translation and rotation of a bristle device 105. This "polishing" action will help strip the endothelial cells from the vessel and enhance the potential for vaso-occlusion. Once complete the prosthesis can be detached from the delivery wire and left in place.

The bristle devices of the invention are also suitable for the treatment of septal defects and patent foramen ovale.

Emboli leading to stroke or to transient ischemic attack can originate in either the systemic venous circulation (paradoxical emboli) or in the systemic arterial circulation. Some patients with cryptogenic stroke have a patent foramen ovale (PFO), an atrial septal defect (ASD), or an atrial septal aneurysm (ASA) that can be identified by echocardiography. These structures have been implicated in the pathogenesis of embolic events, leading to stroke.

Paradoxical emboli: a paradoxical embolus originates in the systemic venous circulation and enters the systemic arterial circulation through a PFO, atrial septal defect, ventricular septal defect, or extracardiac communication such as a pulmonary arteriovenous malformation [10]. The embolus can originate in veins of the lower extremities, in pelvic veins, in an atrial septal aneurysm, or from a clot around the edges of a PFO [10]. Patients with paradoxical emboli can present with cryptogenic stroke.

PFO and ASD: The foramen ovale and its flap-like valve between the right and left atrium are important components of the fetal circulation. In the developing fetus, oxygenated blood from the umbilical vein enters the right atrium via the inferior vena cava and is shunted into the left atrium, circumventing the non-inflated lungs. After birth, a relative increase in left atrial pressure closes the flap, and adhesions frequently result in a structurally intact atrial septum. However, in approximately 25 percent of adults, the foramen ovale remains patent and acts as a potential right-to-left shunt [10].

The closure devices commonly used for percutaneous PFO repair include occluders made of two wire mesh discs filled with polyester fabric. The device is folded into a special delivery catheter, advanced into the heart and through the defect. When the catheter is in the proper position, the device slowly is pushed out of the catheter until the discs of the device sit on each side of the defect, like a sandwich. The two discs are linked together by a short connecting waist. Over time, heart tissue grows over the implant, and it becomes part of the heart.

Complications associated with trans-catheter closure of a PFO/ASD include device embolization or malposition, arrhythmias (usually atrial but include sudden death), and device erosion/perforation [11].

Figure 78:
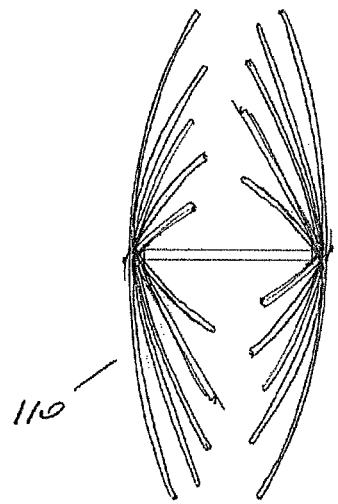
FIGS. 78 to 81 illustrate bristle devices for use in treatment of a septal defect.
Figure 79:
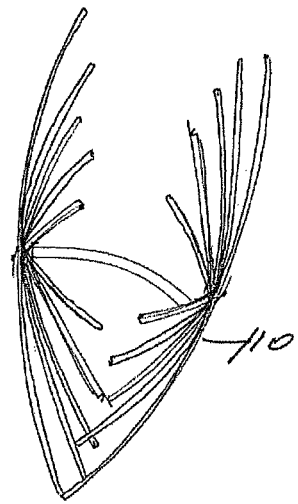

Referring to FIG. 78 a bristle device 110 suitable for occlusion septal defects of a patent foramen ovale is shown. The bristle device comprises at least two distinct device sections, which are connected via a core. Referring to FIG. 79, the device 110 is shown in a tilted configuration highlighting the flexibility of the device. This flexibility will enable the device to conform to the anatomy of the patient, and will ensure good trackability of the device during delivery. The bristle device 110 can be used for septal defect and PFO occlusion. FIGS. 78 and 79 show a septal defect or PFO device 110 which can articulate/bend depending on the target anatomy.

Figure 80:
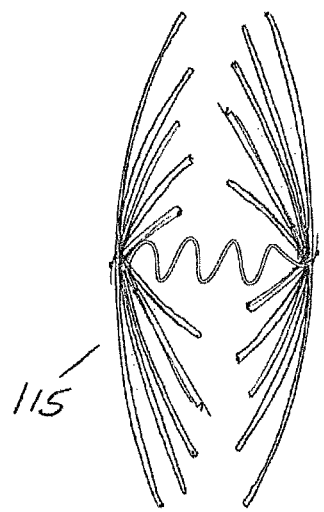
Figure 81:
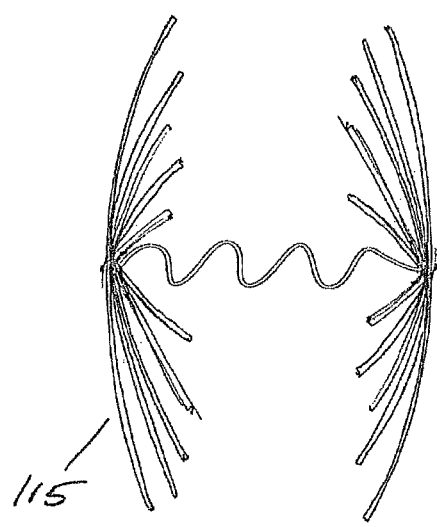

FIGS. 80 and 81 illustrate a septal occlusion device 115, which can stretch depending on the target anatomy (thickness of the septal wall).

Figure 82:
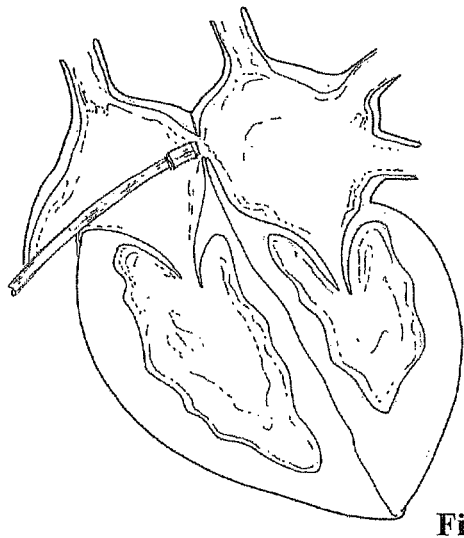
FIGS. 82 to 85 illustrate steps in deployment of the devices of FIGS. 78 to 81.
Figure 83:
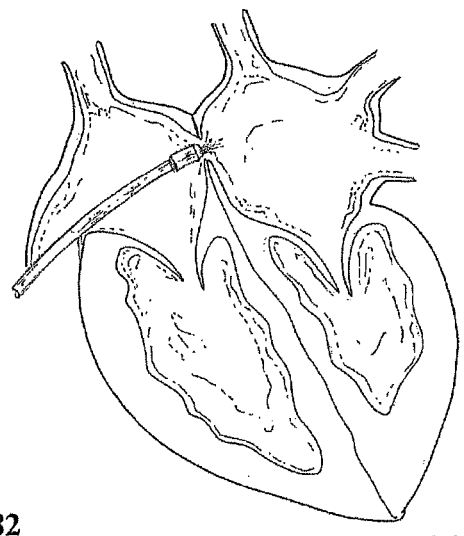
Figure 84:
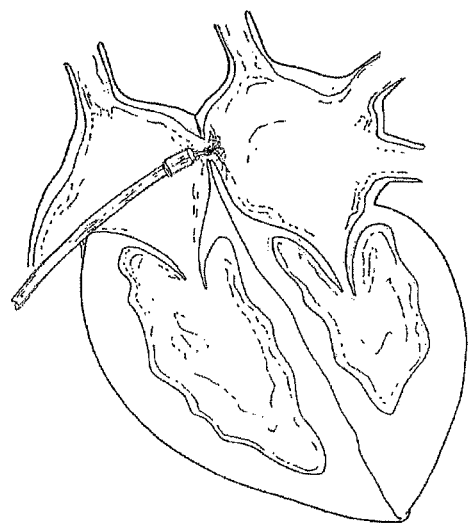
Figure 85:
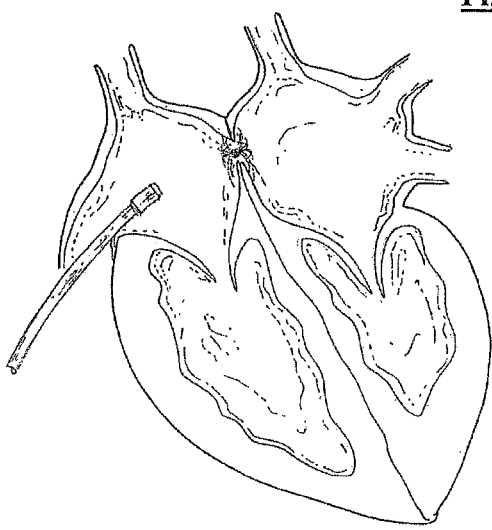

Referring to FIGS. 82 to 85 the implantation of the device 110 or 115 is illustrated. In FIG. 82 a catheter is shown advanced through the right atrium via the inferior vena cava. In FIG. 83 a segment of the device is shown partially deployed. This first segment will provide an anchor on the left atrium side of the patent foramen ovale. FIG. 84 illustrates one segment of the bristle device fully deployed within the left atrium. FIG. 85 illustrates the bristle device fully deployed.

Current technology foreshortens significantly upon deployment into a vessel, between 30-50%, this intended approach attempts to ensure that the pre-shaped coil snaps into its set shape when deployed into a vessel and adheres to the vessel wall [13].

With the exception of glue, which is occasionally used, there is no technology on the market today that does not use this approach.

Therefore it is difficult to embolize the entire length of a large vessel (>10 cm) with technology available today as complete vessel occlusion cannot be achieved and is cost prohibitive.

Additionally there is no product on the market today that can accommodate variable lengths peri-procedurally. This would be advantageous for three reasons:
  Significantly reduce inventory requirements and range of products to be manufactured
  Allows the physician to precisely occlude the portion of the vessel that requires occlusion
  Allows a physician to occlude a bifurcation, feeder vessel or tributary that may contribute towards recanalization FIGS. 86 and 87 illustrate a bristle device 120 with length modifying components 121 that can be extended or retracted intraluminally to adjust the device to the requirements of the target vessel FIG. 88 illustrates deployment of a first bristle bundle into the lumen of the target vessel. Also illustrated is a technique of retracting delivery catheter to extend adjustable section between bristle bundles.

Figure 89:
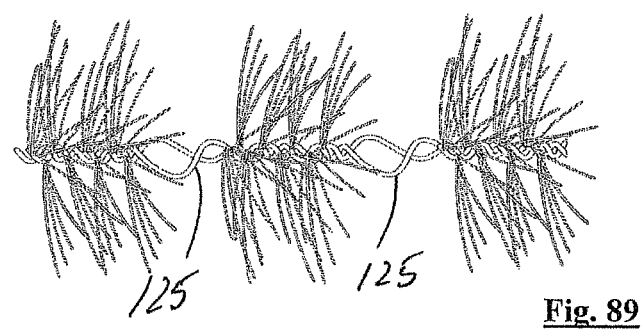
FIG. 89 shows a bristle device with a loosely wound core.
Figure 90:
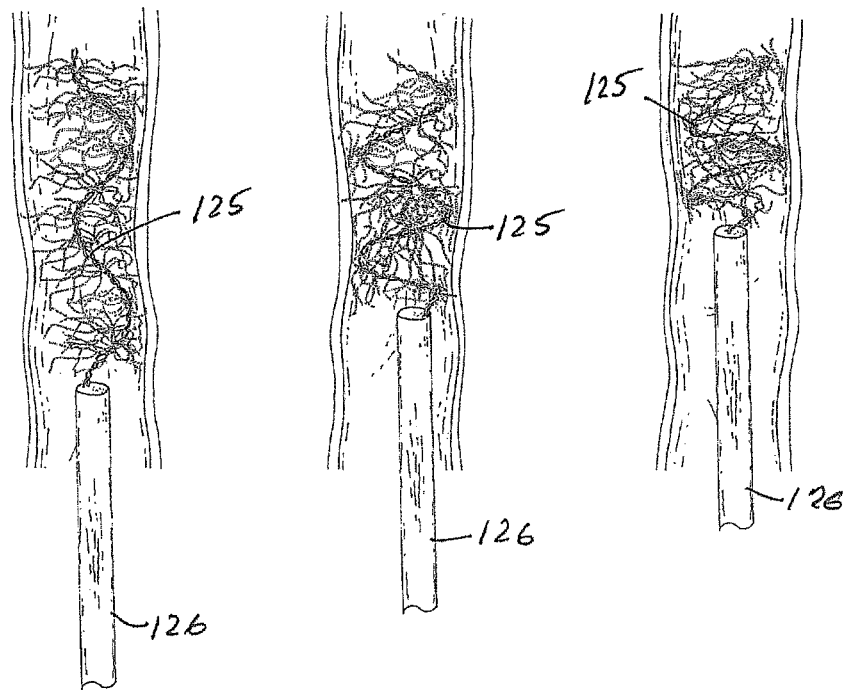
FIG. 90 shows techniques of pushing a delivery catheter to decrease adjustable sections between bristle segments.

FIG. 89 illustrates an alternative embodiment depicting a loosely wound core 125 that accommodates compression of bristle bundles intraluminally FIG. 90 illustrates technique of pushing a delivery catheter 126 forward to decrease adjustable sections between bristle bundles.

In order to induce stasis and cause thrombus formation, ideally no through flow path should exist in the prosthesis that permits blood to flow uninhibited from one end to the other. In reality, some flow path may exist which forces the blood to travel a tortuous path past the prosthesis bristles. If a low resistance flow path is present, occlusion may not occur.

For a bristle device, manufactured using a twisted wire approach, the bristles effectively define a helical surface. The negative of this helical surface defines a flow path.

By its nature, a bristle device may have a through flow path as shown in FIG. 91(a). This will cause turbulent flow and force the blood to interact with a greater surface area of the device, inducing thrombus formation and occlusion. A more tortuous path is shown in FIG. 91(b).

Figure 91:
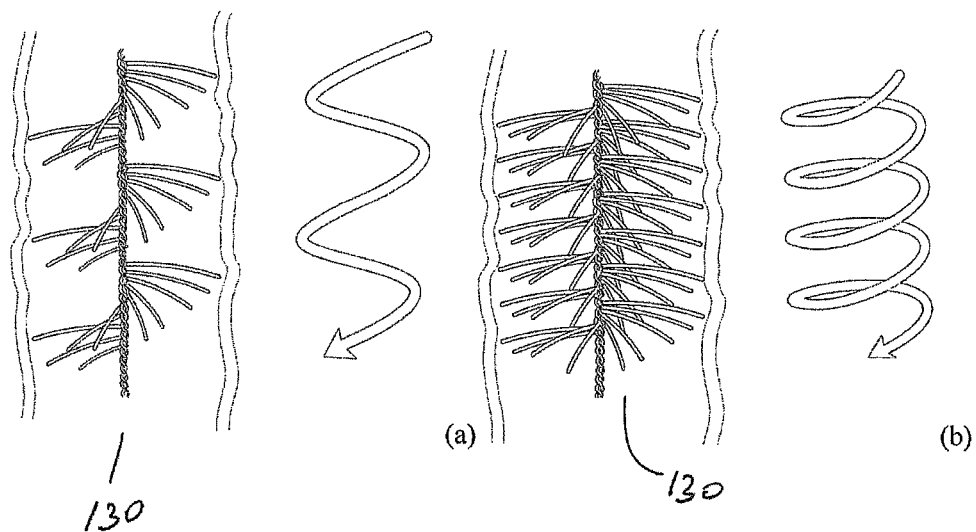
FIG. 91 illustrates bristle devices with a through flow path.
Figure 92:
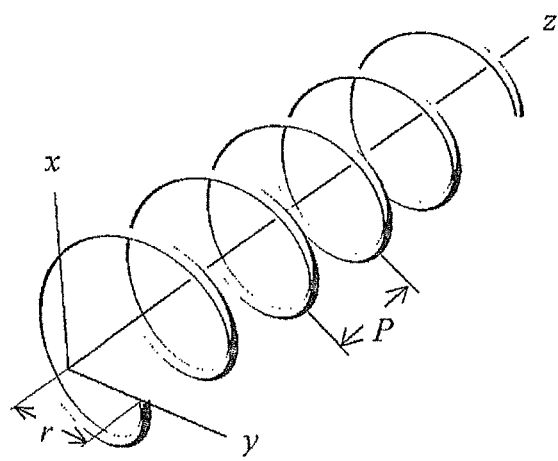
FIG. 92 depicts the flow path in a twisted bristle device.

FIG. 91 illustrates a bristle device 130 with a through flow path. Path is shown adjacent to the bristle device using the arrow. This path could be described as the inverse of volume of the device. This tortuosity of this flow path is defined by the pitch and radius of the helix, which defines the flow path as shown in FIG. 92.

A longer pitch, p, with a small radius, r, will mean a relatively easy and straight flow path. A short pitch with a large radius will imply a longer tortuous flow path. If a flow path does exist, this should be as tortuous and as long as possible to cause occlusion.

Preferably, for inducing occlusion of a blood vessel, the ratio of the pitch to the radius, p/r, of the flow path should be 50 or less. More preferably, the ratio of the pitch to the radius, p/r, of the flow path should be 10 or less. More preferably, the ratio of the pitch to the radius, p/r, of the flow path should be 1 or less. More preferably, the ratio of the pitch to the radius, p/r, of the flow path should be 0.5 or less.

Figure 93:
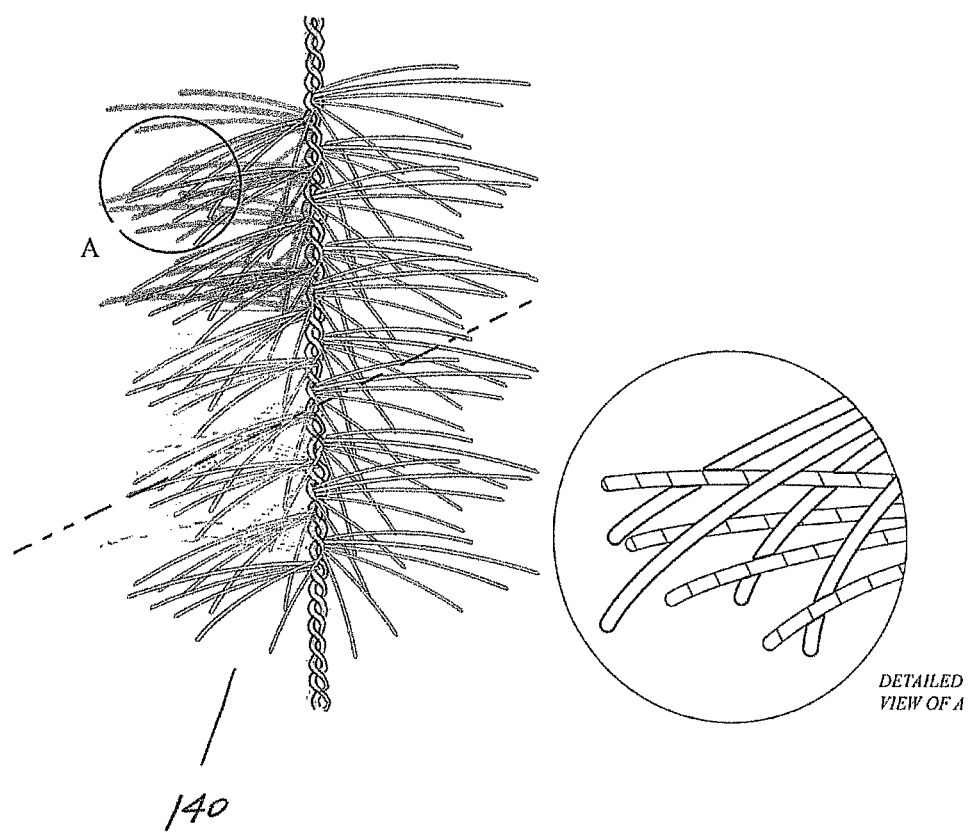
FIG. 93 illustrates overlapping bristle sections to inhibit flow.

If a twisted wire manufacturing approach is used, the ratio of the pitch to the radius of the helix should be such that the adjacent bristle sections of a bristle device 140 overlap as shown in FIG. 93.

FIG. 93 illustrates overlapping bristle sections to inhibit flow path through device.

Another means of ensuring overlapping bristles is to form the device using pre-shaped bristles e.g. saw tooth or spiral, which would increase interaction between bristles.

Figure 94:
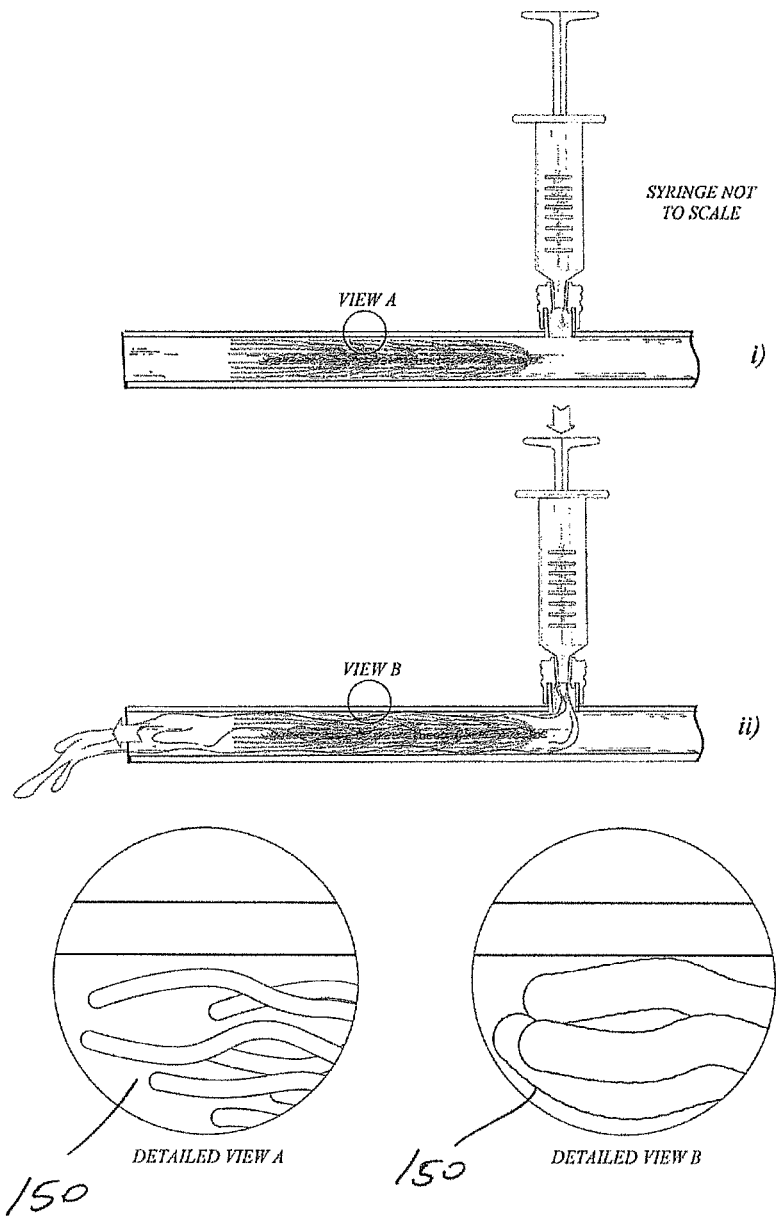
FIG. 94 shows another bristle device with fibres that increase in volume.
Figure 101:
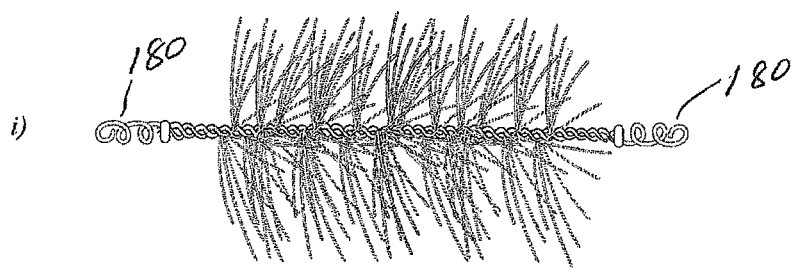
FIGS. 101 to 104 show various bristle tips to prevent vessel perforation upon or after deployment.
Figure 102:
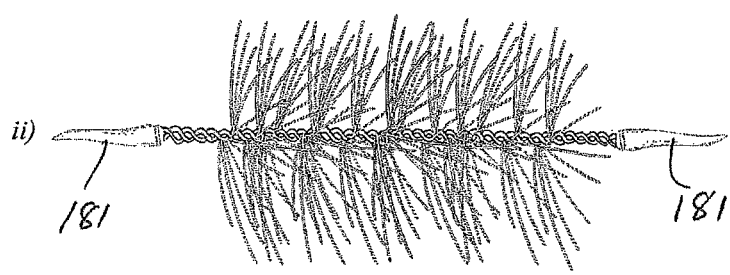
Figure 103:
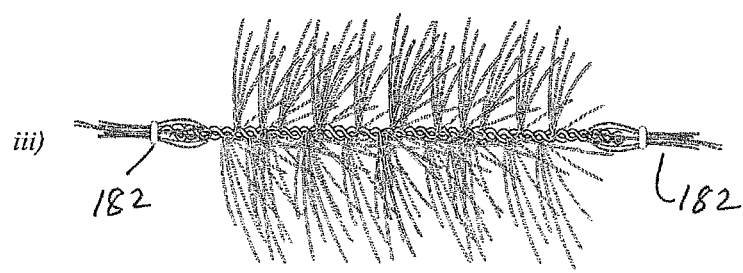

In FIG. 94 a bristle device is shown in which, upon coming in contact with a fluid or blood, the fibres 150 swell up increasing in volume in order to further occlude the lumen in which they reside. This process could be initiated before deployment in the body, or while the bristle device is in its collapsed condition in a catheter/loading tube, as shown in FIG. 94. Similarly, the fibres could be intended to absorb a drug when increasing in volume. This drug would then be delivered to the vessel wall once the bristle device is deployed. FIG. 94 illustrates fibres that increase in volume when in contact with a fluid and or the blood.

In another embodiment, the bristles could have micro fibres 160 in order to increase thrombogenicity and reduce flow path. This is shown schematically in FIG. 95.

Due to adjacent vessel blood flow, an embolus could break away from the clot within the bristle device. The maximum potential size of an embolus which could break away from the bristle device is dictated by the density of the bristles in the device, i.e. the cavities within which thrombus can form in the device. This is defined by the distance between adjacent bristles. Similarly, the ability of the bristle device to cause vessel occlusion can be improved by reducing the distance between adjacent bristles.

Pulmonary Embolism

A common vessel for embolisation is the gonadal vein (for the treatment of varicocele, pelvic vein competence). An embolus could detach from a bristle device, which has been deployed in the proximal portion of a gonadal vein close to the renal vein. This embolus can then travel via the left common iliac vein through the inferior vena cava into the right atrium of the heart. This could potentially travel into the pulmonary arteries causing a pulmonary embolism. In about 5% of people in whom autopsy is done to elucidate the cause of death, pulmonary embolism is unexpectedly found to be the cause. Gardner suggests that the clot size should be limited to 4.5 mm or less using clips in order to prevent a lethal pulmonary embolism [19].

Peripheral Arterial

Ideally any embolus which could break away from the embolisation device is small enough so that it can be thrombolyzed by the body's own defences and remain clinically asymptomatic. A large embolus could cause tissue ischemia and infarction. In 1989, Kazmier proposed a classification for disseminated peripheral atheroembolization into three major clinical presentations: peripheral syndrome, renal syndrome, and visceral syndrome [20]. By definition, microemboli represent atheromatous material with a size less than 1 mm. Accordingly the maximum size embolus which can be permitted to break away from the occlusion device should be less than or equal to 1 mm. To ensure this, the maximum dimension between adjacent bristles which define the cavity from which an embolus could break away should be 1 mm or less. An embolus from a bristle device deployed in the internal iliac artery could enter the common iliac and travel distally to the smaller lumens such as the popliteal and tibial or pedal arteries (shown in FIG. 64). A blockage of these lumens can cause ischemia of the foot, a phenomenon known as trash foot. FIG. 96 shows an embolus detaching from a bristle device which has been deployed in the left internal iliac artery.

Cerebral

The effect of an embolus may not be confined to the peripheral circulation. In the case of the cerebral lumens, an embolus of 1 mm or less may not be tolerated, as emboli of this size can cause a stroke. For aneurysm treatment, the maximum acceptable diameter should be lower than 1 mm. For the case of embolic filters, used to capture emboli which occur during carotid stenting, the pore sizes are approximately 0.8 mm in diameter [21]. Accordingly the gap between the bristles in the deployed configuration should be 0.8 mm or less. FIG. 97—shows a bristle device deployed to treat a cerebral aneurysm. An embolus has broken away from the bristle device which could cause stroke.

In the invention, and referring to FIGS. 98 to 100 to prevent pulmonary embolism a bristle device 170, 171, 172 has gaps between adjacent bristles to limit clot fragments to 4.5 mm or less. To prevent potential for peripheral microembolism the bristle device should have gaps between adjacent bristles of 1 mm or less. For the prevention of cerebral infarction events, the bristle device should have gaps between adjacent bristles of 0.8 mm or less.

FIGS. 98 to 100 illustrate gaps between bristles dictate the potential emboli which could detach form the bristle device. A=4.5 mm, B=1.0 mm, C=0.8 mm.

Figure 104:
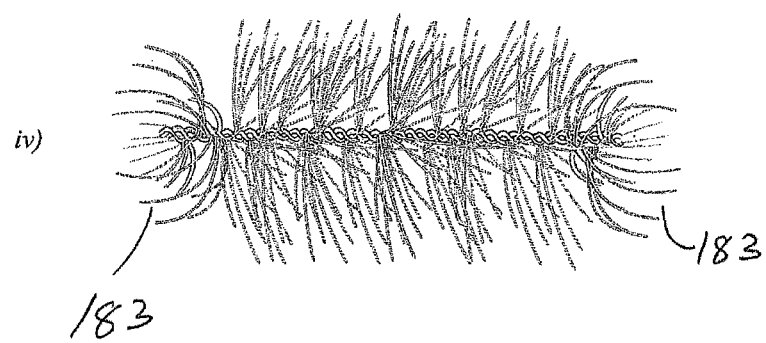

Ideally medical devices that come in contact with a vascular wall or are deployed endovascularly require features that ensure they do not perforate or puncture the vessel wall. Perforations can lead to hematoma and other serious adverse events. It is critical for devices to reduce the risk of internal wall damage. This also provides the clinician with confidence to advance the device against resistance, knowing that the device will not induce trauma. FIGS. 101 to 104 show various bristle tips to prevent vessel perforation upon or after deployment. (i) soft spring 180 (FIG. 101), (ii) soft flexible tips (e.g. made from a polymer) 181 (FIG. 102), (iii) bristles at end of bristle device tied to make an atraumatic end 182 (FIG. 103), (iv) bristles 183 naturally protrude from the end of the device (FIG. 104).

FIGS. 101 to 104 illustrate various embodiments of atraumatic distal and proximal ends designed to prevent vessel wall perforation During percutaneous endovascular treatment an embolization coil is typically delivered to a desired location in the vasculature of a patient through the use of a catheterization procedure. In this procedure, a catheter is inserted into the vasculature of a patient and positioned to be proximal or distal to the targeted anatomical location. Generally, an embolization coil is loaded into the lumen of the catheter and advanced through the catheter using a pusher rod until it reaches and exits through the distal end of the catheter.

Unless "detachable" coils are used this device cannot be repositioned or retrieved once deployed. This technique suffers from difficulty associated with the precise and controlled placement of the embolization coil. Accordingly, there exists a need to develop and provide a system or mechanism for the placement of an embolization coil into the vasculature of a patient that can be done in a precise and controlled manner, while maintaining cost effectiveness, simplicity, reliability, and manufacturability.

Figure 105:
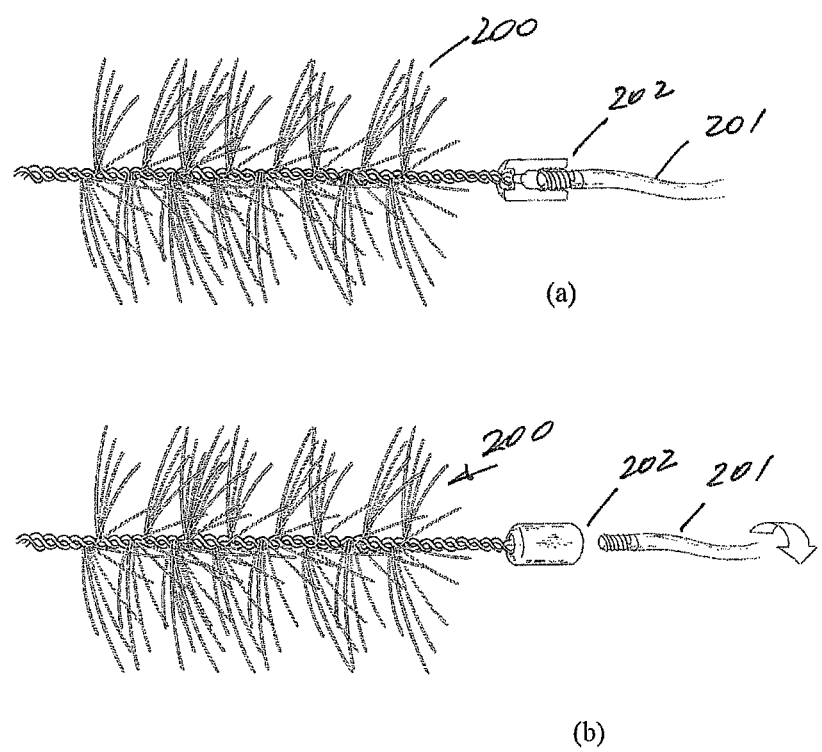
FIG. 105 illustrates the assembly of a bristle device to a delivery wire.

FIG. 105 (a) shows an assembly wherein the bristle device 200 is attached to a delivery wire 201 via a screw mechanism 202. In this assembly detachment is accomplished by unscrewing the delivery wire from the bristle device as shown in FIG. 105 (b).

The interaction of the device, which is constrained radially at least to some extent within the lumen, causes an interference fit. This interference fit occurs due to the propensity of the lumen to try alter (reduce) the diameter of the bristle device, and the propensity of the bristle device to try to alter (increase) the lumen diameter.

The classic relation describing the holding torque of an interference fit assembly using that the assumption that the surfaces have no irregularities and that the contact pressure at the interface is uniformly is distributed, is as follows (Mascle et al., 2011):

$$T_{holding} \alpha \mu_s d_{sh} p A$$

This implies that the holding torque, $T_{holding}$, or torque required to cause a rotation of the bristle device within the lumen is proportional to the coefficient of static friction between the bristle device and the lumen wall, $\mu_s$, the diameter of the lumen, the interference pressure, p, and the area of contact, A.

This implies that interference pressure is a function of the outward radial force of the device against the pressure. The coefficient of static friction between the bristle device and the lumen wall is a function of the lumen and bristle device materials, their roughness and the topography of the geometry which results when the bristle device is deployed within the lumen.

In order to allow detachment of the bristle device from the delivery wire once it has been deployed in the lumen, the torque to unscrew the delivery wire from the bristle device must not exceed the holding torque of the bristle device in the lumen, i.e. $T_{holding} > T_{unscrew}$. If the holding torque does not exceed the torque required to unscrew the delivery wire from the bristle device, the bristle device will simply rotate within the lumen and detachment may not occur.

Figure 106:
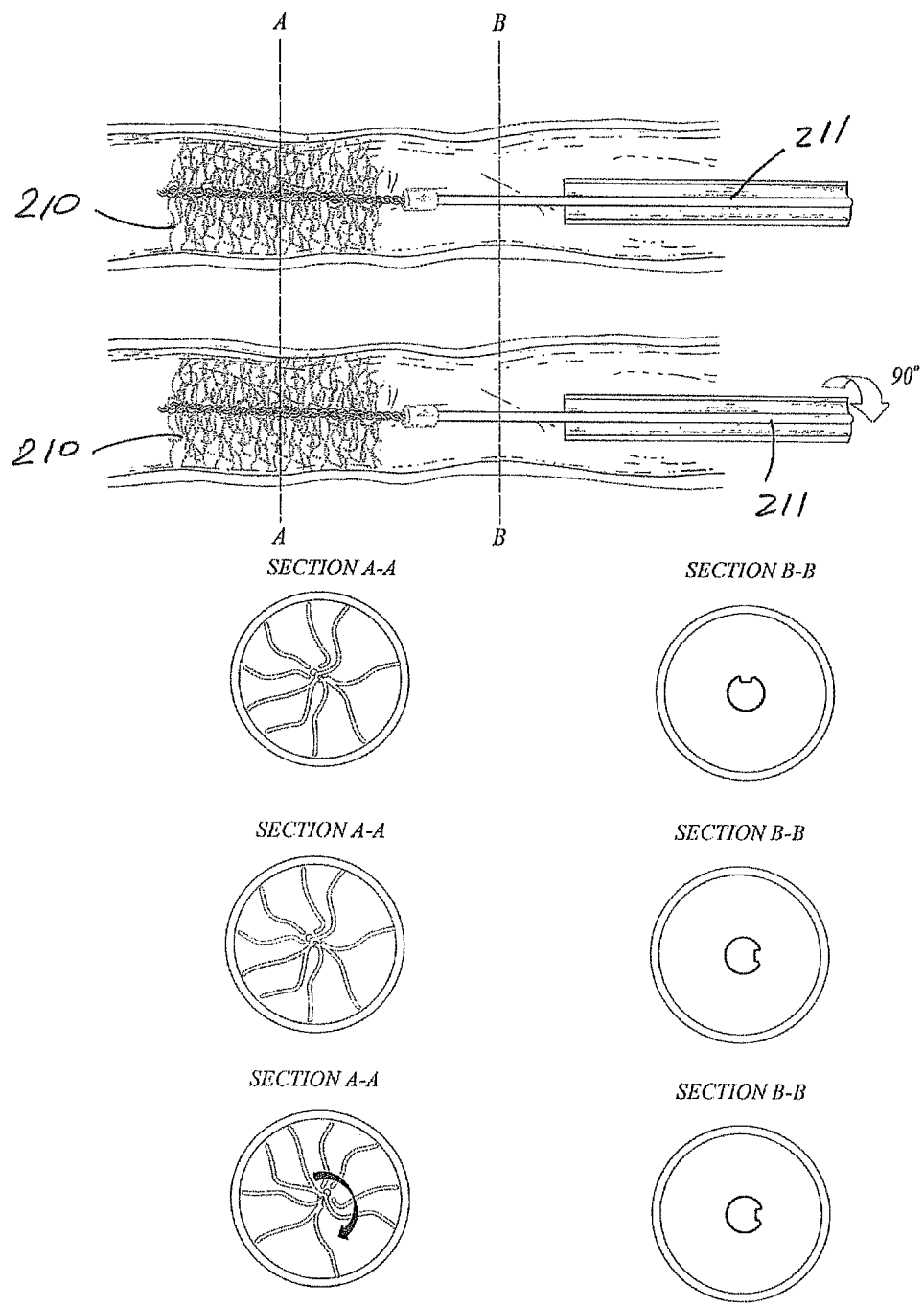
FIG. 106 illustrates a bristle device deployed in a lumen.

FIG. 106 shows a bristle device 210 deployed in a lumen. Section A represents a cross section within the bristle device. Section B represents a cross section at the level of the delivery wire proximal to the detachment mechanisms.

In FIG. 106 (b), the behaviour of the bristle device 210 is shown when no twist is applied to a delivery wire 211 (top). The middle schematic shows the behaviour when some twist is applied to the delivery wire 211 causing the bristle device 210 to rotate within the lumen (undesirable). This occurs because the holding torque of the bristle device does not exceed the torque required to unscrew the bristle device from the delivery wire. In the bottom schematic upon rotation of the delivery wire, no rotation of the device occurs since the holding torque of the bristle device exceeds the torque required.

When coils migrate to unintended locations, they are required to be removed to prevent non-target embolization, tissue ischemia and/or erosion. In general removal of coils is attempted via a percutaneous endovascular approach, by placing a guiding catheter close to the migrated coils and extracted by using a forceps or gooseneck snare to grasp the coil. Technically, removal of coils is very challenging and can take dozens of attempts with various devices to remove [22].

Complications of coil retrieval are significant and can involve [8]:
  Disturbing the rest of the coil nest and exacerbating the problem.
  Damaging other vessels: dissection, occlusion, spasm, rupture of the vessel caused by manipulation of the retrieval device.
  Cardiac arrhythmias if the coil has migrated to the heart.
  Embedding or further distal embolization of the coil or device In the invention we provide a bristle device in which the diameter (size) of the core is greater than that of the core of the bristle device. This enables the bristle device to be retrieved easily using a gooseneck or snare type device.

Figure 107:
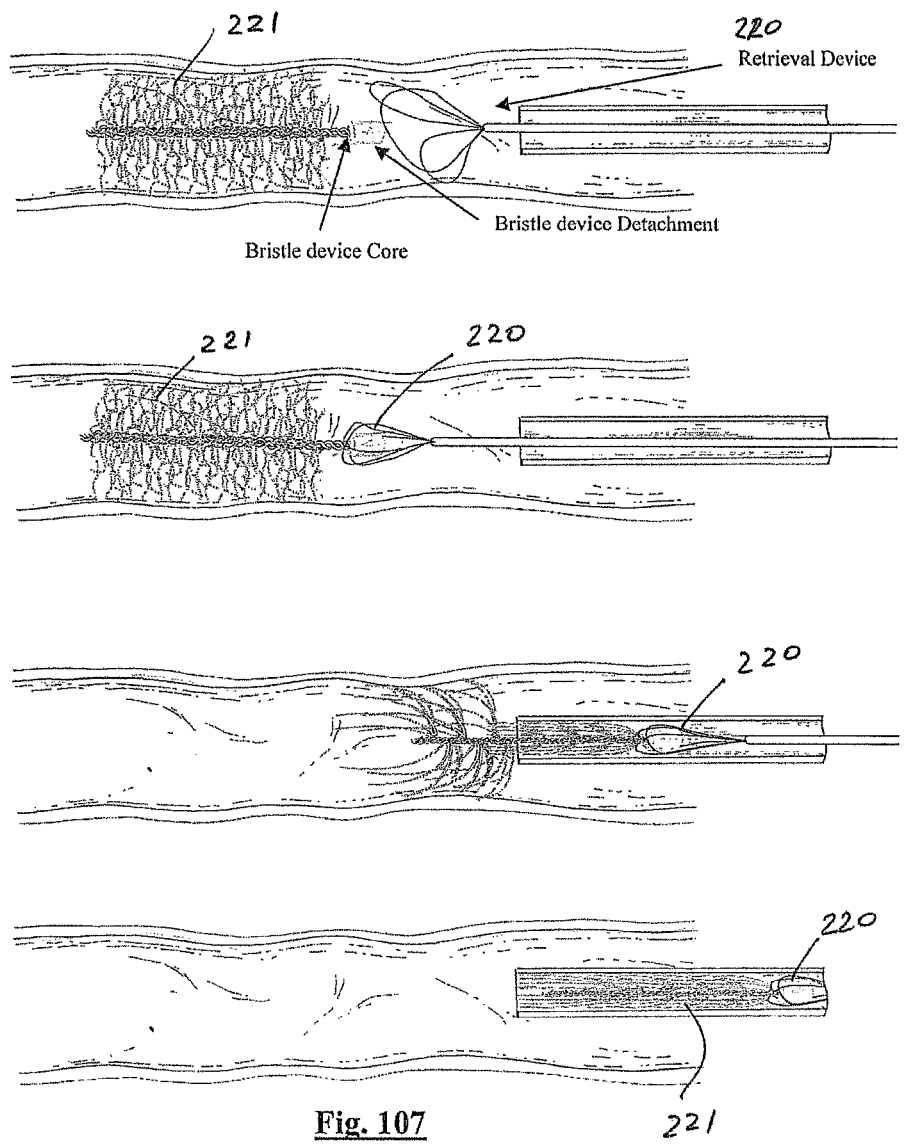

FIG. 107 shows how a retrieval device 220 can easily grasp a bristle device 221 at the screw detachment mechanism. In the top schematic the retrieval device has been deployed from its delivery catheter. In the middle schematic the bristle device detachment mechanism has been grasped in the wire "snare" of the retrieval device and is being retracted into the catheter. The bottom schematic shows the final retraction of the bristle device, now almost entirely in a collapsed condition, into the catheter.

FIG. 108 shows a bristle device 230 with a screw detachment mechanism 231 at both ends. This can be retrieved from a distal or proximal approach.

Migrated coils are generally retrieved using a forceps or a gooseneck snares. These are expensive devices and can significantly add to the procedural cost. It would be advantageous if a coil could be grasped and removed without the necessity to use additional retrieval devices. In the embodiment shown in FIG. 109, the screw detachment mechanism is shaped to guide the delivery wire into the thread to be screwed to the wire and retrieved.

In some cases, it is unnecessary or undesirable to permanently occlude a blood vessel. In these circumstances, using an agent which causes temporary vascular occlusion may be preferable.

Circumstances in which temporary agents may be indicated [8]:
  Pre-operative embolization: e.g., embolization of a renal tumor immediately before resection. In these circumstances, there is no advantage in permanent obliteration of the tumor circulation and any non-target embolization is less likely to be harmful.
  Trauma: it is usually only necessary to arrest bleeding until a stable clot forms and the vessel can heal.
  Upper gastrointestinal tract hemorrhage.

Temporary embolization agents are most beneficial when a vessel can safely be sacrificed but permanent occlusion is not necessary (e.g., internal bleeding associated with trauma). Having a biodegradable embolization device that provide temporary embolization, relieves the clinical issue, and then safely degrades over a specific time period providing the opportunity for systemic blood flow to be restored would be a significant clinical advancement.

In other circumstances, it may be preferable that once embolisation has occurred, that the device, or a portion of the device, biodegrades meaning that the implant:
1. Has no structural role integrity, and therefore does not interfere with surrounding tissues
2. Is no longer present in the body In the invention, either the core, or the bristles, or both the bristles and the core could be biodegradable or absorbable.

The biodegradable/absorbable elements of the device may be composed of synthetic polymers (Poly-lactic acid (PLA) and its isomers and copolymers, Poly-glycolic acid [PGA], Poly-caprolactone [PCL], Poly dioxanone, Poly-lactide-co-glycolide) or Magnesium alloys. This is shown in FIGS. 110 to 112.

Figure 110:
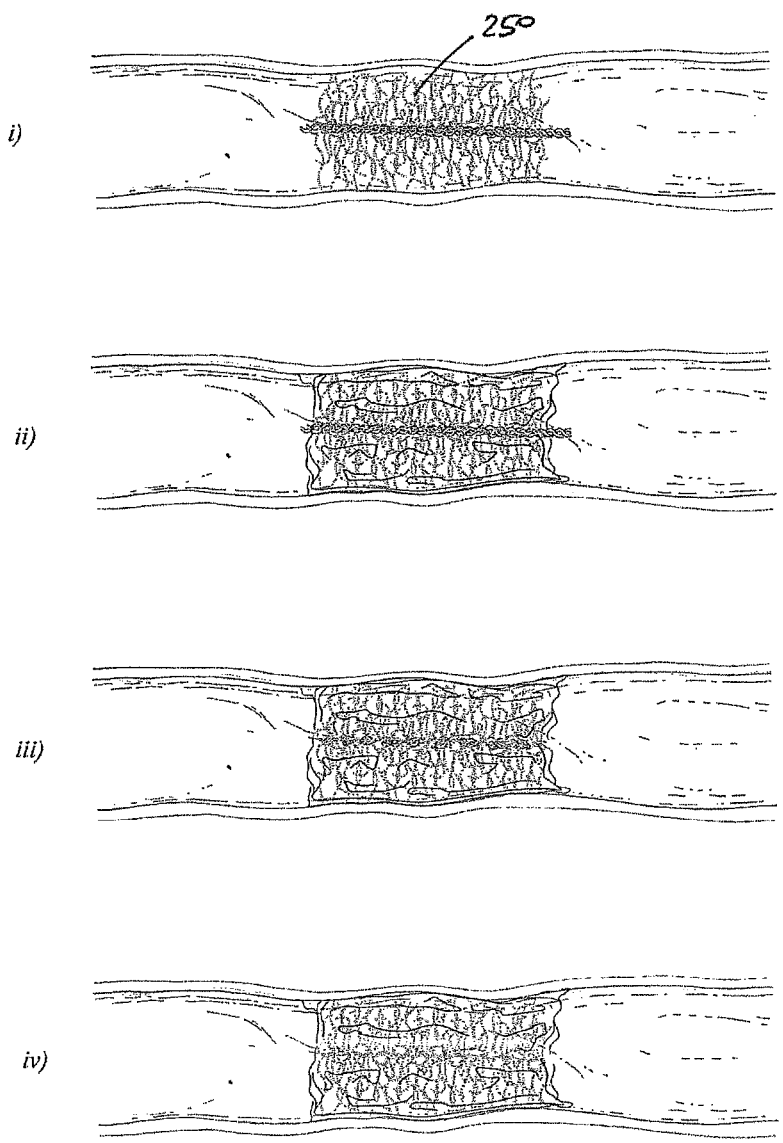
FIGS. 110 to 112 illustrates various degradable bristle devices.
Figure 111:
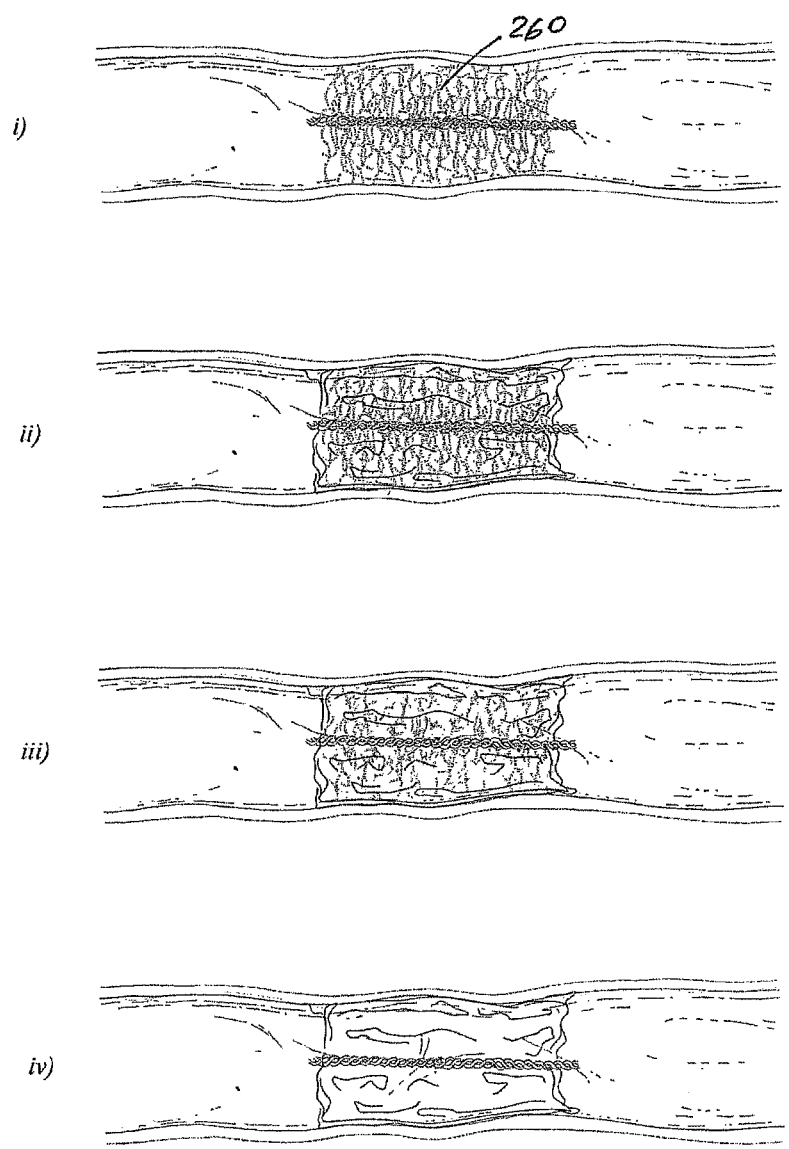
Figure 112:
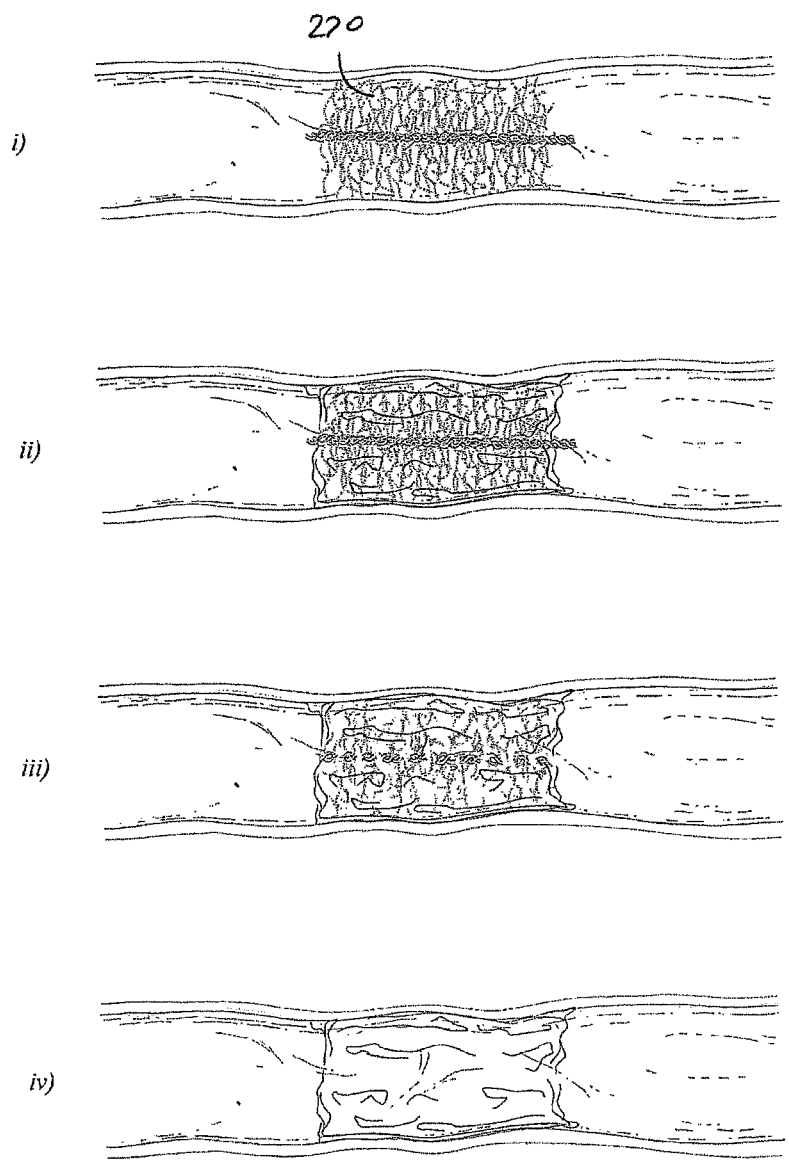

FIG. 110 (i) a bristle device 250 on implantation, (ii) thrombus formed in the bristle device, (iii) core begins to degrade, (iv) core fully degraded leaving only thrombus interspersed with bristles supporting the thrombus FIG. 111 (i) a bristle device 260 on implantation, (ii) thrombus formed in the bristle device, (iii) bristles begins to degrade, (iv) bristles fully degraded leaving only thrombus a supporting core FIG. 112 (i) a bristle device 270 on implantation, (ii) thrombus formed in the bristle device, (iii) core and bristles begin to degrade, (iv) bristle device fully degraded leaving only thrombus within the vessel A number of methods of manufacture may be used to make the prosthesis. FIG. 113 shows a twisted wire device 280 manufactured using a twisted wire method. The fibres are placed between two parallel wires. These wires are fixed at one end and twisted at the other. Upon twisting the wires are formed into a helix causing the bristles to translate from being parallel to being rotationally offset from one another forming a device like construct.

In another embodiment variations in the bristle density can be achieved by varying the pitch of the twisted wire which the holds the bristles in place. This is shown schematically in FIG. 114. FIG. 114 illustrates a twisted wire device with varying core wire pitch in order to vary the density of the bristles.

Figure 115:
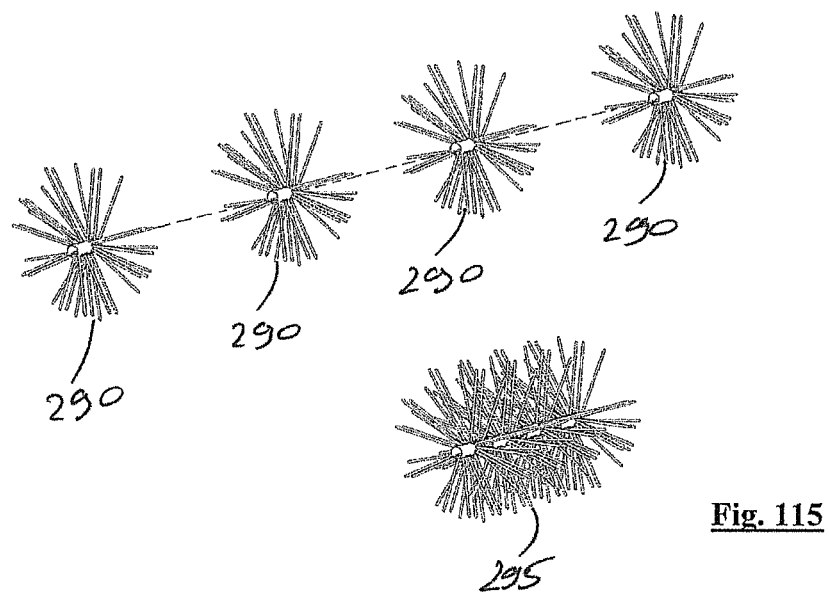
FIG. 115 illustrates manufacture of a bristle device from a number of segments.

FIG. 115 shows a series of individual segments which in this case are extrusions 290, each of which has an array of long elements projecting from the centre. Upon connection of these constructs, a prosthesis 295 suitable for lumen occlusion can be constructed. FIG. 115 illustrates manufacture from a series of device segments, or extrusions.

Figure 116:
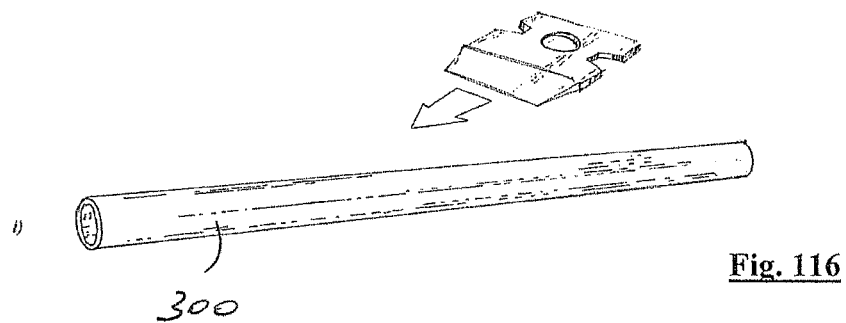
FIGS. 116 and 117 show another method of manufacture.
Figure 117:
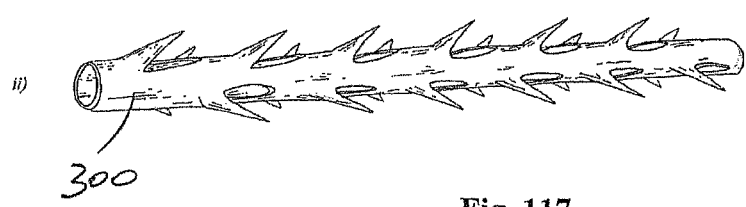

FIGS. 116 and 117 illustrates a method of manufacture in which the entire device is one piece is by cutting the fibres from a core 300. This could also be constructed by laser cutting the tube and passing and expanding element through the lumen to splay out the fibres.

A bristle device may also be used as a platform for therapeutic delivery. This could be an agent to augment thrombogenicity (sclerosant, fibrin, thrombin, glue, alcohol), or to delivery an oncologic drug to treat a tumour, or a device to aid in radiofrequency ablation. This is shown schematically in FIG. 118. The elution time of such an agent could be seconds, hours, days, or years. The coating could be fluid or solid.

Figure 118:
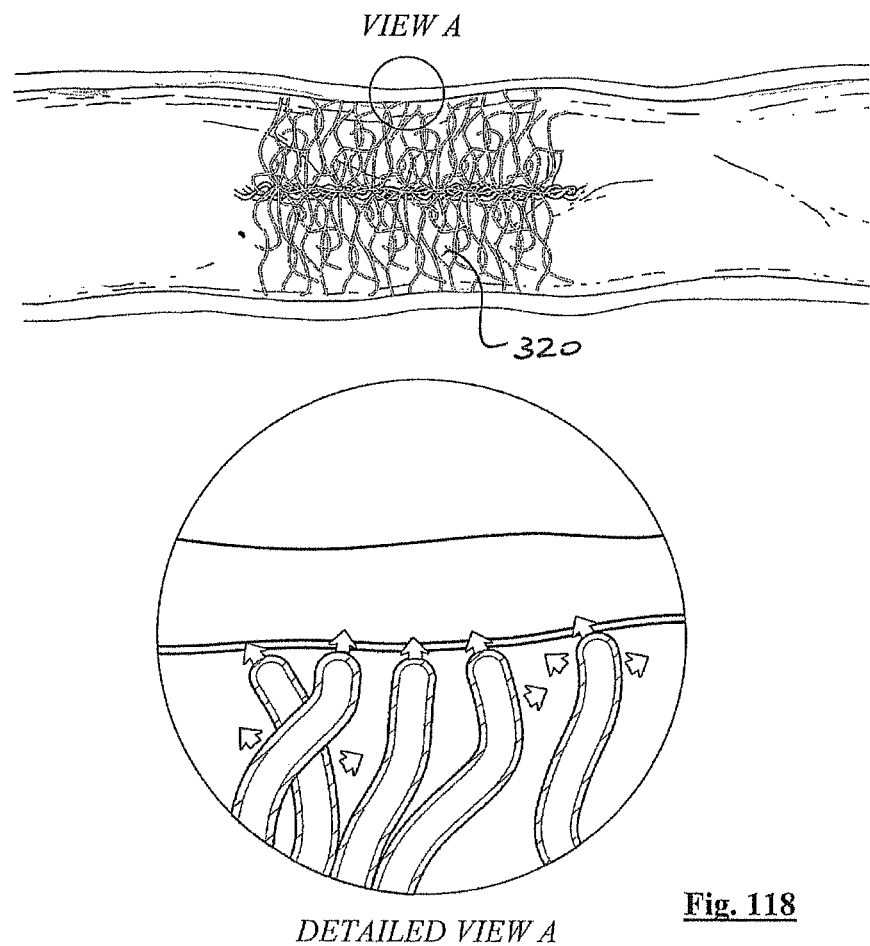
FIGS. 118 to 125 illustrate bristle devices with various drug delivery features.
Figure 119:
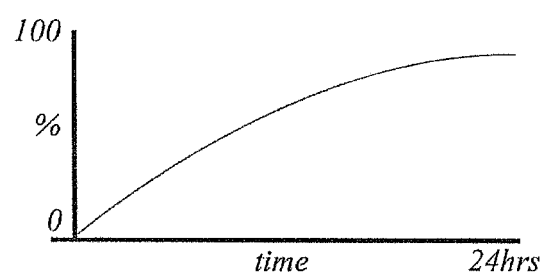

FIGS. 118-119 illustrate delivery of the drug to the vessel wall once a bristle device 320 is in place.

Figure 120:
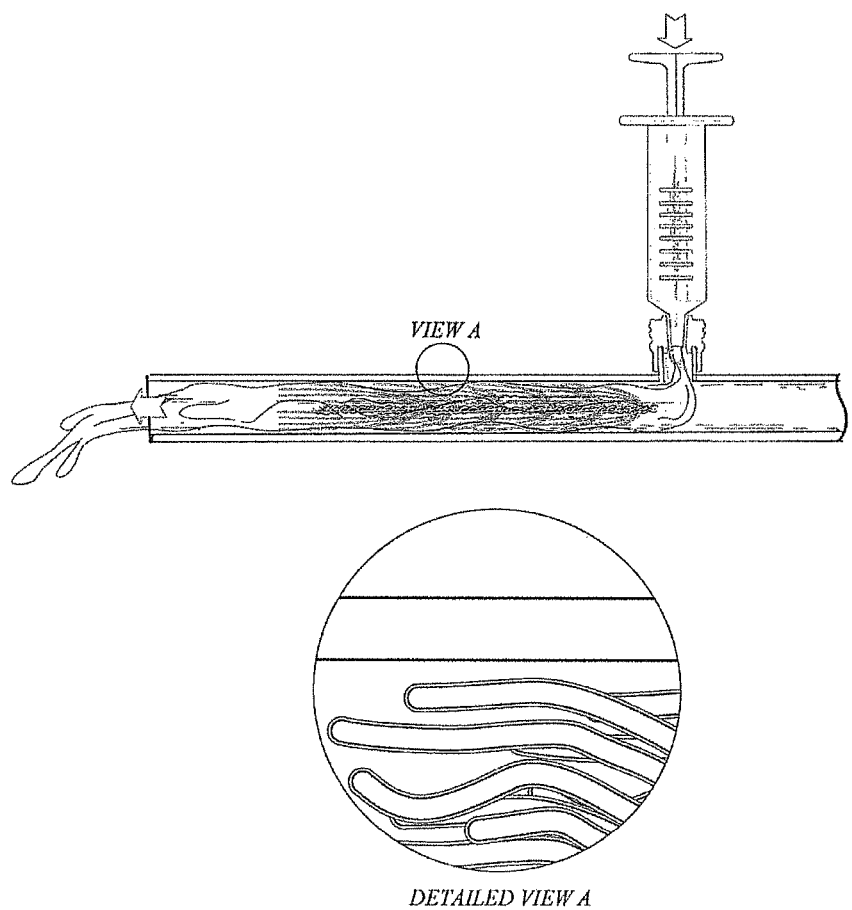

In one embodiment, the device is coated with a drug, or sclerosant, just before being pushed into the catheter (FIG. 120). This drug or sclerosant is then delivered to the vessel wall once it is deployed at the target site. This is shown schematically in FIG. 120. FIG. 120 illustrates flushing of bristle device with a therapeutic prior to being pushed to target vessel. The detailed view shows a coating of the drug on the device fibres following flushing.

The bristles of the bristle device could be further enhanced using striations or holes which can contain a therapeutic. This could increase the volume of therapeutic on the bristle, and to further control its elution over time by restricting the area from which the therapeutic can dissolve, elute.

Figure 121:
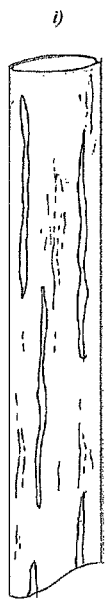
Figure 122:
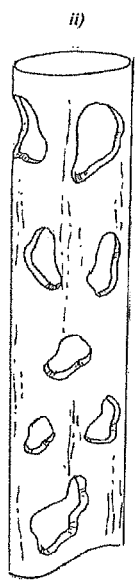
Figure 123:
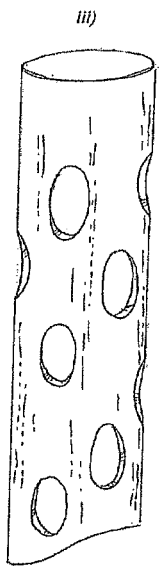

FIGS. 121 to 123 illustrates bristles that are enhanced using pores, striations or holes to hold drug for elution over time.

Figure 124:
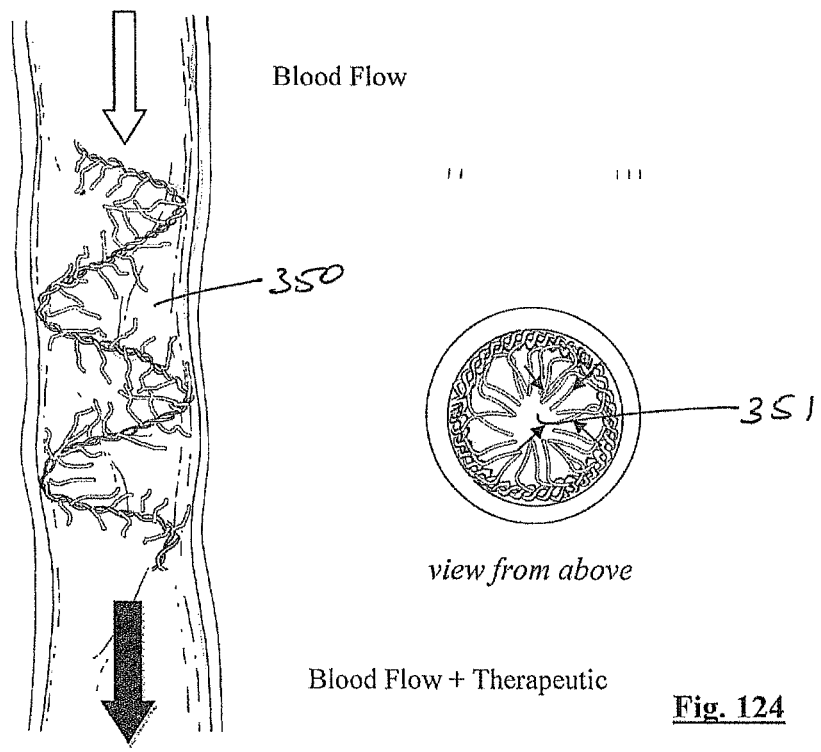

The invention also provides a "perfusion bristle device". This bristle device 350 contains a channel 351 through the centre for flow. As the flow passes the bristles the therapeutic is transferred to the flow, allowing a distal therapy to be delivered. FIG. 124 illustrates the use of a perfusion bristle device for delivery of a drug.

REFERENCES

1. The Technology of Expansion. Terumo Interventional Systems. Downloaded on Feb. 21, 2013 from http://www.terumois.com/products/embolics/AZUR.aspx
2. Ekeh et al., Complications arising from splenic artery embolization: a review of an 11-year experience. The American Journal of Surgery, 205, 250-254, 2013
3. Ryer et al. 2013, Comparison of outcomes with coils versus vascular plug embolization of the internal iliac artery for endovascular aortoiliac aneurysm repair. Journal of Vascular Surgery, Volume 56, Issue 5, November 2012, Pages 1239-1245.
4. Rastogi et al., Unintended coil migration into the right ventricle during the right ovarian vein coil embolization. Vascular and Endovascular Surgery, 2011 October; 45(7).
5. Marsh et al., Coil Protruding into the Common Femoral Vein Following Pelvic Venous Embolization. Cardiovascular Interventional Radiology (2008) 31:435-438
6. Beddy et al., Testicular varicoceles. Clinical Radiology (2005) 60, 1248-1255
7. Beecroft et al., Percutaneous varicocele embolization. Canadian Urological Association Journal. September 2007, Volume 1, Issue 3
8. Kessel et al., Transcatheter Embolization and Therapy. Springer ISBN 978-1-84800-896-0. Published 2010
9. Balian et al. Pelviperineal venous insufficiency and varicose veins of the lower limbs. Phlebolymphology. 2008; 15(1):17-26.
10. Messé et al., Atrial septal abnormalities (PFO, ASD, and ASA) and risk of cerebral emboli in adults. Downloaded on Feb. 22, 2013 from www.uptodate.com
11. St. John Sutton et al., Devices for percutaneous closure of a secundum atrial septal defect. Downloaded on Feb. 22, 2013 from www.uptodate.com
12. Letourneau-Guillon et al., Embolization of Pulmonary Arteriovenous Malformations with Amplatzer Vascular Plugs: Safety and Midterm Effectiveness. Journal of Vascular and Interventional Radiology, Volume 21, Issue 5, Pages 649-656, May 2010.
13. Wang et al., The Amplatzer Vascular Plug: A Review of the Device and its Clinical Applications, CardioVascular and Interventional Radiology, August 2012, Volume 35, Issue 4, pp 725-740.
14. Yoo et al., Preoperative portal vein embolisation using an amplatzer vascular plug. European Radiology (2009) 19: 1054-1061.
15. Pelage et al. What is Azur Hydrocoil and How Does it Work? Presented at Society of Interventional Radiology, 2011.
16. Van Der Vleuten et al., Embolization to treat pelvic congestion syndrome and vulval varicose veins. International Journal of Gynecology and Obstetrics 118 (2012) 227-230
17. Bleday et al., Treatment of haemorrhoids, Sep. 24, 2012. Downloaded on Feb. 22, 2013 from www.uptodate.com
18. Nyström et al., Randomized clinical trial of symptom control after stapled anopexy or diathermy excision for haemorrhoid prolapse. Br J Surg. 2010; 97(2):167.
19. A M Gardner, Inferior vena caval interruption in the prevention of fatal pulmonary embolism, American Heart Journal (impact factor: 4.65). July 1978; 95(6):679-82.
20. Kazmier F J.; Shaggy aorta syndrome and disseminated atheromatous embolization. In: Bergan J J, Yao J S T, editors Aortic surgery Philadelphia: WB Saunders; 1989. p. 189-94.
21. Chung E M, Hague J P, Evans D H., Revealing the mechanisms underlying embolic stroke using computational modelling, Phys Med Biol. 2007 Dec. 7; 52(23): 7153-66. Epub 2007 Nov. 19.
22. Pyung et al., Successful percutaneous endovascular retrieval of a coil in the left ventricle which migrated during embolization for pulmonary arteriovenous malformation. International Journal of Cardiology 163 (2013) e33-e35

Modification and additions can be made to the embodiments of the invention described herein without departing from the scope of the invention. For example, while the embodiments described herein refer to particular features, the invention includes embodiments having different combinations of features. The invention also includes embodiments that do not include all of the specific features described.

Any aspect set forth in any embodiment may be used with any other embodiment set forth herein. Every device and apparatus set forth herein may be used in any suitable medical procedure, may be advanced through any suitable body lumen and body cavity, and may be used for treatment or observation of any suitable body portion.

The many features and advantages of the present disclosure are apparent from the detailed specification, and thus, it is intended by the appended claims to cover all such features and advantages of the present disclosure that fall within the true spirit and scope of the present disclosure. Further, since numerous modifications and variations will readily occur to those skilled in the art, it is not desired to limit the present disclosure to the exact construction and operation illustrated and described, and accordingly, all suitable modifications and equivalents may be resorted to, falling within the scope of the present disclosure.

The invention is not limited to the embodiment hereinbefore described, with reference to the accompanying drawings, which may be varied in construction and detail.

The invention claimed is:

1. A bristle embolization device for delivery into a body lumen comprising a longitudinally extending stem and a plurality of bristles extending generally radially outwardly from the stem wherein there are at least two different groups or types of bristles, wherein one group of bristles are aligned to point in a first longitudinal direction of the stem and another group of bristles are aligned to point in a second longitudinal direction of the stem which is opposite the first longitudinal direction, wherein at least one group of bristles is adapted for occlusion of a lumen to create an embolization, wherein at least one group of bristles are adapted for anchoring the bristle device in a body lumen, wherein the bristle embolization device has a surface area, and wherein lumen occlusion occurs due to thrombogenicity of the bristle embolization device which is a function of the surface area;
   wherein the bristle embolization device has a length, L, and a diameter, Θ, the bristle embolization device having a length to diameter ratio of L/Θ of greater than or equal to 1.0; and
   wherein the at least one group of bristles adapted for occlusion of a lumen are configured so that they are in circumferential contact with the lumen to occlude a cross sectional area of the lumen and to cause denudation of an endothelium layer of the lumen.

2. The bristle embolization device of claim 1 wherein bristles of one group have a thickness which is different than the thickness of bristles of another group.

3. The bristle embolization device of claim 1 wherein one group of bristles is of a different material than the material of another group of bristles.

4. The bristle embolization device of claim 1 wherein one group of bristles is more flexible than another group of bristles.

5. The bristle embolization device of claim 1 wherein one group of bristles are interspersed with another group of bristles.

6. The bristle embolization device of claim 1 wherein the at least one group of bristles are adapted for anchoring the bristle device in a body lumen is provided at the proximal and/or distal end of the device.

7. The bristle embolization device of claim 1 wherein the occlusion group of bristles are located intermediate the proximal and distal ends of the bristle device.

8. The bristle embolization device of claim 1 wherein some of the occluding group of bristles are interspersed with the anchoring group of bristles so that the number of occluding bristles increases form the distal end towards the proximal end of the device.

9. The bristle embolization device of claim 1 wherein one group of bristles extend radially outwardly to one diameter and another group of bristles extend radially outwardly to another diameter which is different than the diameter of the first group of bristles.

10. The bristle embolization device of claim 1 wherein one group of bristles are aligned differently than another group of bristles.

11. The bristle embolization device of claim 1 wherein at least some of the bristles are adapted for delivery of a therapeutic agent.

12. The bristle embolization device of claim 11 wherein the bristles adapted for delivery of a therapeutic agent are at least partially coated with a therapeutic agent.

13. The bristle embolization device of claim 11 wherein the bristles comprise striations and/or holes for containing a therapeutic agent.

14. A bristle embolization device loading system comprising:
   a bristle device for delivery into a body lumen;
   a loading tube; and
   a loading element for loading the bristle device into the loading tube;
   wherein the bristle device comprises a longitudinally extending stem and a plurality of bristles extending generally radially outwardly from the stem, wherein there are at least two different groups or types of bristles, and wherein one group of bristles are aligned to point in a first longitudinal direction of the stem and another group of bristles are aligned to point in a second longitudinal direction of the stem which is opposite the first longitudinal direction, wherein at least one group of bristles is adapted for occlusion of a lumen to create an embolization, wherein at least one group of bristles are adapted for anchoring the bristle device in a body lumen, wherein the bristle embolization device has a surface area, and wherein lumen occlusion occurs due to thrombogenicity of the bristle embolization device which is a function of the surface area;
   wherein the bristle embolization device has a length, L, and a diameter, Θ, the bristle embolization device having a length to diameter ratio of L/Θ of greater than or equal to 1.0; and
   wherein the at least one group of bristles adapted for occlusion of a lumen are configured so that they are in circumferential contact with the lumen to occlude a cross sectional area of the lumen and to cause denudation of an endothelium layer of the lumen.

15. The bristle embolization device loading system of claim 14 wherein the loading element is detachably mountable to the bristle device.

16. The bristle embolization device loading system of claim 14 wherein the loading element comprises a loading wire.

17. The bristle embolization device of claim 1 wherein the stem comprises a flexible section.

18. The bristle embolization device loading system of claim 14 wherein the stem of the bristle device comprises a flexible section.

19. The bristle embolization device of claim 1, wherein the at least one group of bristles adapted for anchoring the bristle device in a body lumen are configured so that while anchoring the device in a body lumen they do not perforate a lumen wall.

20. The bristle embolization device loading system of claim 14, wherein the at least one group of bristles adapted for anchoring the bristle device in a body lumen are configured so that while anchoring the device in a body lumen they do not perforate a lumen wall.

* * * * *

UNITED STATES PATENT AND TRADEMARK OFFICE
CERTIFICATE OF CORRECTION

PATENT NO. : 10,660,645 B2
APPLICATION NO. : 14/205016
DATED : May 26, 2020
INVENTOR(S) : Wayne Allen et al.

Page 1 of 1

It is certified that error appears in the above-identified patent and that said Letters Patent is hereby corrected as shown below:

On the Title Page

Column 2, item (56), U.S. patent documents, cite no. 1, delete "Ensminger" and insert --Ensminger et al.--, therefor.
In page 2, Column 1, item (56), U.S. patent documents, cite no. 8, delete "Galdonik" and insert --Galdonik et al.--, therefor.

Signed and Sealed this
Eighteenth Day of August, 2020

Andrei Iancu
*Director of the United States Patent and Trademark Office*